United States Patent
Sim et al.

(10) Patent No.: US 10,442,796 B2
(45) Date of Patent: Oct. 15, 2019

(54) 2,3,5-SUBSTITUTED THIOPHENE COMPOUND AS PROTEIN KINASE INHIBITOR

(71) Applicants: KOREA INSTITUTE OF SCIENCE AND TECHNOLOGY, Seoul (KR); DAEGU-GYEONGBUK MEDICAL INNOVATION FOUNDATION, Daegu (KR)

(72) Inventors: Tae Bo Sim, Seoul (KR); Woo Young Hur, Seoul (KR); Chi Man Song, Seoul (KR); Ho Jong Yoon, Seoul (KR); Seung Hye Choi, Seoul (KR); Han Na Cho, Seoul (KR); Hwan Geun Choi, Seoul (KR); Nam Doo Kim, Daegu (KR); Jung Beom Son, Daegu (KR); Eun Hwa Ko, Daegu (KR); Hyun Kyoung Kim, Daegu (KR); Joong Heui Cho, Daegu (KR); Seock Yong Kang, Seoul (KR); So Young Kim, Daegu (KR); Yi Kyung Ko, Daegu (KR); Seung Yeon Lee, Gyeongsangbuk-do (KR); Suk Kyoon Yoon, Seoul (KR); Jae Hyun Bae, Daegu (KR)

(73) Assignees: Korea Institute of Science and Technology, Seoul (KR); Daegu-Gyeongbuk Medical Innovation Foundation, Daegu (KR)

( * ) Notice: Subject to any disclaimer, the term of this patent is extended or adjusted under 35 U.S.C. 154(b) by 0 days.

(21) Appl. No.: 15/998,791

(22) Filed: Aug. 16, 2018

(65) Prior Publication Data

US 2019/0047993 A1 Feb. 14, 2019

Related U.S. Application Data

(63) Continuation-in-part of application No. PCT/KR2017/001715, filed on Feb. 16, 2017.

(30) Foreign Application Priority Data

Feb. 16, 2016 (KR) .................. 10-2016-0017991

(51) Int. Cl.
| | | |
|---|---|---|
| C07D 409/12 | (2006.01) |
| A61P 35/02 | (2006.01) |
| A61K 31/381 | (2006.01) |
| A61K 31/4436 | (2006.01) |
| C07D 333/10 | (2006.01) |
| C07D 409/14 | (2006.01) |

(52) U.S. Cl.
CPC .......... *C07D 409/12* (2013.01); *A61K 31/381* (2013.01); *A61K 31/4436* (2013.01); *A61P 35/02* (2018.01); *C07D 333/10* (2013.01); *C07D 409/14* (2013.01); *Y02P 20/55* (2015.11)

(58) Field of Classification Search
CPC ...... C07D 409/12; C07D 409/14; A61P 35/02
USPC ......................................... 546/212
See application file for complete search history.

(56) References Cited

U.S. PATENT DOCUMENTS

| 5,728,868 | A | 3/1998 | Springer et al. |
| 6,414,013 | B1 | 7/2002 | Fancelli et al. |
| 2004/0122016 | A1 | 6/2004 | Cao et al. |
| 2007/0010556 | A1 | 1/2007 | Ashwell et al. |
| 2009/0325925 | A1 | 12/2009 | Renou et al. |

FOREIGN PATENT DOCUMENTS

| JP | 2007517843 | 7/2007 |
| JP | 2007531757 | 11/2007 |
| KR | 1019960703622 | 8/1996 |
| KR | 1020030095188 | 12/2003 |
| KR | 1020050088283 | 9/2005 |
| KR | 1020060127127 | 11/2006 |
| RU | 2006128426 | 2/2008 |
| WO | 2005/066163 | * 7/2005 |

OTHER PUBLICATIONS

International Search Report English translation corresponding to International Application No. PCT/KR2017/001715, dated May 23, 2017, 3 pages.
Qu et al, Role of AXL expression in non-small cell lung cancer, Oncology Letters, vol. 12, issue 6, 2016, pp. 5085-5091.
Nam et al, A pathway-based approach for identifying biomarkers of tumor progression to trastuzumab-resistant breast cancer, Cancer Letters, vol. 356, issue 2B, 2015, pp. 880-890.
D. Rossi, Role of MYD88 in lymphoplasmacytic lymphoma diagnosis and pathogenesis, ASH Education Program Book, vol. 1, 2014, pp. 113-118.
Greenplate et al, Genomic Profiling of T-Cell Neoplasms Reveals Frequent JAK1 and JAK3 Mutations With Clonal Evasion From Targeted Therapies, JCO Precision Oncology,vol. 2, 2018, pp. 1-16.
Leow et al, MEK inhibitors as a chemotherapeutic intervention in multiple myeloma, Blood Cancer Journal, vol. 3, 2013, e105, pp. 1-8.
Yan et al, MERTK Promotes Resistance to Irreversible EGFR Tyrosine Kinase Inhibitors in Non-small Cell Lung Cancers Expressing Wild-type EGFR Family Members, Clinical Cancer Research, vol. 24, 2018, pp. 6523-6535, (Abstract only).
Martin-Broto et al, Clinical implications of KIT and PDGFRA genotyping in GIST, Clinical and Translational Oncology, vol. 12, issue 10, 2010, pp. 670-676, (Abstract only).
Cassier et al, Outcome of Patients with Platelet-Derived Growth Factor Receptor Alpha-Mutated Gastrointestinal Stromal Tumors in the Tyrosine Kinase Inhibitor Era, Clinical Cancer Research, vol. 18, issue 16, 2012, pp. 4458-4464.

(Continued)

*Primary Examiner* — Niloofar Rahmani
(74) *Attorney, Agent, or Firm* — Myers Bigel, P.A.

(57) ABSTRACT

The present invention relates to a novel 2,3,5-substituted thiophene compound having inhibitory activity against kinases, an anticancer agent including the compound as an active ingredient, and a method for preparing the compound.

8 Claims, 10 Drawing Sheets

(56) References Cited

OTHER PUBLICATIONS

Higuchi et al, Clinical significance of platelet-derived growth factor receptor-β gene expression in stage II/III gastric cancer with S-1 adjuvant chemotherapy, Oncology Letters, vol. 13, 2017, pp. 905-911.

Kato et al, RET Aberrations in Diverse Cancers: Next-Generation Sequencing of 4,871 Patients, Clinical Cancer Research, vol. 23, issue 8, 2017, pp. 1988-1997.

Singh et al, TRAF4-mediated ubiquitination of NGF receptor TrkA regulates prostate cancer metastasis, The Journal of Clinical Investigation, vol. 128, issue 7, 2018, pp. 3129-3143.

Li et al, High-affinity neurotrophin receptors and ligands promote leukemogenesis, Blood Journal, vol. 113, issue 9, 2009, pp. 2028-2037.

Yu A. Dyadin. "Supramolecular Chemistry. Clathrate Compounds" Soros Educational Journal, 2: 79-88 (1998) (English translation included for relevant pp. 79 & 87; 11 pages total).

Jiro Tsuji Organic synthesis pioneered by transition metals, its various reaction forms and latest results, Kagaku Dojin, 1st edition (1997) (English translation included for relevant pp. 15-18 & 39-42; 9 pages total).

English translation of "Reason for rejection" issued for corresponding Japanese Patent Application No. 2018-561463 (3 pages) (dated May 27, 2019).

English translation of office action and search report issued for corresponding Russian Patent Application No. 2018130703 (6 pages) (dated May 23, 2019).

\* cited by examiner

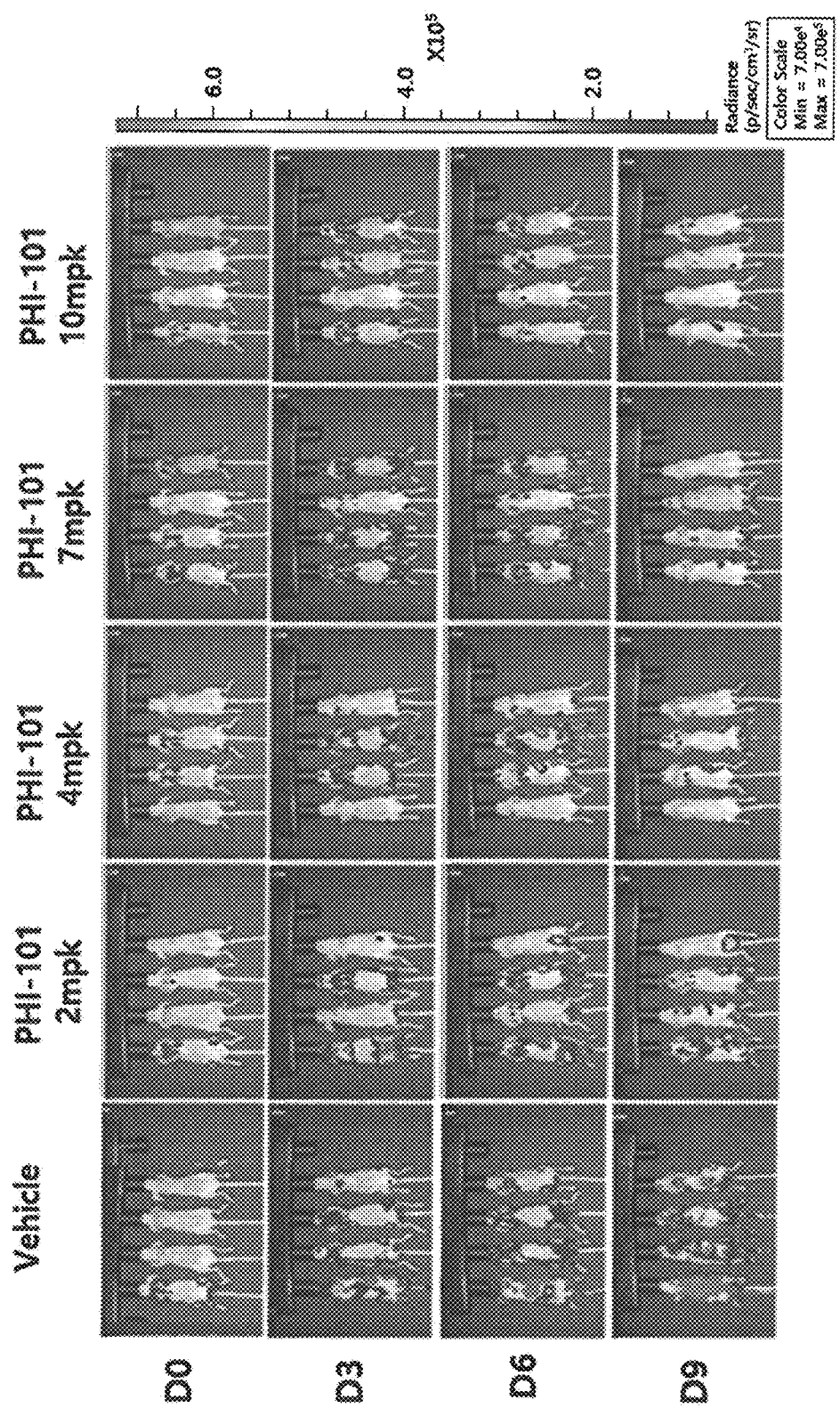

2,3,5-SUBSTITUTED THIOPHENE COMPOUND AS PROTEIN KINASE INHIBITOR

FIELD

The present invention relates to a novel 2,3,5-substituted thiophene compound having an inhibitory activity against kinases, an anticancer agent including the compound as an active ingredient, and a method for preparing the compound.

BACKGROUND

Protein kinase is an enzyme that catalyzes the phosphorylation of a hydroxyl group positioned at the tyrosine, serine, and threonine residues in proteins, and plays an important role in transducing growth factor signals that cause the growth, differentiation, and proliferation of cells.

In order to maintain the homeostasis of an organism, the in vivo signal transduction system needs to smoothly keep a balance between on and off. However, the mutation or overexpression of a specific protein kinase disrupts the signal transduction system in normal cells (usually in a state where the in vivo signal transduction is continued), thereby causing various diseases such as cancer, inflammation, metabolic disease, and disease of the brain. Examples of a representative protein kinase causing an abnormal cell growth disease include Raf, KDR, Fms, Tie2, SAPK2a, Ret, Abl, Abl (T315I), ALK, Aurora A, Bmx, CDK/cyclinE, Kit, Src, EGFR, EphAl, FGFR3, FLT3, Fms, IGF-1R, IKKb, IR, Itk, JAK2, KDR, Met, mTOR, PDGFRa, Plk1, Ret, Syk, Tie2, TrtB, and the like. Accordingly, through development of a compound having a selective inhibitory activity against a specific kinase among various protein kinases, studies on developing a target anticancer agent have been conducted.

Meanwhile, acute myeloid leukemia (AML) is one of the fatal blood diseases, and is a disease in which blood cells are continuously proliferated while being abnormally differentiated. Fms-Like tyrosine receptor kianse-3 (FLT3) is usually expressed in a hematopoietic stem cell and a progenitor cell, and is a receptor tyrosine kinase that plays an important role in hematopoiesis. FLT3 is one of the genes that are the most frequently mutated in patients with acute myeloid leukemia. In the case of about 25% of patients with AML, FLT3 genes are mutated into FLT3-ITD, and the FLT3-ITD mutation is one of the main factors that make early diagnosis difficult. In addition to the FLT3-ITD mutation, point mutations (D835Y, D835V, and D835F) of D835 amino acid in an activation loop have been reported. These mutations are discovered in about 10% of patients with AML, and induce overactivity of FLT3 by making the inactive state of FLT3 unstable. Overactive mutations such as the FLT3-ITD and FLT3-D835 point mutations cause AML by continuously increasing lower signals related to the differentiation and proliferation of blood cells. Accordingly, AML-inducing FLT3 mutations have been drug targets in the development of an AML target therapeutic agent.

As new drug candidate materials that adopt FLT3 developed up to now as a target, lestaurtinib, sunitinib, sorafenib, quizartinib, tandutinib, and the like have entered into clinical trials. The all candidate materials have been reported to show a strong activity against FLT-ITD mutant, however, quizartinib induced resistant mutants of FLT3-ITD+F691L, FLT3-ITD+D835Y, FLT3-ITD+F691L+D835Y (triple mutants), etc. Accordingly, there is an urgent need for developing a new compound which also has inhibitory activity against drug-resistant point mutation of FLT3 as a target therapeutic agent of acute myeloid leukemia (AML).

SUMMARY

Accordingly, an object of the present invention is to provide a novel 2,3,5-substituted thiophene compound having a protein kinase inhibitory activity.

Further, another object of the present invention is to provide a pharmaceutical composition useful for the treatment, prevention, and alleviation of cancer diseases, the pharmaceutical composition containing, as an active ingredient, a novel 2,3,5-substituted thiophene compound, a pharmaceutically acceptable salt thereof, a hydrate thereof, a solvate thereof, or an isomer thereof.

In addition, still another object of the present invention is to provide a method for preparing the aforementioned 2,3,5-substituted thiophene compound.

BRIEF DESCRIPTION OF THE DRAWINGS

FIG. 1(a) illustrates luminescent images of mice according to the compounds and dosages. Mice were imaged at day 3, 6, and 9 after oral compound administration. FIG. 1(b) illustrates ROI intensities according to the compounds and dosages which were measured at day 3, 6, and 9, and FIG. 1(c) illustrates the normalized ROI intensities according to the compounds and dosages.

FIG. 5(a)-FIG. 5(c) illustrate the bioluminescent in vivo efficacy study with low dosages (po, qd) for compounds using FLT3-ITD-F691L-D835Y Ba/F3 cells that have stable luciferase expression. FIG. 5(a) illustrates luminescent images of mice according to dosages. Mice were imaged at day 3, 6 and 9 after oral compound administration at dosage of 2, 4, 7, and 10 mg/kg. FIG. 5(b) illustrates ROI intensities according to dosages which were measured at day 3, 6, and 9, and FIG. 5(c) illustrates the normalized ROI intensities according to dosages.

DETAILED DESCRIPTION

Figure 1A:
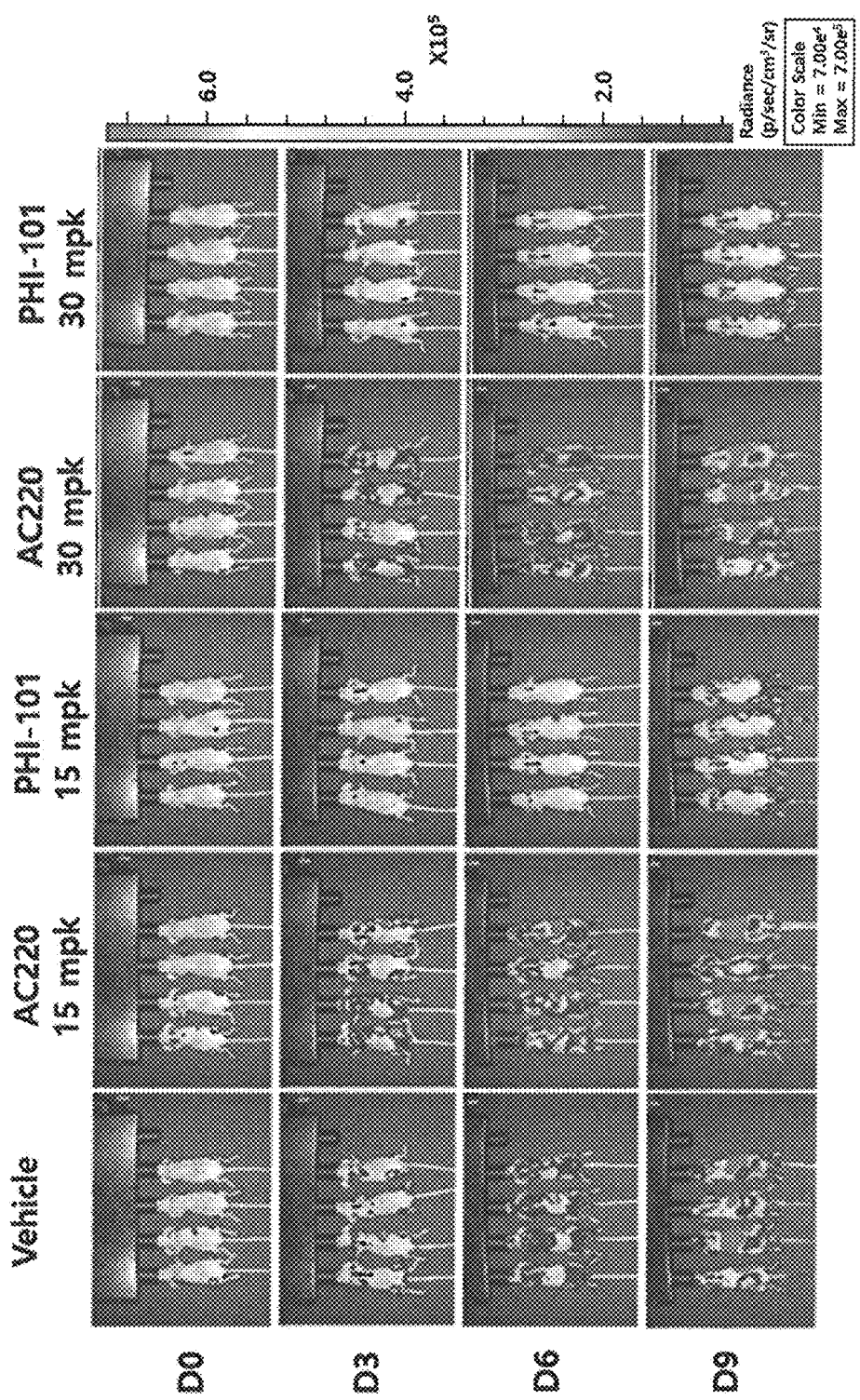
FIG. 1(a)-FIG. 1(c) illustrate the bioluminescent in vivo efficacy study (po, qd) using FLT3-ITD-F691L-D835Y Ba/F3 cells (Established in-house) that have stable luciferase expression.

In order to solve the aforementioned problems, the present invention is characterized by a compound selected from the group consisting of a 2,3,5-substituted thiophene compound represented by the following Chemical Formula 1, a pharmaceutically acceptable salt thereof, a hydrate thereof, a solvate thereof, and an isomer thereof.

[Chemical Formula 1]

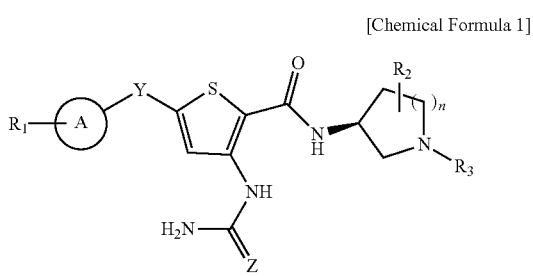

In Chemical Formula 1,

Z is O, S, or NH,

Y is a $C_{1-6}$ alkylene group; a $C_{2-6}$ alkenylene group; or a $C_{2-6}$ alkynylene group, A is a $C_{3-8}$ heterocycloalkyl group including one or two N atoms; a $C_{6-12}$ aryl group; or a $C_{3-12}$ heteroaryl group including one or two heteroatoms selected from N and S, $R_1$ is a substituent from the group consisting of halo, nitro, cyano, $C_{1-6}$ alkyl, $C_{1-6}$ haloalkyl, —$(CH_2)_m$—$C_{1-6}$ alkoxy (in this case, m is an integer from 1 to 6), —C(O)O—$C_{1-6}$ alkyl, —$S(O)_2$—$C_{1-6}$ alkyl, $C_{3-8}$ cycloalkyl, $C_{3-8}$ heterocycloalkyl including one or two heteroatoms selected from O and N, $C_{6-12}$ aryl, and $C_{3-8}$ heteroaryl including one or two heteroatoms selected from O and N, the number of substitutions of the substituent $R_1$ is 0 to 3, and when the substituent $R_1$ is heterocycloalkyl, aryl, or heteroaryl, the substituent $R_1$ may be unsubstituted or substituted with halo, $C_{1-6}$ alkyl, $C_{1-6}$ alkyl-C(O)— or $C_{1-6}$ alkyl-$S(O)_2$—, $R_2$ and $R_3$ are the same as or different from each other, and are a hydrogen atom; a halogen atom; a hydroxyl group; a —$C_{1-6}$ alkyl group; a $C_{3-8}$ cycloalkyl group; a $C_{1-6}$ hydroxyalkyl group; a $C_{1-6}$ haloalkyl group; a $C_{1-6}$ alkoxy group; a —C(O)—$C_{1-6}$ alkyl group; a —$S(O)_2$—$C_{1-6}$ alkyl group; or —$NR_4R_5$, $R_4$ and $R_5$ are the same as or different from each other, and are a hydrogen atom; a $C_{1-6}$ alkyl group; a $C_{3-8}$ cycloalkyl group; a $C_{3-8}$ heterocycloalkyl group including one or two heteroatoms selected from O and N; or a $C_{6-12}$ aryl group, and n is an integer from 1 to 3.

A 2,3,5-substituted thiophene compound according to the present invention is excellent in ability to inhibit activity of ANKK1, BLK, BUB1, CHEK1, CHEK2, CSF1R, CSK, DAPK1, PDGFRA, PDGFRB, PHKG1, SRC, YANK', DRAK1, DRAK2, FGR, FLT3, FLT4, FYN, HCK, PRKG2, SYK, TAK1, IRAK1, IRAK4, JAK3, KIT, MAP3K2, MAP3K3, MAP4K2, MAP4K4, RET, RIPK4, TNIK, TRKA, TRKB, YSK4, MEK1, MEK2, MEK5, MERTK, MINK, MKNK2, MLK1, MLK3, MST1, MST2, PAK4, PAK6, ULK1, and ULK2 protein kinases. Accordingly, the 2,3,5-substituted thiophene compound according to the present invention may be used for the purpose of treating, preventing, and alleviating cancer diseases caused by abnormal cell growth.

Examples of the cancer diseases which may be treated, prevented, and alleviated from the compound according to the present invention may include gastric cancer, lung cancer, liver cancer, colon cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, hematologic malignancy (including leukemia, multiple myeloma, and myelodysplastic syndrome), lymphoma (including Hodgkin's disease and non-Hodgkin's lymphoma), psoriasis, fibroadenoma, and the like.

In particular, the 2,3,5-substituted thiophene compound according to the present invention has an activity of suppressing proliferation of FLT3-ITD-holding leukemia cell line and Ba/F3 cell line, and exhibit excellent suppression activity against drug-resistant point mutants (F691L, D835Y, and F691L/D835Y) of FLT3, and thus is effective for the treatment of acute myeloid leukemia.

A pharmaceutically acceptable salt of the compound represented by Chemical Formula 1 according to the present invention may be prepared by a typical method in the art. The pharmaceutically acceptable salt need be less toxic to the human body and need not adversely affect biological activities and physical and chemical properties of a mother compound. The pharmaceutically acceptable salt consists of a pharmaceutically usable free acid, an acid addition salt of a basic compound of Chemical Formula 1, an alkali metal salt (a sodium salt, or the like), an alkaline earth metal (a potassium salt, or the like), an organic base addition salt of an organic salt and a carboxylic acid of Chemical Formula 1, and an amino acid addition salt. The free acid which may be used for the preparation of the pharmaceutically acceptable salt may be divided into an inorganic acid and an organic acid. As the inorganic acid, it is possible to use chloric acid, sulfuric acid, nitric acid, phosphoric acid, perchloric acid, bromic acid, and the like. As the organic acid, it is possible to use acetic acid, methanesulfonic acid, ethanesulfonic acid, p-toluenesulfonic acid, trifluoroacetic acid, fumaric acid, maleic acid, malonic acid, phthalic acid, succinic acid, lactic acid, citric acid, citric acid, gluconic acid, tartaric acid, salicylic acid, malic acid, oxalic acid, benzoic acid, embonic acid, aspartic acid, glutamic acid, and the like. Examples of an organic base which may be used for the preparation of the organic base addition salt include tris(hydroxymethyl)methylamine, dicyclohexylamine, and the like. Examples of an amino acid which may be used for the preparation of an amino acid addition base include a natural amino acid such as alanine and glycine.

The compound represented by Chemical Formula 1 according to the present invention includes not only the aforementioned pharmaceutically acceptable salt, but also all the hydrates and solvates thereof. The aforementioned pharmaceutically acceptable salt may be prepared by a typical method, for example, by dissolving the aforementioned basic compound of Chemical Formula 1 in a solvent which may be mixed with water, such as methanol, ethanol, acetone, and 1,4-dioxane, adding a free acid or a free base, and then crystallizing or recrystallizing the resulting mixture.

Further, the compound represented by Chemical Formula 1 according to the present invention may have one or more asymmetric centers, and in the case of the compound, an enantiomer or a diastereomer may be present. Accordingly, the present invention includes each isomer or an isomer mixture thereof. Different isomers may be separated or decomposed by a typical method, or any predetermined isomer may be obtained by a typical synthesis method, or a stereospecific or asymmetric synthesis.

In addition, the present invention includes radioactive derivatives of the compound represented by Chemical Formula 1 according to the present invention, and these radioactive compounds are useful in the biological research field.

A substituent used to define the compound according to the present invention will be described in more detail as follows.

The 'halo' or 'halogen atom' in the present invention is a term which may be interchanged and used, and means chloro, fluoro, bromo, and iodo.

The 'alkyl' in the present invention means a straight-chained, branched, or cyclic aliphatic saturated hydrocarbon group having 1 to 10 carbon atoms, preferably 1 to 6 carbon atoms, and more preferably 1 to 4 carbon atoms. Specific examples of the alkyl group include a methyl group, an ethyl group, a normal propyl group, an isopropyl group, a cyclopropyl group, a cyclopropylmethyl group, a normal butyl group, an isobutyl group, a tert-butyl group, a cyclobutyl group, a normal pentyl group, an isopentyl group, a neopentyl group, a tert-pentyl group, a cyclopentyl group, a normal hexyl group, an isohexyl group, a cyclohexyl group, a normal heptyl group, a normal octyl group, and the like.

The 'haloalkyl group' in the present invention includes all the straight-chained and branched carbon chains including 1 to 13 halogen atoms, such as fluoro, chloro, bromo, and iodo, and having 1 to 6 carbon atoms. Specific examples of the haloalkyl group include a fluoromethyl group, a trifluoromethyl group, a 1,2-dichloroethyl group, a 1,1-dichloroethyl group, a pentafluoroethyl group, and the like.

The 'alkoxyalkyl' in the present invention means an aliphatic saturated hydrocarbon group in which one or more alkoxys are bonded to the straight-chained or branched carbon chain defined above. Specific examples of the alkoxyalkyl group include a methoxymethyl group, a 2-methoxyethyl group, a 2-ethoxyethyl group, a 3-methoxypropyl group, a 1-methoxy-isopropyl group, a 2-methoxybutyl group, a 4-methoxybutyl group, a 2-methyl-2-methoxypropyl group, and the like.

The 'heterocycloalkyl' in the present invention means a saturated or partially saturated 5- to 10-membered aliphatic cyclic group including one or two heteroatoms selected from O and N. Specific examples of the heterocycloalkyl group include a tetrahydrofuranyl group, a 2,3-dihydrofuranyl group, a 2,5-dihydrofuranyl group, a pyrrolidinyl group, a 2,3-dihydropyrrolidinyl group, a 2,5-dihydropyrrolidinyl group, a tetrahydro-2H-pyranyl group, a 3,4-dihydro-2H-pyranyl group, a 4H-pyranyl group, a piperidinyl group, a 1,2,3,4-tetrahydropyridinyl group, a 1,4-dihydropyridinyl group, a piperazinyl group, an N-protected piperazinyl, a morpholino group, and the like. As an N-protecting group of piperazinyl, an alkyl group, an alkyl carbonyl group, and an alkyl sulfonyl group may be typically included.

The 'aryl' in the present invention means a monocyclic, bicyclic, or tricyclic aromatic hydrocarbon group having 6 to 12 carbon atoms. Specific examples of the aryl group include a phenyl group, a naphthalenyl group, and the like.

The 'heteroaryl' in the present invention means a monocyclic, bicyclic or tricyclic aromatic cyclic group including one or two heteroatoms selected from S and N and having 4 to 13 carbon atoms. Examples of the heteroaryl include a thiophenyl group, a pyrrolyl group, a pyrazolyl group, an imidazolyl group, a thiazolyl group, an isothiazolyl group, a pyridinyl group, a pyrazinyl group, a pyridazinyl group, a pyrimidinyl group, an indolyl group, an isoindolyl group, an indazolyl group, a benzimidazolyl group, a benzothiazolyl group, a benzisothiazolyl group, a quinolinyl group, an isoquinolinyl group, a phthalazinyl group, a quinazolinyl group, and the like.

The compound according to the present invention may be represented by the following Chemical Formula 1.

[Chemical Formula 1]

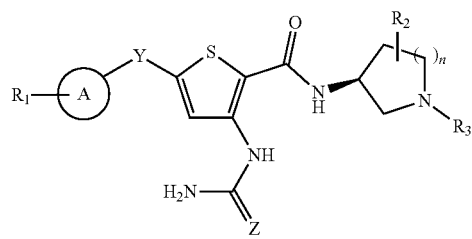

In Chemical Formula 1,

Z is O, S, or NH,

Y is a $C_{1-6}$ alkylene group; a $C_{2-6}$ alkenylene group; or a $C_{2-6}$ alkynylene group, A is a $C_{3-6}$ heterocycloalkyl group including one or two N atoms; a $C_{6-12}$ aryl group; or a $C_{3-12}$ heteroaryl group including one or two heteroatoms selected from N and S, $R_1$ is a substituent from the group consisting of halo, nitro, cyano, $C_{1-6}$ alkyl, $C_{1-6}$ haloalkyl, —$(CH_2)_m$—$C_{1-6}$ alkoxy (in this case, m is an integer from 1 to 6), —C(O)O—$C_{1-6}$ alkyl, —$S(O)_2$—$C_{1-6}$ alkyl, $C_{3-8}$ cycloalkyl, $C_{3-8}$ heterocycloalkyl including one or two heteroatoms selected from O and N, $C_{6-12}$ aryl, and $C_{3-8}$ heteroaryl including one or two heteroatoms selected from O and N, the number of substitutions of the substituent $R_1$ is 0 to 3, and when the substituent $R_1$ is heterocycloalkyl, aryl, or heteroaryl, the substituent $R_1$ may be unsubstituted or substituted with halo, $C_{1-6}$ alkyl, $C_{1-6}$ alkyl-C(O)— or $C_{1-6}$ alkyl-$S(O)_2$—, $R_2$ and $R_3$ are the same as or different from each other, and are a hydrogen atom; a halogen atom; a hydroxyl group; a $C_{1-6}$ alkyl group; a $C_{3-8}$ cycloalkyl group; a $C_{1-6}$ hydroxyalkyl group; a $C_{1-6}$ haloalkyl group; a $C_{1-6}$ alkoxy group; a —C(O)—$C_{1-6}$ alkyl group; a —$S(O)_2$—$C_{1-6}$ alkyl group; or —$NR_4R_5$, $R_4$ and $R_5$ are the same as or different from each other, and are a hydrogen atom; a $C_{1-6}$ alkyl group; a $C_{3-8}$ cycloalkyl group; a $C_{3-8}$ heterocycloalkyl group including one or two heteroatoms selected from O and N; or a $C_{6-12}$ aryl group, and n is an integer from 1 to 3.

The compound represented by Chemical Formula 1 is preferably a compound in which Z is O, Y is a $C_{1-6}$ alkylene group; or a $C_{2-6}$ alkynylene group, A is a piperidinyl group; a phenyl group; a thiophenyl group; an indazolyl group; a pyridinyl group; a pyrimidinyl group; a pyrazinyl group; or a pyrazolyl group, $R_1$ is 0 to 3 substituents selected from the group consisting of halo, nitro, cyano, $C_{1-6}$ alkyl, $C_{1-6}$ haloalkyl, —C(O)O—$C_{1-6}$ alkyl, —$S(O)_2$—$C_{1-6}$ alkyl, —$(CH_2)_m$—$C_{1-6}$ alkoxy (in this case, m is an integer from 1 to 6), tetrahydro-2Hpyranyl, piperidinyl, 4-(acetyl)-piperidinyl, 4-($C_{1-6}$ alkylsulfonyl)-piperidinyl, pyrrolidinyl, and morpholinyl, $R_2$ and $R_3$ are a hydrogen atom, and n is an integer from 1 to 3.

The compound represented by Chemical Formula 1 is more preferably a compound in which Z is O, Y is —$CH_2CH_2$—; or —C≡C—, $R_2$ and $R_3$ are a hydrogen atom, n is an integer from 1 to 3, and when A is a phenyl group, $R_1$ is 0 to 3 substituents selected from the group consisting of halo, nitro, cyano, methyl, ethyl, isopropyl, trifluoromethyl, methoxycarbonyl, and ethoxycarbonyl.

The compound represented by Chemical Formula 1 is more preferably a compound in which Z is O, Y is —CH₂CH₂—; or —C≡C—, R₂ and R₃ are a hydrogen atom, n is an integer from 1 to 3, and when A is a pyridinyl group, R₁ is 0 to 2 substituents selected from the group consisting of halo, trifluoromethyl, methyl, ethyl, isopropyl, pyrrolidinyl, piperidinyl, and morpholino.

The compound represented by Chemical Formula 1 is more preferably a compound in which Z is O, Y is —CH₂CH₂—; or —C≡C—, R₂ and R₃ are a hydrogen atom, n is an integer from 1 to 3, and when A is a pyrimidinyl group, R₁ is 0 to 2 substituents selected from the group consisting of halo.

The compound represented by Chemical Formula 1 is more preferably a compound in which Z is O, Y is —CH₂CH₂—; or —C≡C—, R₂ and R₃ are a hydrogen atom, n is an integer from 1 to 3, and when A is a pyrazolyl group, R₁ is a substituent which is 0 to 2 substituents selected from the group consisting of methyl, ethyl, isopropyl, methoxyethyl, etoxyethyl, tetrahydropyranyl, piperidinyl, 4-acetylpiperidinyl, and 4-methylsulfonylpiperidinyl.

The compound represented by Chemical Formula 1 is more preferably a compound in which Z is O, Y is —CH₂CH₂—; or —C≡C—, R₁, R₂, and R₃ are a hydrogen atom, n is an integer from 1 to 3, and A is a piperidinyl group; a phenyl group; an indazolyl group; a thiophenyl group; a pyrazolyl group; a pyrazinyl group; a pyridinyl group; or a pyrimidinyl group.

Further, the compound is more preferably a 2,3,5-substituted thiophene compound represented by the following Chemical Formula 1a.

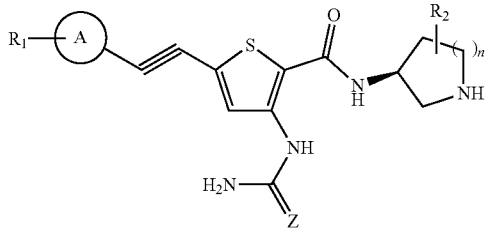

[Chemical Formula 1a]

In Chemical Formula 1a,

Z is O,

A is a piperidinyl group; a phenyl group; a thiophenyl group; an indazolyl group; a pyridinyl group; a pyrimidinyl group; a pyrazinyl group; or a pyrazolyl group, R₁ is 0 to 3 substituents selected from the group consisting of halo, nitro, cyano, $C_{1-6}$ alkyl, $C_{1-6}$ haloalkyl, —C(O)O—$C_{1-6}$ alkyl, —S(O)₂—$C_{1-6}$ alkyl, —(CH₂)$_m$—$C_{1-6}$ alkoxy (in this case, m is an integer from 1 to 6), tetrahydro-2Hpyranyl, piperidinyl, 4-(acetyl)-piperidinyl, 4-($C_{1-6}$ alkylsulfonyl)-piperidinyl, pyrrolidinyl, and morpholinyl, R₂ and R₃ are a hydrogen atom, and n is an integer from 1 to 3.

Further, more specific examples of the compound represented by Chemical Formula 1 are as follows:

1) Ethyl (S)-4-((5-(piperidin-3-ylcarbamoyl)-4-ureidothiophen-2-yl)ethynyl)benzoate;
2) (S)-5-(phenylethynyl)-N-(piperidin-3-yl)-3-ureidothiophene-2-carboxamide;
3) (S)—N-(piperidin-3-yl)-5-(pyridin-3-ylethynyl)-3-ureidothiophene-2-carboxamide;
4) (S)—N-(piperidin-3-yl)-5-(pyridin-4-ylethynyl)-3-ureidothiophene-2-carboxamide;
5) (S)-5-((3-nitrophenyl)ethynyl)-N-(piperidin-3-yl)-3-ureidothiophene-2-carboxamide;
6) (S)-5-((3-cyanophenyl)ethynyl)-N-(piperidin-3-yl)-3-ureidothiophene-2-carboxamide;
7) (S)-5-((4-nitrophenyl)ethynyl)-N-(piperidin-3-yl)-3-ureidothiophene-2-carboxamide;
8) (S)-5-((4-chlorophenyl)ethynyl)-N-(piperidin-3-yl)-3-ureidothiophene-2-carboxamide;
9) (S)-5-((4-fluorophenyl)ethynyl)-N-(piperidin-3-yl)-3-ureidothiophene-2-carboxamide;
10) (S)—N-(piperidin-3-yl)-5-(pyridin-2-ylethynyl)-3-ureidothiophene-2-carboxamide;
11) (S)-5-((4-cyanophenyl)ethynyl)-N-(piperidin-3-yl)-3-ureidothiophene-2-carboxamide;
12) (S)-5-((1H-indazol-3-yl)ethynyl)-N-(piperidin-3-yl)-3-ureidothiophene-2-carboxamide;
13) (S)-5-((6-fluoropyridin-3-yl)ethynyl)-N-(piperidin-3-yl)-3-ureidothiophene-2-carboxamide; 14) (S)-5-((3,4-difluorophenyl)ethynyl)-N-(piperidin-3-yl)-3-ureidothiophene-2-carboxamide;
15) (S)-5-((1-methyl-1H-pyrazol-4-yl)ethynyl)-N-(piperidin-3-yl)-3-ureidothiophene-2-carboxamide;
16) (S)—N-(piperidin-3-yl)-5-((4-(trifluoromethyl)phenyl)ethynyl)-3-ureidothiophene-2-carboxamide;
17) (S)—N-(piperidin-3-yl)-5-((6-(trifluoromethyl)pyridin-3-yl)ethynyl)-3-ureidothiophene-2-carboxamide;
18) Methyl (S)-4-((5-(piperidin-3-ylcarbamoyl)-4-ureidothiophen-2-yl)ethynyl)benzoate;
19) (S)-5-((6-chloropyridin-3-yl)ethynyl)-N-(piperidin-3-yl)-3-ureidothiophene-2-carboxamide;
20) (S)-5-((5-fluoropyridin-3-yl)ethynyl)-N-(piperidin-3-yl)-3-ureidothiophene-2-carboxamide;
21) (S)-5-((2-fluoropyridin-4-yl)ethynyl)-N-(piperidin-3-yl)-3-ureidothiophene-2-carboxamide;
22) (S)-5-((3-fluorophenyl)ethynyl)-N-(piperidin-3-yl)-3-ureidothiophene-2-carboxamide;
23) (S)-5-((1-(1-(methylsulfonyl)piperidin-4-yl)-1H-pyrazol-4-yl)ethynyl)-N-(piperidin-3-yl)-3-ureidothiophene-2-carboxamide;
24) (S)—N-(piperidin-3-yl)-5-(p-tolylethynyl)-3-ureidothiophene-2-carboxamide;
25) (S)-5-((3-bromo-4-cyanophenyl)ethynyl)-N-(piperidin-3-yl)-3-ureidothiophene-2-carboxamide;
26) (S)-5-((4-cyano-3-fluorophenyl)ethynyl)-N-(piperidin-3-yl)-3-ureidothiophene-2-carboxamide;
27) (S)-5-((3-fluoro-4-(trifluoromethyl)phenyl)ethynyl)-N-(piperidin-3-yl)-3-ureidothiophene-2-carboxamide;
28) (S)-5-((4-chloro-3-cyanophenyl)ethynyl)-N-(piperidin-3-yl)-3-ureidothiophene-2-carboxamide;
29) (S)-5-((2-chloropyrimidin-5-yl)ethynyl)-N-(piperidin-3-yl)-3-ureidothiophene-2-carboxamide;
30) (S)—N-(piperidin-3-yl)-5-(pyrazin-2-ylethynyl)-3-ureidothiophene-2-carboxamide;
31) (S)-5-((4-chloro-3-fluorophenyl)ethynyl)-N-(piperidin-3-yl)-3-ureidothiophene-2-carboxamide;
32) (S)-5-((3,5-difluorophenyl)ethynyl)-N-(piperidin-3-yl)-3-ureidothiophene-2-carboxamide;
33) (S)-5-((2-fluorophenyl)ethynyl)-N-(piperidin-3-yl)-3-ureidothiophene-2-carboxamide;
34) (S)-5-((2,3-difluorophenyl)ethynyl)-N-(piperidin-3-yl)-3-ureidothiophene-2-carboxamide;
35) (S)-5-((6-methylpyridin-3-yl)ethynyl)-N-(piperidin-3-yl)-3-ureidothiophene-2-carboxamide;
36) (S)—N-(piperidin-3-yl)-5-((6-(pyrrolidin-1-yl)pyridin-3-yl)ethynyl)-3-ureidothiophene-2-carboxamide;
37) (S)-5-((6-(piperidin-1-yl)pyridin-3-yl)ethynyl)-N-(piperidin-3-yl)-3-ureidothiophene-2-carboxamide;

38) (S)-5-((6-morpholinopyridin-3-yl)ethynyl)-N-(piperidin-3-yl)-3-ureidothiophene-2-carboxamide;
39) 5-((1-methyl-1H-pyrazol-4-yl)ethynyl)-N-(pyrrolidin-3-yl)-3-ureidothiophene-2-carboxamide;
40) 5-((3-fluorophenyl)ethynyl)-N-(pyrrolidin-3-yl)-3-ureidothiophene 2-carboxamide;
41) (S)—N-(azepan-3-yl)-5-((1-methyl-1H-pyrazol-4-yl)ethynyl)-3-ureidothiophene-2-carboxamide;
42) (S)-5-((1H-pyrazol-4-yl)ethynyl)-N-(azepan-3-yl)-3-ureidothiophene-2-carboxamide;
43) (S)—N-(azepan-3-yl)-5-((1-ethyl-1H-pyrazol-4-yl)ethynyl)-3-ureidothiophene-2-carboxamide;
44) (S)—N-(azepan-3-yl)-5-((1-isopropyl-1H-pyrazol-4-yl)ethynyl)-3-ureidothiophene-2-carboxamide;
45) (S)—N-(azepan-3-yl)-5-((1-(2-methoxyethyl)-1H-pyrazol-4-yl)ethynyl)-3-ureidothiophene-2-carboxamide;
46) (S)—N-(azepan-3-yl)-5-((1-(tetrahydro-2H-pyran-4-yl)-1H-pyrazol-4-yl)ethynyl)-3-ureidothiophene-2-carboxamide;
47) (S)—N-(azepan-3-yl)-5-((1-(1-methylsulfonyl)piperidin-4-yl)-1H-pyrazol-4-yl)ethynyl)-3-ureidothiophene-2-carboxamide;
48) (S)—N-(azepan-3-yl)-5-(thiophen-3-ylethynyl)-3-ureidothiophene-2-carboxamide;
49) (S)-5-((1-(1-(acetylpiperidin-4-yl)-1H-pyrazol-4-yl)ethynyl)-N-(azepan-3-yl)-3-ureidothiophene-2-carboxamide;
50) (S)—N-(azepan-3-yl)-5-((3-fluorophenyl)ethynyl)-3-ureidothiophene-2-carboxamide;
51) 5-(2-((1-methyl-1H-pyrazol-4-yl)ethyl)-N-(pyrrolidin-3-yl)-3-ureidothiophene-2-carboxamide; 52) (S)—N-(azepan-3-yl)-5-(2-(1-methyl-1H-pyrazol-4-yl)ethyl)-3-ureidothiophene-2-carboxamide;
53) (S)-5-(3-fluorophenethyl)-N-(piperidin-3-yl)-3-ureidothiophene-2-carboxamide;
54) (S)—N-(azepan-3-yl)-5-(3-fluorophenethyl)-3-ureidothiophene-2-carboxamide; or
55) 5-(3-fluorophenethyl)-N-(pyrrolidin-3-yl)-3-ureidothiophene-2-carboxamide;

Meanwhile, the present invention is characterized by a method for preparing the compound represented by Chemical Formula 1. The preparation method according to the present invention will be described in detail as follows.

Preparation Method 1

According to a preparation method according to the following Scheme 1, the compound represented by Chemical Formula 1 may be prepared by performing a preparation process of 6 steps using a compound represented by the following Chemical Formula 2 as a starting material.

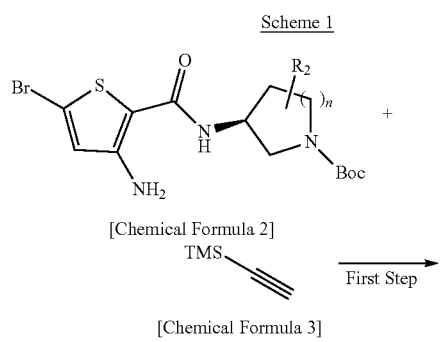

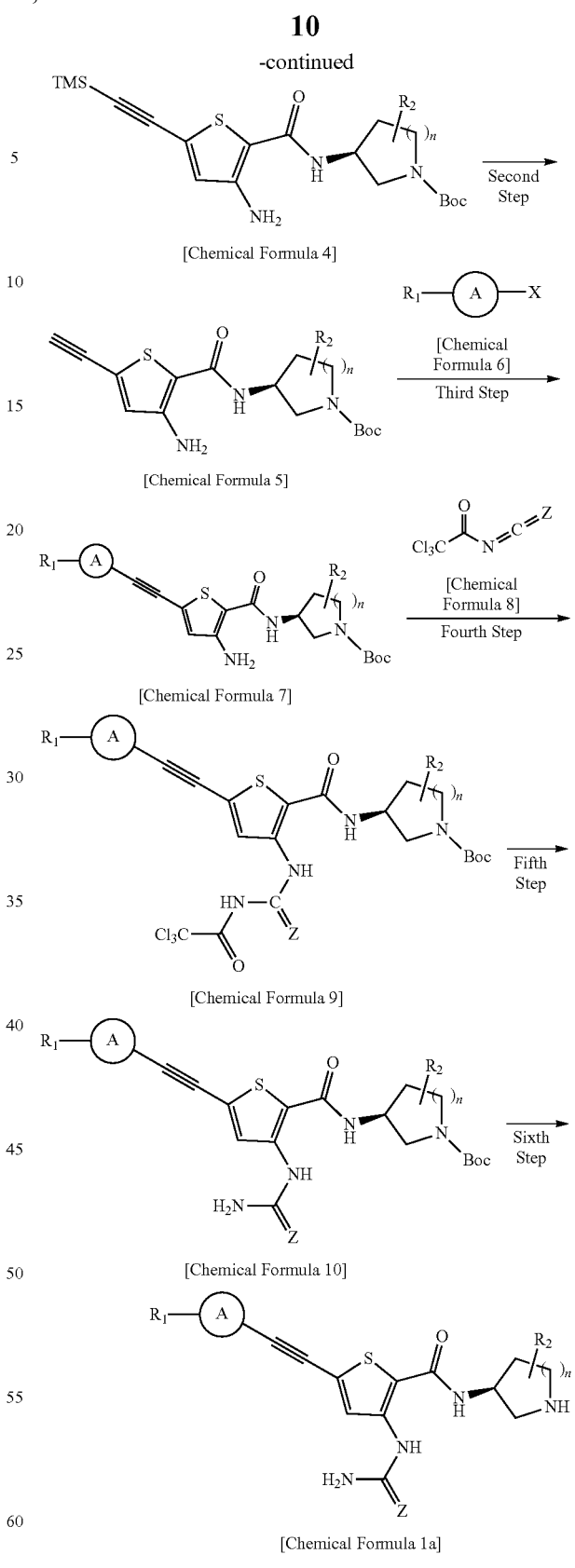

(In Scheme 1, $R_1$, $R_2$, A, and n are the same as those defined in Chemical Formula 1, respectively, X indicates a halogen atom, TMS indicates a trimethylsilyl group, and Boc indicates a tert-butoxycarbonyl group.)

The preparation method according to Scheme 1 will be described for each step in more detail as follows.

The reaction in the first step is a process of introducing an acetylene group into a C5 position of thiophene by allowing the 2-(Boc protected carboxamido)-3-amino-5-bromo-thiophene represented by Chemical Formula 2 to react with the trimethylsilylacetylene represented by Chemical Formula 3.

Specifically, the reaction in the first step is performed by heating the mixture to a temperature of 50° C. to 90° C. under a condition in which triphenylphosphine palladium (Pd(PPh$_3$)$_4$) and copper iodide (CuI) are added and in the presence of an amine base. In this case, the amine base may be selected from mono-, di-, or tri-$C_{1-6}$ alkylamine, and the like, and preferably, trialkylamine such as triethylamine (TEA) and diisopropylethylamine (DIPEA) may be used. As a reaction solvent, a typical organic solvent may be used, and the Examples of the present invention specifically exemplify examples in which dimethylformamide (DMF) is usually used, but the solvent of the present invention is not limited thereto.

The reaction in the second step is a process of desorbing a trimethylsilyl (TMS) protecting group from the compound represented by Chemical Formula 4.

Specifically, the reaction in the second step is performed under a room temperature condition by using an inorganic base. In this case, the inorganic base may be selected from a hydroxide, an oxide, a carbonate, a sulfate, and the like of an alkali metal or alkaline earth metal, and preferably, a carbonate of an alkali metal, such as potassium carbonate may be used. The reaction may be performed under a mixed solvent of alcohol and tetrahydrofuran as the reaction solvent, and as the alcohol, methanol or ethanol may be representatively used. The mixed solvent may be used by appropriately mixing alcohol and tetrahydrofuran within a volume ratio range of 1:2 to 2:1.

The reaction in the third step is a process of introducing an R group by allowing the compound represented by Chemical Formula 5 to react with the halide compound represented by Chemical Formula 6.

Specifically, the reaction in the third step is performed by heating the mixture to a temperature of 70° C. to 120° C. under a condition in which triphenylphosphine palladium (Pd(PPh$_3$)$_4$) and copper iodide (CuI) are added and in the presence of an amine base. In this case, the amine base may be selected from mono-, di-, or tri-$C_{1-6}$ alkylamine, and the like, and preferably, trialkylamine such as triethylamine and diisopropylethylamine may be used. As a reaction solvent, a typical organic solvent may be used, and the Examples of the present invention specifically exemplify examples in which dimethylformamide (DMF) is usually used, but the solvent of the present invention is not limited thereto.

The reaction in the fourth step is a process of introducing a urea group into a C3 position of thiophene by allowing the compound represented by Chemical Formula 7 to react with the compound represented by Chemical Formula 8.

Specifically, the reaction in the fourth step is performed at room temperature. As a reaction solvent, a typical organic solvent may be used, and the Examples of the present invention specifically exemplify examples in which tetrahydrofuran (THF) is usually used, but the solvent of the present invention is not limited thereto.

The reaction in the fifth step is a process of removing a trichloroacetyl(F$_3$CC(O)—) group from the compound represented by Chemical Formula 9.

Specifically, the reaction in the fifth step is performed at room temperature in the presence of an amine base. In this case, the amine base may be selected from mono-, di-, or tri-$C_{1-6}$ alkylamine, and the like, and preferably, trialkylamine such as triethylamine and diisopropylethylamine may be used. As a reaction solvent, a typical organic solvent may be used, and the Examples of the present invention specifically exemplify examples in which an alcohol solvent such as methanol is usually used, but the solvent of the present invention is not limited thereto.

The reaction in the sixth step is a process of desorbing a tert-butoxycarbonyl (Boc) group from the compound represented by Chemical Formula 10.

Specifically, the reaction in the sixth step is performed at room temperature by using trifluoroacetic acid (TFA). As a reaction solvent, a typical organic solvent may be used, and the Examples of the present invention specifically exemplify examples in which dichloromethane (MC) is usually used, but the solvent of the present invention is not limited thereto.

Preparation Method 2

According to a preparation method according to the following Scheme 2, the compound represented by Chemical Formula 1 may be prepared by performing a preparation process of 4 steps using a compound represented by the following Chemical Formula 2 as a starting material.

Scheme 2

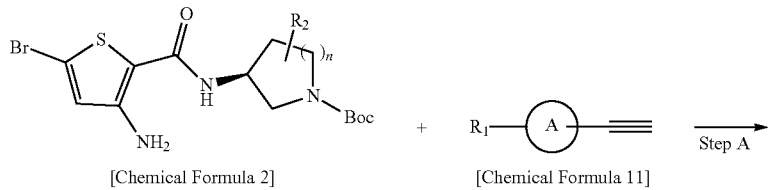

[Chemical Formula 2]     [Chemical Formula 11]     Step A

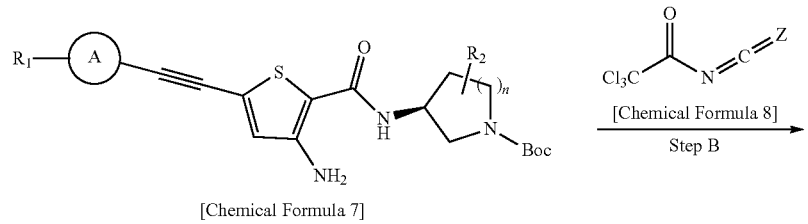

[Chemical Formula 7]

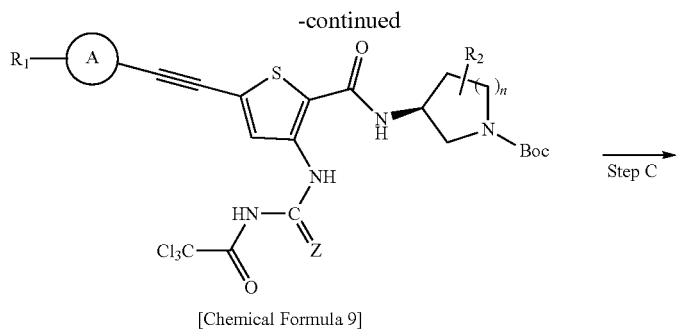

[Chemical Formula 9]

[Chemical Formula 10]

[Chemical Formula 1a]

(In Scheme 2, $R_1$, $R_2$, A, and n are the same as those defined in Chemical Formula 1, respectively, and Boc indicates a tert-butoxycarbonyl group.)

The preparation method according to Scheme 2 will be described for each step in more detail as follows.

The reaction in Step A is a process of introducing an acetylene group into a C5 position of thiophene by allowing the 2-(Boc protected carboxamido)-3-amino-5-bromo-thiophene represented by Chemical Formula 2 to react with the acetylene compound represented by Chemical Formula 11.

Specifically, the reaction in Step A is performed by heating the mixture to a temperature of 60° C. to 120° C. under a condition in which triphenylphosphine palladium $(Pd(PPh_3)_4)$ and copper iodide (CuI) are added and in the presence of an amine base. In this case, the amine base may be selected from mono-, di-, or tri-$C_{1-6}$ alkylamine, and the like, and preferably, a trialkylamine such as triethylamine and diisopropylethylamine may be used. As a reaction solvent, a typical organic solvent may be used, and the Examples of the present invention specifically exemplify examples in which dimethylformamide (DMF) is usually used, but the solvent of the present invention is not limited thereto.

The reaction in Step B is a process of introducing a urea group into a C3 position of thiophene by allowing the compound represented by Chemical Formula 7 to react with the compound represented by Chemical Formula 8.

Specifically, the reaction in Step B is performed at room temperature. As a reaction solvent, a typical organic solvent may be used, and the Examples of the present invention specifically exemplify examples in which tetrahydrofuran (THF) is usually used, but the solvent of the present invention is not limited thereto.

The reaction in Step C is a process of removing a trichloroacetyl($F_3CC(O)$—) group from the compound represented by Chemical Formula 9.

Specifically, the reaction in Step C is performed at room temperature in the presence of an amine base. In this case, the amine base may be selected from mono-, di-, or tri-$C_{1-6}$ alkylamine, and the like, and preferably, trialkylamine such as triethylamine and diisopropylethylamine may be used. As a reaction solvent, a typical organic solvent may be used, and the Examples of the present invention specifically exemplify examples in which an alcohol solvent such as methanol is usually used, but the solvent of the present invention is not limited thereto.

The reaction in Step D is a process of desorbing tert-butoxycarbonyl (Boc) from the compound represented by Chemical Formula 10.

Specifically, the reaction in Step D is performed at room temperature by using trifluoroacetic acid (TFA). As a reaction solvent, a typical organic solvent may be used, and the Examples of the present invention specifically exemplify examples in which dichloromethane (MC) is usually used, but the solvent of the present invention is not limited thereto.

Preparation Method 3

According to a preparation method according to the following Scheme 3, a compound represented by the following Chemical Formula 1a may be converted into a —HC═CH— or —$CH_2$—$CH_2$— group by subjecting an acetylene group in the compound represented by Chemical Formula 1a to reduction reaction.

Scheme 3

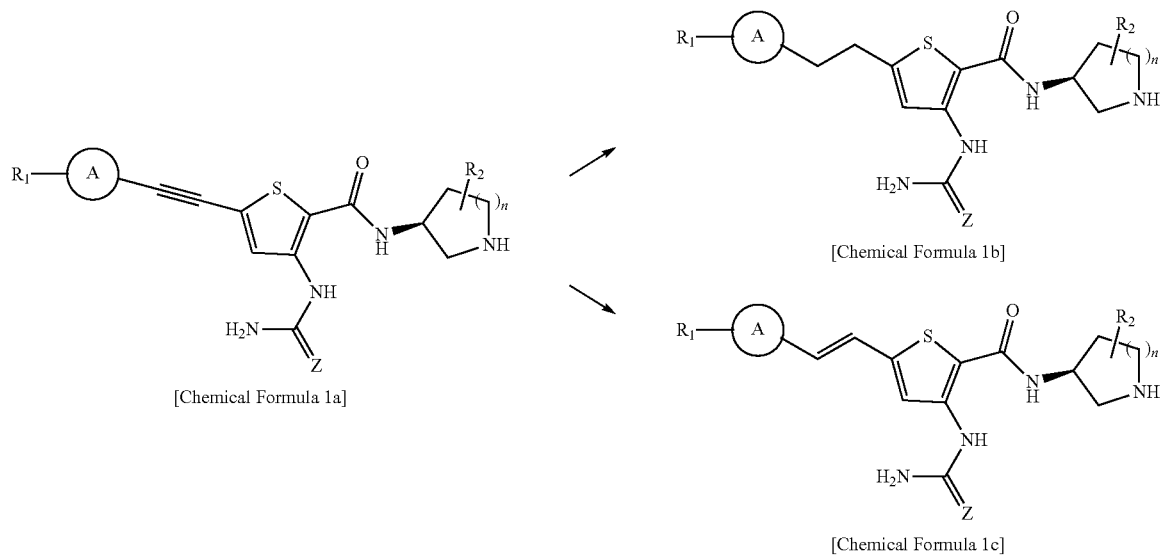

[Chemical Formula 1a]

[Chemical Formula 1b]

[Chemical Formula 1c]

(In Scheme 3, $R_1$, $R_2$, A, and n are the same as those defined in Chemical Formula 1, respectively.)

The reduction reaction according to Scheme 3 may be performed at room temperature while flowing a hydrogen gas under a palladium (Pd) catalyst. As a reaction solvent, a typical organic solvent may be used, and the Examples of the present invention specifically exemplify examples in which an alcohol solvent such as methanol is usually used, but the solvent of the present invention is not limited thereto.

Preparation Method 4

The compound represented by Chemical Formula 2 used as a staring material in Scheme 1 and Scheme 2 may be prepared by a preparation method according to the following Scheme 4.

Scheme 4

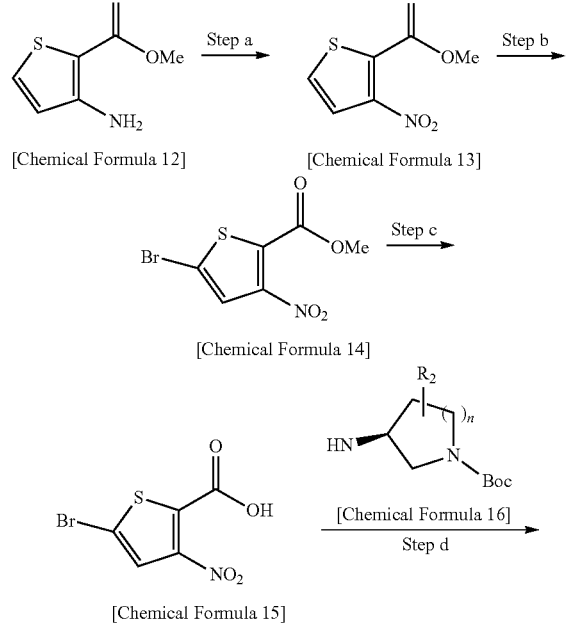

[Chemical Formula 12]

[Chemical Formula 13]

[Chemical Formula 14]

[Chemical Formula 15]

[Chemical Formula 16]

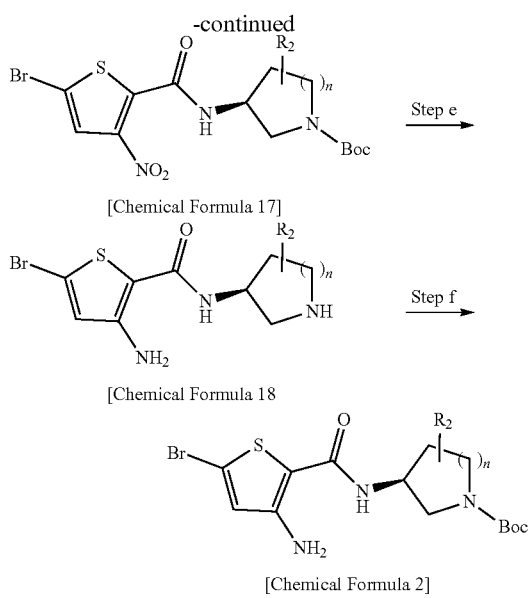

[Chemical Formula 17]

[Chemical Formula 18]

[Chemical Formula 2]

(In Scheme 4, $R_2$ and n are the same as those defined in Chemical Formula 1, respectively.)

The preparation method according to Scheme 4 will be described for each step in more detail as follows.

The reaction in Step a is a process of nitrifying an amine group of the thiophene compound represented by Chemical Formula 12.

Specifically, the reaction in Step a is performed at room temperature at a temperature of −20° C. to 0° C. by using sodium nitrate ($NaNO_2$), hydrochloric acid (HCl), and sodium tetrafluoroborate ($NaBF_4$), and as a reaction solvent, water may be used. And then, an aqueous diazonium salt solution prepared by allowing copper and sodium nitrate to react with each other may be added to the reaction solution, and the thiophene compound represented by Chemical Formula 13 in which a nitro group is substituted may be prepared by allowing the resulting mixture to react at room temperature.

The reaction in Step b is a process of introducing a bromo atom into a C5 position of the thiophene compound represented by Chemical Formula 13.

Specifically, the reaction in Step b is performed at room temperature by using a brominating reagent such as N-bromosuccinimide, trifluoroacetic acid (TFA), and sulfuric acid.

The reaction in Step c is a process of converting methoxycarbonyl (—COOMe) at a C1 position of the thiophene compound represented by Chemical Formula 14 into carboxylic acid (—COOH) by hydrolyzing the methoxycarbonyl. Specifically, the reaction in Step c is performed at room temperature by using an alkali metal hydroxide including sodium hydroxide. The reaction may be performed under a mixed solvent of alcohol and tetrahydrofuran as the reaction solvent, and as the alcohol, methanol or ethanol may be representatively used. The mixed solvent may be used by appropriately mixing alcohol and tetrahydrofuran within a volume ratio range of 1:2 to 2:1.

The reaction in Step d is a process of introducing an amido group into a C1 position of thiophene by allowing the thiophene compound represented by Chemical Formula 15 to react with the amine compound represented by Chemical Formula 16.

Specifically, the reaction in Step d is performed at a temperature of 30° C. to 60° C. in the presence of 1-[bis (dimethylamino)methylene]-1H-1,2,3-triazolo[4,5-b]pyridinum 3-oxide hexafluorophosphate (HATU) and an amine base. In this case, the amine base may be selected from mono-, di-, or tri-$C_{1-6}$ alkylamine, and the like, and preferably, trialkylamine such as triethylamine and diisopropylethylamine may be used. As a reaction solvent, a typical organic solvent may be used, and the Examples of the present invention specifically exemplify examples in which dimethylformamide (DMF) is usually used, but the solvent of the present invention is not limited thereto.

The reaction in Step e is a process of subjecting a nitro group at a C3 position of the thiophene compound represented by Chemical Formula 17 to amination.

Specifically, the reaction in Step e is performed at a temperature of 30° C. to 60° C. by using tin chloride ($SnCl_2$), sodium nitrate ($NaNO_2$), hydrochloric acid (HCl), and sodium tetrafluoroborate ($NaBF_4$). As a reaction solvent, a typical organic solvent may be used, and the Examples of the present invention specifically exemplify examples in which ethyl acetate (EA) is usually used, but the solvent of the present invention is not limited thereto.

The reaction in Step f is a process of protecting an amine group of a hetero ring at a C2 position of the thiophene compound represented by Chemical Formula 18.

Specifically, in the reaction in Step e, tert-butoxycarbonyl (Boc) is introduced as an amine protecting group. That is, the thiophene compound represented by Chemical Formula 17 and di-tert-butyl dicarbonate are allowed to react with each other at room temperature in the presence of an amine base. In this case, the amine base may be selected from mono-, di-, or tri-$C_{1-6}$ alkylamine, and the like, and preferably, trialkylamine such as triethylamine and diisopropylethylamine may be used. As a reaction solvent, a typical organic solvent may be used, and the Examples of the present invention specifically exemplify examples in which dichloromethane (MC) is usually used, but the solvent of the present invention is not limited thereto.

Meanwhile, the present invention provides a pharmaceutical composition for the treatment, prevention, and alleviation of cancer diseases, the pharmaceutical composition including, as an active ingredient, the compound represented by Chemical Formula 1, a pharmaceutically acceptable salt thereof, a solvate thereof, and a hydrate thereof. Examples of the cancer diseases which may be treated and prevented from the compound according to the present invention may include gastric cancer, lung cancer, liver cancer, colon cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, hematologic malignancy (including leukemia, multiple myeloma, and myelodysplastic syndrome), lymphoma (including Hodgkin's disease and non-Hodgkin's lymphoma), psoriasis, fibroadenoma, and the like.

In particular, the compound represented by Chemical Formula 1 suppresses proliferation of FLT3-ITD-holding leukemia cell line and Ba/F3 cell line, and simultaneously exhibits excellent suppression activity against FLT3 point mutants, for example, gatekeeper mutants, D835 mutants, and ITD mutants. Accordingly, the compound represented by Chemical Formula 1 may be used particularly usefully as a prophylactic agent or a therapeutic agent for acute myeloid leukemia.

The pharmaceutical composition of the present invention may be formulated into a typical preparation in the pharmaceutical field, for example, a preparation for oral administration or parenteral administration, such as a tablet, a capsule, a troche, a liquid, or a suspension by containing, as an active ingredient, the compound represented by Chemical Formula 1, a pharmaceutically acceptable salt thereof, a solvate thereof, or a hydrate thereof, and adding a typical, non-toxic pharmaceutically acceptable carrier, a reinforcing agent, an excipient, and the like thereto.

Examples of the excipient which may be used for the pharmaceutical composition of the present invention include a sweetening agent, a binding agent, a dissolving agent, a dissolution aid, a wetting agent, an emulsifying agent, an isotonic agent, an adsorbent, a disintegrant, an antioxidant, a preservative, a lubricant, a filler, a fragrance agent, and the like. Examples thereof include lactose, dextrose, sucrose, mannitol, sorbitol, cellulose, glycine, silica, talc, stearic acid, sterin, magnesium stearate, magnesium aluminum silicate, starch, gelatin, tragacanth gum, argininic acid, sodium alginate, methyl cellulose, sodium carboxymethyl cellulose, agar, water, ethanol, polyethylene glycol, polyvinylpyrrolidone, sodium chloride, calcium chloride, orange essence, strawberry essence, vanilla flavor, and the like.

Further, the dose of the compound according to the present invention administered to the human body may vary depending on the age, body weight, gender, administration form, health status, and level of disease of a patient, and is generally 0.01 to 1,000 mg/day based on an adult patient having a body weight of 70 kg, and the compound may be administered in divided doses once to several times a day at predetermined time intervals depending on the judgment of a doctor or a pharmacist.

The present invention as described above will be described in more detail with reference to the following Examples, Experimental Examples, and Preparation Examples, but the following Examples, Experimental Examples, and Preparation Examples only illustrate the present invention, and the scope of the present invention is not limited thereby.

EXAMPLES

The compounds synthesized in the Examples of the present invention were purified or subjected to structural analysis under the following HPLC conditions.

(1) HPLC Condition 1 for Structural Analysis
Elution Solvent A: 0.1% trifluoroacetic acid (TFA)/Water
Elution Solvent B: $CH_3CN$
Column: YMC-Park Pro C18, 150×4.6 mm column
Elution Condition: Elution for 7 minutes while varying the concentration of Solvent B from 5 to 100% at a moving rate of 1.0 mL/min.

(2) HPLC Condition 2 for Structural Analysis
Elution Solvent A: 0.1% trifluoroacetic acid (TFA)/Water
Elution Solvent B: $CH_3CN$
Column: Kinetex 2.6 u Biphenyl 100 A, New column 100×2.1 mm Column
Elution Condition: Elution for 4.5 minutes while varying the concentration of Solvent B from 5 to 100% at a moving rate of 1.2 mL/min.

(3) HPLC Conditions for Purification
Elution Solvent A: 0.1% trifluoroacetic acid (TFA)/Water
Elution Solvent B: $CH_3CN$
Column: Luna 10 u C18, 250×21.2 mm column Preparation Example 1. Preparation of tert-butyl (S)-3-(3-amino-5-bromothiophene-2-carboxamido)piperidine-1-carboxylate

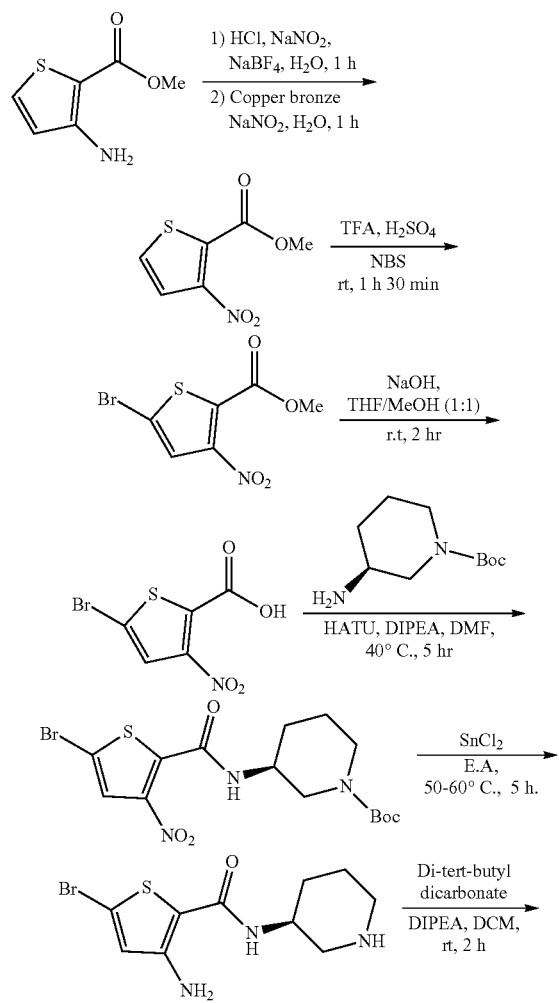

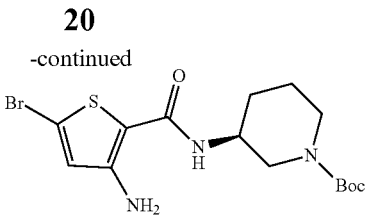

Step 1. Preparation of Methyl 3-nitrothiophene-2-carboxylate

After a suspension was prepared by putting concentrated hydrochloric acid (26 mL, 842 mmol) into methyl 3-aminothiophene-2-carboxylate (15.7 g, 100 mmol), water (24 mL) was added thereto, and the resulting mixture was stirred at room temperature for 45 minutes. After the reaction mixture was cooled to −10° C., a solution of sodium nitrate ($NaNO_2$; 7.2 g, 110 mmol) dissolved in water (16 mL) was slowly added thereto for 20 minutes. When the addition was completed, the reaction mixture was stirred at 0° C. for 1 hour, and then a solution of tetrafluoroborate (16 g, 150 mmol) dissolved in water (32 mL) was added thereto. The produced salt was filtered, washed sequentially with an iced 5% aqueous sodium tetrafluoroborate solution, ethanol, and diethyl ether in this order, and then dried. Subsequently, after an activated copper powder (copper bronze, 16 g, 300 mmol) was added to a solution of sodium nitrate ($NaNO_2$; 80 g, 1,160 mmol) dissolved in water (160 mL), a diazonium salt dissolved in water (80 mL) was prepared while vigorously stirring the resulting mixture, and then slowly added to the reaction solution at room temperature for 1 hour or more. After the addition was completed, the mixture was further stirred for 1 hour, and then diluted with ethyl acetate and filtered through Celite. An organic layer was taken by separating an aqueous layer and the organic layer, and the aqueous layer was extracted again with ethyl acetate. The organic layer was collected, dried over sodium sulfate, concentrated, and then purified with MPLC to obtain a white solid target compound (15.1 g, 72%).
$^1$H NMR (400 MHz, DMSO-$d_6$) δ 8.06 (d, 2H), 3.86 (s, 3H).

Step 2. Preparation of Methyl 5-bromo-3-nitrothiophene-2-carboxylate

After concentrated sulfuric acid (17.1 mL, 321 mmol) was added to a mixture solution of trifluoroacetic acid (86 mL, 1,122 mmol) and methyl 3-nitrothiophene-2-carboxylate (30 g, 160 mmol), N-bromosuccinimide (NBS; 31.4 g, 176 mmol) was slowly added thereto at 0° C. for more than 40 minutes. After the reaction mixture solution was stirred for 30 minutes, the temperature was increased to room temperature, and the reaction mixture solution was poured into iced water. The produced precipitate was filtered and recovered, and then washed with iced water and dried to obtain a yellow solid target compound (34 g, 80%).
$^1$H NMR (400 MHz, DMSO-$d_6$) δ 7.99 (s, 1H), 3.85 (s, 3H).

Step 3. Preparation of 5-bromo-3-nitrothiophene-2-carboxylic acid

After methyl 5-bromo-3-nitrothiophene-2-carboxylate (10 g, 37.6 mmol) was dissolved in a mixture solution of tetrahydrofuran/methanol (1:1, 40 mL), a 1N sodium hydroxide solution (41.3 mL, 41.3 mmol) was added dropwise thereto, and then the resulting mixture was stirred at room temperature for 1 hour. After the pH was adjusted to 5 by adding an aqueous 2N hydrochloric acid solution to the reaction mixture, the mixture was extracted with ethyl acetate. The extracted organic layer was dried over magnesium sulfate and concentrated to obtain a grey solid target compound (8.0 g, 84%).

$^1$H NMR (400 MHz, DMSO-$d_6$) δ 7.93 (s, 1H).

Step 4. Preparation of tert-butyl (S)-3-(5-bromo-3-nitrothiophene-2-carboxamido)piperidine-1-carboxylate (S)-1-Boc-3-aminopiperidine (3.57 g, 17.85 mmol) was added dropwise to a solution in which 5-bromo-3-nitrothiophene-2-carboxylic acid (4.5 g, 17.85 mmol), 1-[bis(dimethylamino)methylene]-1H-1,2,3-triazolo[4,5-b]pyridinum 3-oxide hexafluorophosphate (HATU; 20.37 g, 53.6 mmol), diisopropylethylamine (DIPEA; 11.54 g, 89 mmol), and dimethylformamide (50 mL) were mixed, and the resulting mixture was stirred at 40° C. for 15 hours. An organic layer was collected by extracting the reaction mixture with ethyl acetate and a saturated aqueous sodium bicarbonate solution. The collected organic layer was washed with brine solution, dried over sodium sulfate, concentrated under reduced pressure, and purified with MPLC to obtain a yellow solid target compound (6.2 g, 80%).

$^1$H NMR (400 MHz, DMSO-$d_6$) δ 8.86 (d, 1H), 7.88 (s, 1H), 3.82 (m, 1H), 2.94 (m, 2H), 1.85 (m, 1H), 1.67 (m, 1H), 1.40 (s, 9H), 1.39 (m, 4H).

Step 5. Preparation of (S)-3-amino-5-bromo-N-(piperidin-3-yl)thiophene-2-carboxamide Tert-butyl (S)-3-(5-bromo-3-nitrothiophene-2-carboxamido)piperidine-1-carboxylate (8.6 g, 19.8 mmol) and SnCl$_2$·2H$_2$O (22.34 g, 99 mmol) were dissolved in ethyl acetate (30 mL), and then the resulting mixture was stirred at 55° C. for 5 hours. After the temperature of the reaction solution was lowered to room temperature, an ammonium hydroxide solution was added thereto until the pH became 5. The pH was adjusted to 7 by adding anhydrous sodium carbonate to the reaction mixture. The reaction mixture was filtered with Celite and rubbed several times with ethyl acetate. The filtrate was concentrated under reduced pressure to obtain a target compound (5.0 g, 83%), and the target compound was used in the next reaction without purification.

MS (m/z): 304[M+1]

Step 6. Preparation of tert-butyl (S)-3-(3-amino-5-bromothiophene-2-carboxamido)piperidine-1-carboxylate (S)-3-amino-5-bromo-N-(piperidin-3-yl)thiophene-2-carboxamide (5.0 g, 16.4 mmol) was dissolved in dichloromethane (25 mL), and then diisopropylethylamine (DIPEA; 6.37 g, 49.3 mmol) and di-tert-butyl dicarbonate (3.95 g, 18.1 mmol) were sequentially added dropwise thereto. The reaction mixture was stirred at room temperature for 2 hours, and then extracted by using ethyl acetate and water. The organic layer was washed with brine solution, dried over sodium sulfate, filtered, and then concentrated under reduced pressure to obtain a target compound (6.4 g, 96%).

MS (m/z): 404[M+1].

Preparation Example 2. Preparation of tert-butyl 3-(3-amino-5-bromothiophene-2-carboxamido)pyrrolidine-1-carboxylate

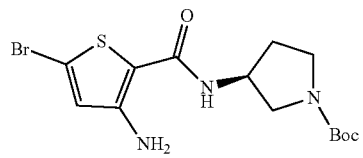

A target compound was obtained by repeating the same procedure as in Preparation Example 1, except that in Step 4 of Preparation Example 1, 1-Boc-3-aminopyrrolidine was used instead of (S)-1-Boc-3-aminopiperidine.

MS (m/z): 390[M+1].

Preparation Example 3. Preparation of tert-butyl (S)-3-(3-amino-5-bromothiophene-2-carboxamido)azepane-1-carboxylate

A target compound was obtained by repeating the same procedure as in Preparation Example 1, except that in Step 4 of Preparation Example 1, tert-butyl (S)-3-aminoazepane-1-carboxylate was used instead of (S)-1-Boc-3-aminopiperidine.

MS (m/z): 418[M+1].

Example 1. Preparation of ethyl (S)-4-((5-(piperidin-3-ylcarbamoyl)-4-ureidothiophen-2-yl)ethynyl)benzoate

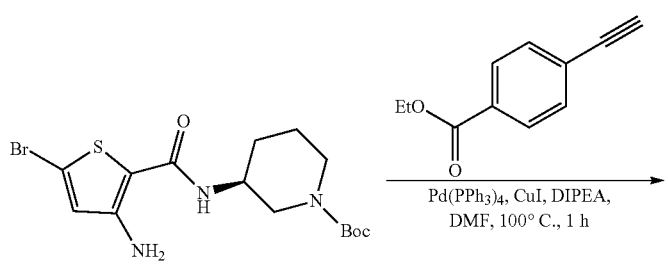

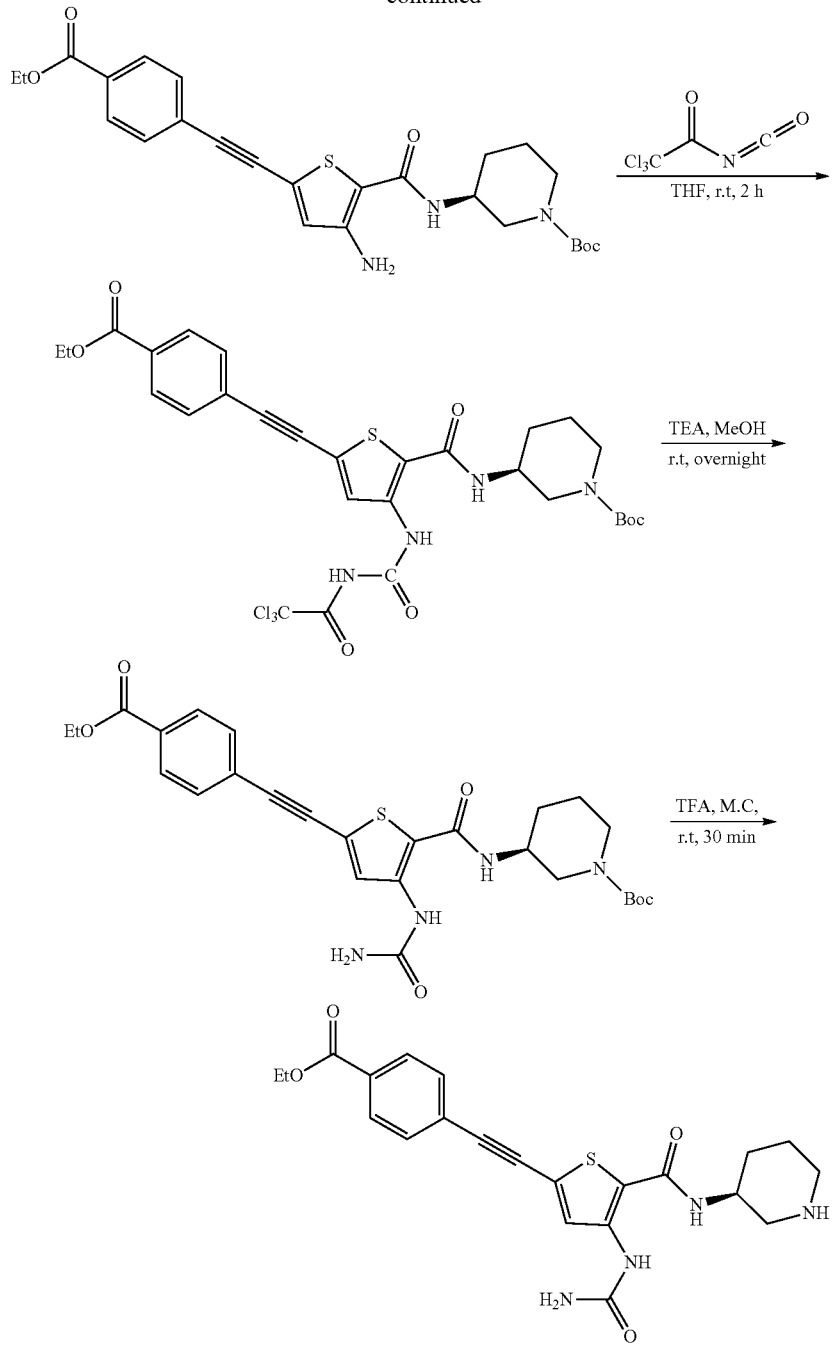

Step 1. Preparation of tert-butyl (S)-3-(3-amino-5-((4-(ethoxycarbonyl)phenyl)ethynyl)thiophene-2-carboxamido)piperidine-1-carboxylate Tert-butyl (S)-3-(3-amino-5-bromothiophene-2-carboxamido)piperidine-1-carboxylate (95.8 mg, 0.190 mmol), ethyl 4-ethynylbenzoate (30.0 mg, 0.172 mmol), and diisopropylethylamine (38 mg, 0.293 mmol) were dissolved in dimethylformamide (2 mL). Pd(PPh$_3$)$_4$ (9.96 mg, 8.62 umol) and CuI (3.28 mg, 0.017 mmol) were put into the reaction solution, and the resulting mixture was stirred at 100° C. for 12 hours. The reactant was cooled to room temperature, and then extracted with ethyl acetate and water to collect an organic layer. The collected organic layer was washed with brine solution, dried over sodium sulfate, concentrated under reduced pressure, and purified with MPLC to obtain a target compound (61.3 mg, 71.5%).

MS (m/z): 498[M+1].

Step 2. Preparation of tert-butyl (S)-3-(5-((4-(ethoxycarbonyl)phenyl)ethynyl)-3-(3-(2,2,2-trichloroacetyl)ureido)thiophene-2-carboxamido)piperidine-1-carboxylate Trichloroacetyl isocyanate (26.0 mg, 0.138 mmol) was slowly added dropwise to a solution of tert-butyl (S)-3-(3- amino-5-((4-(ethoxycarbonyl)phenyl)ethynyl)thiophene-2-carboxamido)piperidine-1-carboxylate (61.3 mg, 0.123 mmol) dissolved in tetrahydrofuran (1.15 mL), and the resulting mixture was stirred at room temperature for 2.5 hours. After the reaction was completed, an excessive amount of hexane was added thereto, and the resulting mixture was stirred for 1 hour. The produced solid was filtered and washed with hexane to obtain a solid target compound (85 mg, 100%)

MS (m/z): 687[M+1].

Step 3. Preparation of tert-butyl (S)-3-(5-((4-(ethoxycarbonyl)phenyl)ethynyl)-3-ureidothiophene-2-carboxamido)piperidine-1-carboxylate Triethyl amine (31.0 mg, 0.310 mmol) was added to a solution of tert-butyl (S)-3-(5-((4-(ethoxycarbonyl)phenyl)ethynyl)-3-(3-(2,2,2-trichloroacetyl)ureido)thiophene-2-carboxamido)piperidine-1-carboxylate (85 mg, 0.124 mmol) dissolved in methanol (2.5 mL), and the resulting mixture was stirred at room temperature for 12 hours. When the reaction was completed, the reaction solvent was removed under reduced pressure, and the residue was extracted by using ethyl acetate and a saturated $NaHCO_3$ solution. The collected organic layer was washed with brine solution, dried over sodium sulfate, concentrated under reduced pressure, and purified with MPLC to obtain a target compound (36.9 mg, 55%). MS (m/z): 541 [M+1].

Step 4. Preparation of ethyl (S)-4-((5-(piperidin-3-ylcarbamoyl)-4-ureidothiophen-2-yl)ethynyl)benzoate After tert-butyl (S)-3-(5-((4-(ethoxycarbonyl)phenyl)ethynyl)-3-ureidothiophene-2-carboxamido)piperidine-1-carboxylate (36.9 mg, 0.068 mmol) was dissolved in dichloromethane (8 mL), trifluoroacetic acid (5.96 g, 52.2 mmol) was added dropwise thereto, and the resulting mixture was stirred at room temperature for 30 minutes. When the reaction was completed, the reaction solvent was removed under reduced pressure, and the residue was extracted by using ethyl acetate and a saturated $NaHCO_3$ solution. The collected organic layer was washed with brine solution, dried over sodium sulfate, and then concentrated under reduced pressure. The residue was recrystallized by using dichloromethane and hexane to obtain a solid target compound (9.1 mg, 30.3%).

$^1$H NMR (400 MHz, DMSO-$d_6$) δ 9.99 (br s, 1H), 8.16 (s, 1H), 8.09 (s, 1H), 8.01 (d, 1H), 7.87-7.84 (m, 2H), 7.61 (t, 1H), 6.67 (br s, 1H), 4.34 (q, 2H), 3.77-3.75 (m, 1H), 2.94-2.91 (m, 1H), 2.79-2.67 (m, 1H), 2.45-2.32 (m, 2H), 1.83-1.80 (m, 1H), 1.63-1.41 (m, 3H), 1.34 (t, 3H), 1.17 (br s, 1H). MS (m/z): 440[M+1]. $t_R$=2.439 min (HPLC Condition 2).

Example 2. Preparation of (S)-5-(phenylethynyl)-N-(piperidin-3-yl)-3-ureidothiophene-2-carboxamide

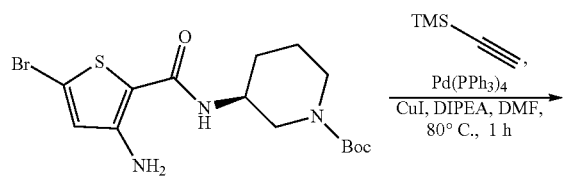

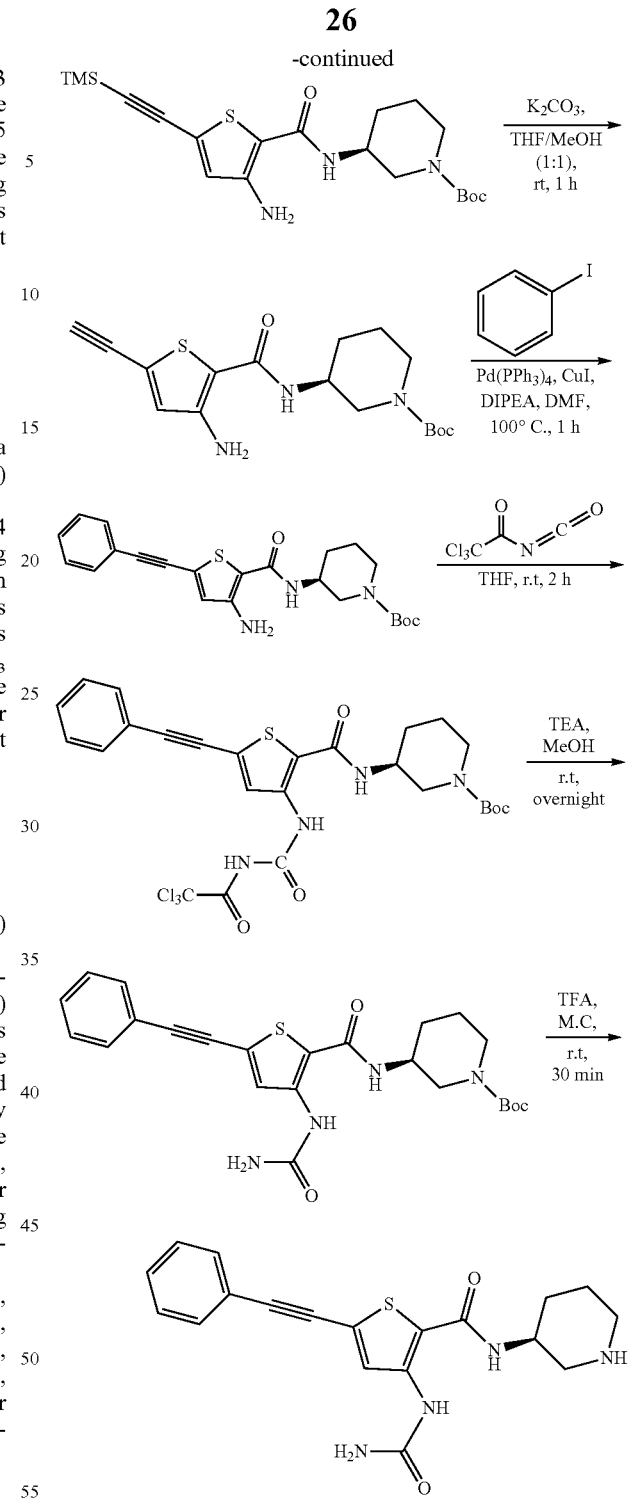

Step 1. Preparation of tert-butyl (S)-3-(3-amino-5-((trimethylsilyl)ethynyl)thiophene-2-carboxamido)piperidine-1-carboxylate After tert-butyl (S)-3-(3-amino-5-bromothiophene-2-carboxamido)piperidine-1-carboxylate (4.0 g, 9.89 mmol), trimethylsilylacetylene (1.07 g, 10.9 mmol), and diisopropylethylamine (1.70 g, 16.82 mmol) were dissolved in acetonitrile (76 mL), nitrogen was flowed thereto for 10 minutes. After Pd(PPh₃)₄ (21.4 mg, 0.019 mmol) and CuI (7.1 mg, 0.037 mmol) were added thereto, the resulting mixture was stirred at 80° C. for 1 hour. The reactant was cooled to room temperature, and then extracted with ethyl acetate and water. The collected organic layer was washed with brine solution, dried over sodium sulfate, concentrated under reduced pressure, and purified with MPLC to obtain a target compound (3.0 g, 72%).

MS (m/z): 422[M+1].

Step 2. Preparation of tert-butyl (S)-3-(3-amino-5-ethynylthiophene-2-carboxamido)piperidine-1-carboxylate After tert-butyl (S)-3-(3-amino-5-((trimethylsilyl)ethynyl)thiophene-2-carboxamido)piperidine-1-carboxylate (3.0 g, 7.12 mmol) was dissolved in tetrahydrofuran (25.4 mL), potassium carbonate (4.92 g) and methanol (25 mL) were sequentially added thereto, and then the suspension was stirred at room temperature for 1 hour. After the reaction was completed, the product was filtered with Celite, the reaction solvent was removed under reduced pressure, and then the residue was extracted by using ethyl acetate and water. The collected organic layer was washed with brine solution, dried over sodium sulfate, concentrated under reduced pressure, and purified with MPLC to obtain a target compound (2.3 g, 93%).

MS (m/z): 350[M+1].

Step 3. Preparation of tert-butyl (S)-3-(3-amino-5-(phenylethynyl)thiophene-2-carboxamido)piperidine-1-carboxylate After tert-butyl (S)-3-(3-amino-5-ethynylthiophene-2-carboxamido)piperidine-1-carboxylate (150 mg, 0.429 mmol), iodobenzene (88 mg, 0.429 mmol), and diisopropylethylamine (94 mg, 0.730 mmol) were dissolved in dimethylformamide (5 mL), nitrogen was flowed thereto for 10 minutes. After Pd(PPh₃)₄ (21.4 mg, 0.019 mmol) and CuI (7.1 mg, 0.037 mmol) were added thereto, the resulting mixture was stirred at 100° C. for 1 hour. The reactant was cooled to room temperature, and then extracted with ethyl acetate and water. The collected organic layer was washed with brine solution, dried over sodium sulfate, concentrated under reduced pressure, and purified with MPLC to obtain a target compound (173 mg, 95%).

MS (m/z): 426[M+1].

Step 4. Preparation of (S)-5-(phenylethynyl)-N-(piperidin-3-yl)-3-ureidothiophene-2-carboxamide A target compound was obtained by performing the processes of Step 2, Step 3, and Step 4 of Example 1 using tert-butyl (S)-3-(3-amino-5-(phenylethynyl)thiophene-2-carboxamido)piperidine-1-carboxylate.

¹H NMR (400 MHz, DMSO-d₆) δ 10.01 (br s, 1H), 8.12 (s, 1H), 7.88 (d, 1H), 7.59 (m, 2H), 7.45 (m, 2H), 6.69 (br s, 2H), 3.79 (m, 1H), 2.96 (m, 1H), 2.81 (m, 1H), 2.42 (m, 2H), 1.81 (m, 1H), 1.63 (m, 1H), 1.47 (m, 2H). MS (m/z): 369 [M+1]. $t_R$=3.722 min (HPLC Condition 1).

Example 3. Preparation of (S)—N-(piperidin-3-yl)-5-(pyridin-3-ylethynyl)-3-ureidothiophene-2-carboxamide

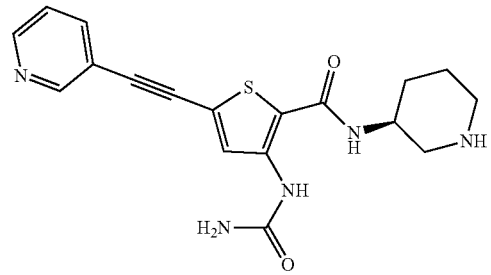 [SMILES: NC(=O)Nc1cc(C#Cc2cccnc2)sc1C(=O)N[C@H]1CCCNC1]

A target compound was obtained by applying the method in Example 2.

¹H NMR (400 MHz, DMSO-d₆) δ 10.00 (br s, 1H), 8.79 (s, 1H), 8.62 (d, 1H), 8.17 (s, 1H), 8.03 (d, 1H), 7.91 (d, 1H), 7.49 (m, 1H), 6.70 (br s, 2H), 3.79 (m, 1H), 2.95 (m, 1H), 2.80 (m, 1H), 2.41 (m, 2H), 1.82 (m, 1H), 1.63 (m, 1H), 1.47 (m, 2H). MS (m/z): 370 [M+1]. $t_R$=3.237 min (HPLC Condition 1)

Example 4. Preparation of (S)—N-(piperidin-3-yl)-5-(pyridin-4-ylethynyl)-3-ureidothiophene-2-carboxamide

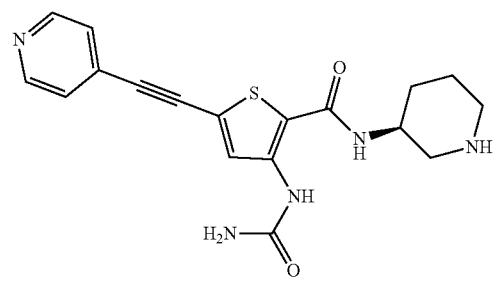 [SMILES: NC(=O)Nc1cc(C#Cc2ccncc2)sc1C(=O)N[C@H]1CCCNC1]

A target compound was obtained by applying the method in Example 2.

¹H NMR (400 MHz, DMSO-d₆) δ 9.99 (br s, 1H), 8.65 (d, 1H), 8.21 (s, 1H), 7.96 (d, 1H), 7.57 (d, 1H), 6.72 (br s, 2H), 3.78 (m, 1H), 2.94 (m, 1H), 2.82 (m, 1H), 2.42 (m, 2H), 1.83 (m, 1H), 1.64 (m, 1H), 1.41 (m, 2H). MS (m/z): 370 [M+1]. $t_R$=3.183 min (HPLC Condition 1)

Example 5. Preparation of (S)-5-((3-nitrophenyl)ethynyl)-N-(piperidin-3-yl)-3-ureidothiophene-2-carboxamide

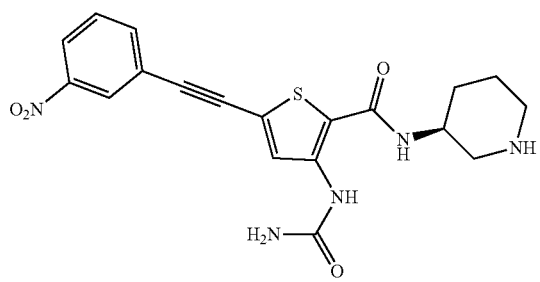 [SMILES: NC(=O)Nc1cc(C#Cc2cccc([N+](=O)[O-])c2)sc1C(=O)N[C@H]1CCCNC1]

A target compound was obtained by applying the method in Example 2.

¹H NMR (400 MHz, DMSO-d₆) δ 10.00 (br s, 1H), 8.40 (s, 1H), 8.29 (d, 1H), 8.21 (s, 1H), 8.05 (d, 1H), 7.92 (d, 1H), 7.74 (t, 1H), 6.71 (br s, 2H), 3.77 (m, 1H), 2.95 (m, 1H), 2.80 (m, 1H), 2.41 (m, 1H), 1.83 (m, 1H), 1.63 (m, 1H), 1.50 (m, 2H). MS (m/z): 414 [M+1]. $t_R$=3.753 min (HPLC Condition 1)

Example 6. Preparation of (S)-5-((3-cyanophenyl)ethynyl)-N-(piperidin-3-yl)-3-ureidothiophene-2-carboxamide

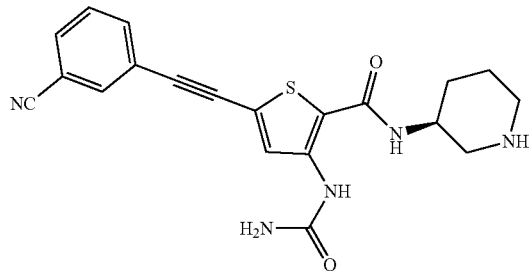 [SMILES: N#Cc1cccc(C#Cc2cc(NC(N)=O)c(C(=O)N[C@H]3CCCNC3)s2)c1]

A target compound was obtained by applying the method in Example 2.

¹H NMR (400 MHz, DMSO-d₆) δ 10.00 (br s, 1H), 8.18 (s, 1H), 8.13 (s, 1H), 7.92 (m, 3H), 7.65 (t, 1H), 6.70 (br s, 2H), 3.75 (m, 1H), 2.92 (m, 1H), 2.79 (m, 1H), 2.38 (m, 2H), 1.83 (m, 1H), 1.62 (m, 1H), 1.46 (m, 2H). MS (m/z): 394 [M+1]. $t_R$=3.618 min (HPLC Condition 1)

Example 7. Preparation of (S)-5-((4-nitrophenyl)ethynyl)-N-(piperidin-3-yl)-3-ureidothiophene-2-carboxamide

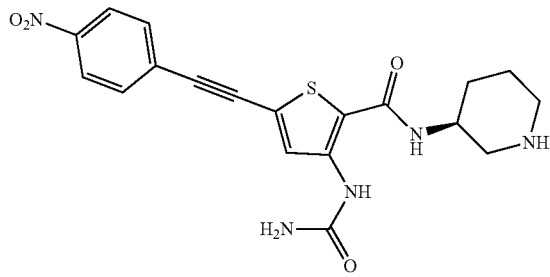 [SMILES: NC(=O)Nc1cc(C#Cc2ccc([N+](=O)[O-])cc2)sc1C(=O)N[C@H]1CCCNC1]

A target compound was obtained by applying the method in Example 2.

¹H NMR (400 MHz, DMSO-d₆) δ 10.00 (br s, 1H), 8.27 (d, 2H), 8.23 (s, 1H), 7.94 (d, 1H), 7.88 (d, 1H), 6.71 (br s, 2H), 3.77 (m, 1H), 2.93 (m, 1H), 2.80 (m, 1H), 2.38 (m, 2H), 1.83 (m, 1H), 1.63 (m, 1H), 1.47 (m, 2H). MS (m/z): 414 [M+1]. $t_R$=3.743 min (HPLC Condition 1)

Example 8. Preparation of (S)-5-((4-chlorophenyl)ethynyl)-N-(piperidin-3-yl)-3-ureidothiophene-2-carboxamide

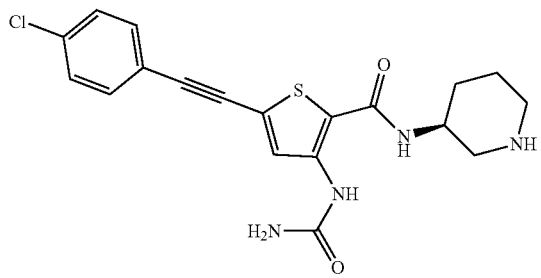 [SMILES: NC(=O)Nc1cc(C#Cc2ccc(Cl)cc2)sc1C(=O)N[C@H]1CCCNC1]

A target compound was obtained by applying the method in Example 2.

¹H NMR (400 MHz, DMSO-d₆) δ 10.00 (br s, 1H), 8.13 (s, 1H), 7.88 (d, 1H), 7.63 (d, 1H), 7.53 (d, 1H), 6.69 (br s, 2H), 3.77 (m, 1H), 2.95 (m, 1H), 2.92 (m, 1H), 2.40 (m, 2H), 1.82 (m, 1H), 1.63 (m, 1H), 1.47 (m, 2H). MS (m/z): 403 [M+1]. $t_R$=3.988 min (HPLC Condition 1)

Example 9. Preparation of (S)-5-((4-fluorophenyl)ethynyl)-N-(piperidin-3-yl)-3-ureidothiophene-2-carboxamide

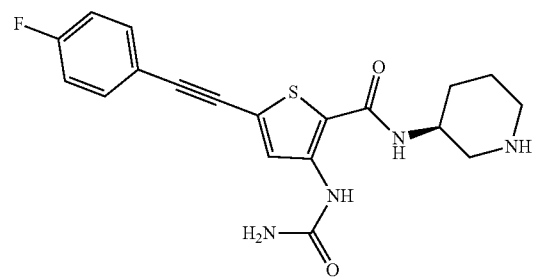 [SMILES: NC(=O)Nc1cc(C#Cc2ccc(F)cc2)sc1C(=O)N[C@H]1CCCNC1]

A target compound was obtained by applying the method in Example 2.

¹H NMR (400 MHz, DMSO-d₆) δ 10.00 (br s, 1H), 8.12 (s, 1H), 7.86 (d, 1H), 7.67 (m, 2H), 7.30 (t, 2H), 6.68 (br s, 2H), 3.77 (m, 1H), 2.94 (m, 1H), 2.80 (m, 1H), 2.40 (m, 2H), 1.81 (m, 1H), 1.63 (m, 1H), 1.47 (m, 2H). MS (m/z): 387 [M+1]. $t_R$=3.803 min (HPLC Condition 1)

Example 10. Preparation of (S)—N-(piperidin-3-yl)-5-(pyridin-2-ylethynyl)-3-ureidothiophene-2-carboxamide

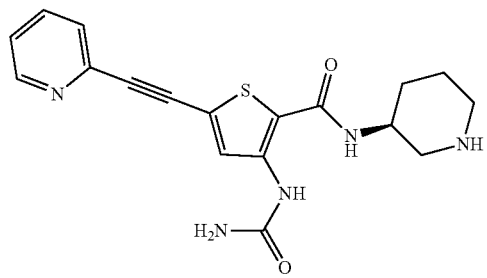 [SMILES: NC(=O)Nc1cc(C#Cc2ccccn2)sc1C(=O)N[C@H]1CCCNC1]

A target compound was obtained by applying the method in Example 2.

$^1$H NMR (400 MHz, DMSO-$d_6$) δ 10.01 (br s, 1H), 8.63 (d, 1H), 8.19 (s, 1H), 8.00 (d, 1H), 7.87 (m, 1H), 7.70 (d, 1H), 7.45 (m, 1H) 6.70 (br s, 2H), 3.81 (m, 1H), 2.97 (m, 1H), 2.84 (m, 1H), 2.44 (m, 2H), 1.84 (m, 1H), 1.64 (m, 1H), 1.48 (m, 2H). MS (m/z): 370 [M+1]. $t_R$=3.247 min (HPLC Condition 1)

Example 11. Preparation of (S)-5-((4-cyanophenyl)ethynyl)-N-(piperidin-3-yl)-3-ureidothiophene-2-carboxamide

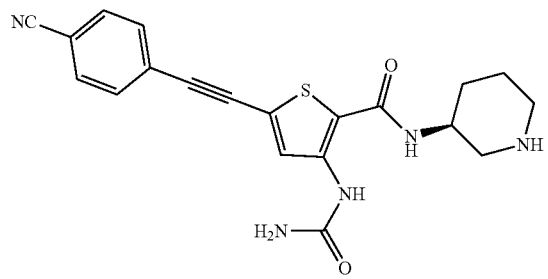 [SMILES: N#Cc1ccc(C#Cc2cc(NC(N)=O)c(C(=O)N[C@H]3CCCNC3)s2)cc1]

A target compound was obtained by applying the method in Example 2.

$^1$H NMR (400 MHz, DMSO-$d_6$) δ 10.00 (br s, 1H), 8.20 (s, 1H), 7.91 (m, 3H), 7.78 (d, 1H), 6.71 (br s, 2H), 3.77 (m, 1H), 2.92 (m, 1H), 2.77 (m, 1H), 2.38 (m, 2H), 1.81 (m, 1H), 1.63 (m, 1H), 1.47 (m, 2H). MS (m/z): 394 [M+1]. $t_R$=3.604 min (HPLC Condition 1)

Example 12. Preparation of (S)-5-((1H-indazol-3-yl)ethynyl)-N-(piperidin-3-yl)-3-ureidothiophene-2-carboxamide

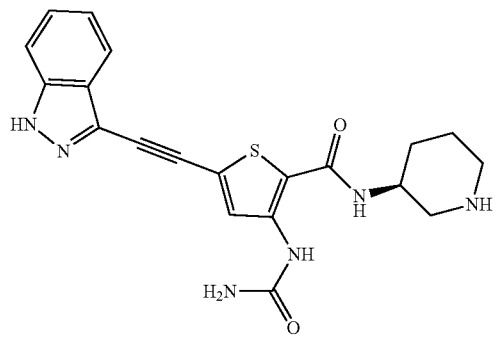 [SMILES: NC(=O)Nc1cc(C#Cc2n[nH]c3ccccc23)sc1C(=O)N[C@H]1CCCNC1]

A target compound was obtained by applying the method in Example 2.

$^1$H NMR (400 MHz, DMSO-$d_6$) δ 10.04 (br s, 1H), 8.21 (s, 1H), 7.92 (d, 1H), 7.64 (d, 1H), 7.46 (t, 1H), 7.27 (t, 1H) 6.71 (br s, 2H), 3.78 (m, 1H), 2.96 (m, 1H), 2.81 (m, 1H), 2.40 (m, 2H), 1.82 (m, 1H), 1.63 (m, 1H), 1.47 (m, 2H). MS (m/z): 409 [M+1]. $t_R$=3.388 min (HPLC Condition 1)

Example 13. Preparation of (S)-5-((6-fluoropyridin-3-yl)ethynyl)-N-(piperidin-3-yl)-3-ureidothiophene-2-carboxamide

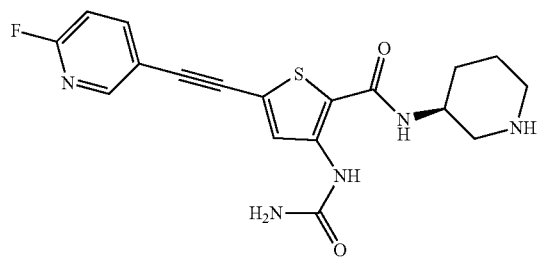 [SMILES: NC(=O)Nc1cc(C#Cc2ccc(F)nc2)sc1C(=O)N[C@H]1CCCNC1]

A target compound was obtained by applying the method in Example 2.

$^1$H NMR (400 MHz, DMSO-$d_6$) δ 10.01 (br s, 1H), 8.53 (s, 1H), 8.25 (m, 1H), 8.18 (s, 1H), 7.92 (d, 1H), 7.33 (m, 1H), 6.70 (br s, 2H), 3.78 (m, 1H), 2.94 (m, 1H), 2.80 (m, 1H), 2.39 (m, 2H), 1.81 (m, 1H), 1.63 (m, 1H), 1.47 (m, 2H). MS (m/z): 388 [M+1]. $t_R$=3.254 min (HPLC Condition 1)

Example 14. Preparation of (S)-5-((3,4-difluorophenyl)ethynyl)-N-(piperidin-3-yl)-3-ureidothiophene-2-carboxamide

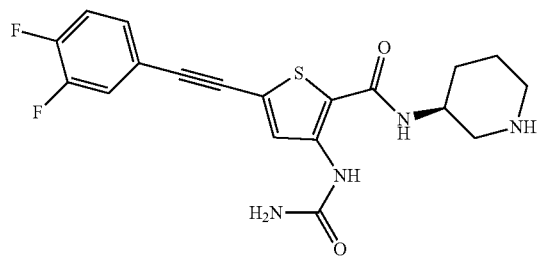 [SMILES: NC(=O)Nc1cc(C#Cc2ccc(F)c(F)c2)sc1C(=O)N[C@H]1CCCNC1]

A target compound was obtained by applying the method in Example 2.

$^1$H NMR (400 MHz, DMSO-$d_6$) δ 10.00 (br s, 1H), 8.15 (s, 1H), 7.82 (d, 1H), 7.78 (m, 1H), 7.51 (m, 2H), 6.69 (br s, 2H), 3.76 (m, 1H), 2.92 (m, 1H), 2.79 (m, 1H), 2.38 (m, 2H), 1.83 (m, 1H), 1.62 (m, 1H), 1.47 (m, 2H). MS (m/z): 405 [M+1]. $t_R$=3.896 min (HPLC Condition 1)

Example 15. Preparation of (S)-5-((1-methyl-1H-pyrazol-4-yl)ethynyl)-N-(piperidin-3-yl)-3-ureidothiophene-2-carboxamide trifluoroacetate

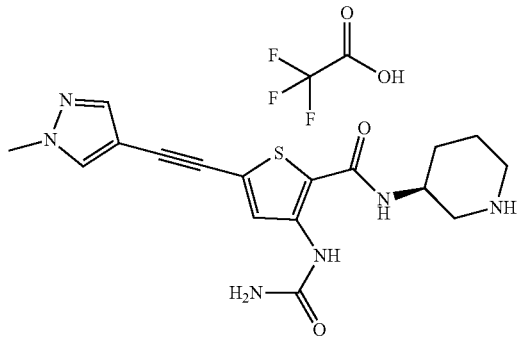

A target compound was obtained by applying the method in Example 2.

$^1$H NMR (400 MHz, DMSO-d$_6$) δ 9.89 (s, 1H), 8.68 (br s, 2H), 8.15 (s, 1H), 8.09 (d, 1H), 8.03 (s, 1H), 7.75 (s, 1H), 6.70 (br s, 2H), 4.10 (m, 1H), 3.85 (s, 3H), 3.21 (m, 2H), 2.82 (m, 2H), 1.87 (m, 2H), 1.56 (m, 2H). MS (m/z): 373 [M+1]. $t_R$=4.309 min (HPLC Condition 1)

Example 16. Preparation of ((S)—N-(piperidin-3-yl)-5-((4-(trifluoromethyl)phenyl)ethynyl)-3-ureido-thiophene-2-carboxamide trifluoroacetate

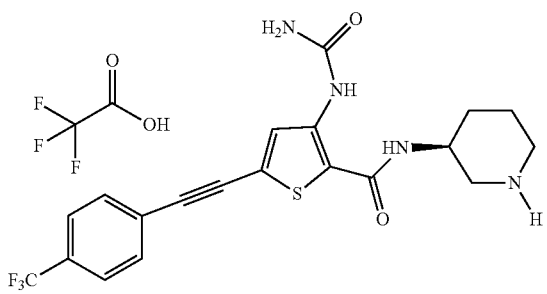

A target compound was obtained by applying the method in Example 2.

MS (m/z): 436 [M+1]. $t_R$=2.142 min (HPLC Condition 2)

Example 17. Preparation of (S)—N-(piperidin-3-yl)-5-((6-(trifluoromethyl)pyridin-3-yl)ethynyl)-3-ureidothiophene-2-carboxamide

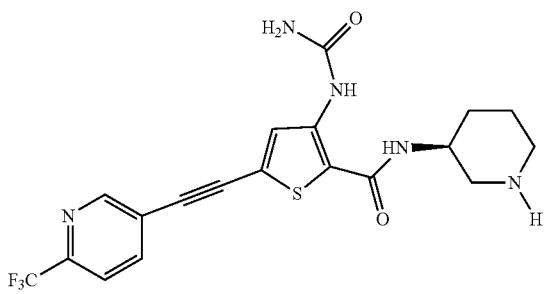 [SMILES: NC(=O)Nc1cc(C#Cc2ccc(C(F)(F)F)nc2)sc1C(=O)N[C@H]1CCCNC1]

A target compound was obtained by applying the method in Example 2.

$^1$H NMR (400 MHz, DMSO-d$_6$) δ 9.97 (br s, 1H), 8.97 (s, 1H), 8.32-8.29 (m, 1H), 8.22 (s, 1H), 8.01-7.97 (m, 2H), 6.70 (br s, 2H), 3.83-3.82 (m, 1H), 3.00-2.96 (m, 1H), 2.85-2.82 (m, 1H), 1.86-1.80 (m, 1H), 1.66-1.63 (m, 1H), 1.51-1.40 (m, 3H), 1.20 (br s, 1H), 0.85-0.79 (m, 1H). MS (m/z): 437 [M+1]. $t_R$=1.925 min (HPLC Condition 2)

Example 18. Preparation of methyl (S)-4-((5-(piperidin-3-ylcarbamoyl)-4-ureidothiophen-2-yl)ethynyl)benzoate trifluoroacetate

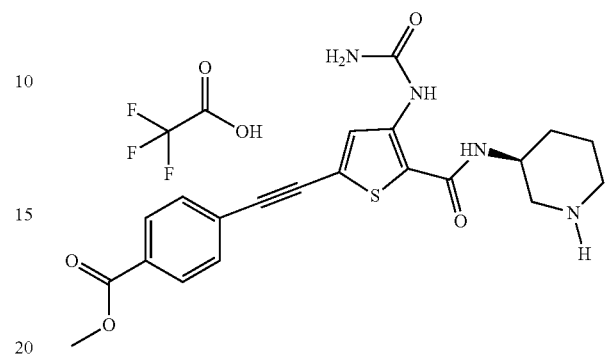

A target compound was obtained by applying the method in Example 2.

$^1$H NMR (400 MHz, DMSO-d$_6$) δ 9.89 (s, 1H), 8.70 (br s, 2H), 8.21-8.18 (m, 2H), 8.00 (d, 2H), 7.73 (d, 2H), 6.73 (br s, 1H), 4.15-4.08 (m, 1H), 3.87 (s, 3H), 3.33-3.20 (m, 4H), 3.16 (s, 2H), 2.87-2.82 (m, 2H), 1.90-1.86 (m, 2H), 1.71-1.54 (m, 2H). MS (m/z): 426 [M+1]. $t_R$=1.969 min (HPLC Condition 2)

Example 19. Preparation of (S)-5-((6-chloropyridin-3-yl)ethynyl)-N-(piperidin-3-yl)-3-ureidothiophene-2-carboxamide hydrochloride

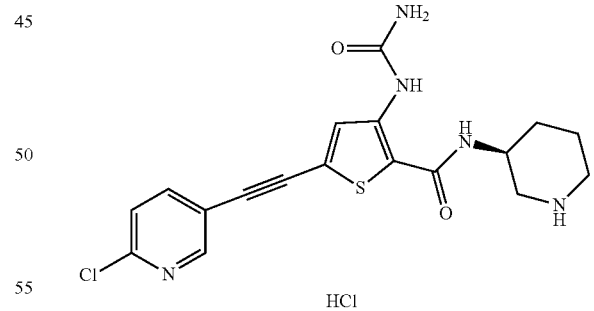

A target compound was obtained by applying the method in Example 2.

$^1$H NMR (400 MHz, DMSO-d$_6$) δ 9.94 (s, 1H), 9.35 (br s, 1H), 9.27 (br s, 1H), 8.67-8.66 (m, 1H), 8.42 (d, 1H), 8.20 (s, 1H), 8.11 (dd, 1H), 7.63 (d, 1H), 6.73 (br s, 1H), 4.21-4.20 (m, 1H), 3.27-3.13 (m, 2H), 2.95-2.81 (m, 2H), 1.91-1.86 (m, 2H), 1.74-1.50 (m, 2H). MS (m/z): 403 [M+1]. $t_R$=2.305 min (HPLC Condition 2)

Example 20. Preparation of (S)-5-((5-fluoropyridin-3-yl)ethynyl)-N-(piperidin-3-yl)-3-ureidothiophene-2-carboxamide

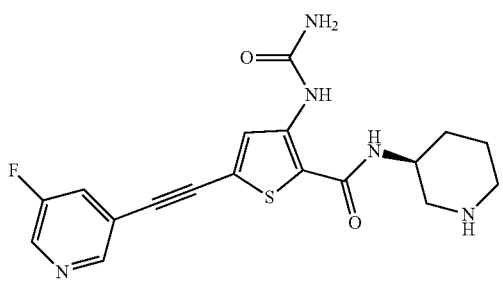 [SMILES: NC(=O)Nc1cc(C#Cc2cncc(F)c2)sc1C(=O)N[C@H]1CCCNC1]

A target compound was obtained by applying the method in Example 2.

¹H NMR (400 MHz, DMSO-d₆) δ 9.98 (br s, 1H), 8.67-8.64 (m, 2H), 8.20 (s, 1H), 8.09-8.05 (m, 1H), 7.90 (d, 1H), 6.68 (br s, 1H), 3.79-3.72 (m, 1H), 3.10-2.91 (m, 1H), 2.91-2.49 (m, 1H), 2.44-2.30 (m, 2H), 1.83-1.79 (m, 1H), 1.62-1.59 (m, 1H), 1.52-1.22 (m, 2H). MS (m/z): 387 [M+1]. $t_R$=2.169 min (HPLC Condition 2)

Example 21. Preparation of (S)-5-((2-fluoropyridin-4-yl)ethynyl)-N-(piperidin-3-yl)-3-ureidothiophene-2-carboxamide

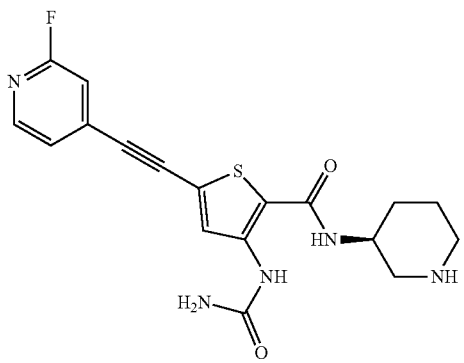 [SMILES: NC(=O)Nc1cc(C#Cc2ccnc(F)c2)sc1C(=O)N[C@H]1CCCNC1]

A target compound was obtained by applying the method in Example 2.

¹H NMR (400 MHz, DMSO-d₆) δ 9.87 (s, 1H), 8.63 (br, 2H), 8.31 (d, 1H), 8.25 (s, 1H), 8.24 (d, 1H), 8.53 (d, 1H), 7.47 (s, 1H), 6.76 (br, 1H), 4.11-4.09 (m, 1H), 3.23-3.18 (m, 2H), 2.91-2.82 (m, 2H), 1.89-1.81 (m 2H), 1.66-1.54 (m, 2H). MS (m/z): 388. $t_R$=4.710 min (HPLC Condition 1)

Example 22. Preparation of (S)-5-((3-fluorophenyl)ethynyl)-N-(piperidin-3-yl)-3-ureidothiophene-2-carboxamide

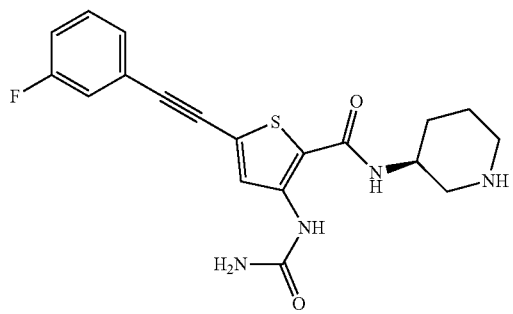 [SMILES: NC(=O)Nc1cc(C#Cc2cccc(F)c2)sc1C(=O)N[C@H]1CCCNC1]

A target compound was obtained by applying the method in Example 2.

¹H NMR (400 MHz, DMSO-d₆) δ 9.89 (s, 1H), 8.67 (brs, 2H), 8.19 (s, 1H), 8.17 (s, 1H), 7.51 (m, 3H), 7.36 (t, 1H), 6.74 (brs, 2H), 4.12 (m, 1H), 3.32 (m, 1H), 3.24 (m, 1H), 2.86 (m, 2H), 1.89 (m, 2H), 1.64 (m, 2H). MS (m/z): 387[M+1]. $t_R$=5.13 min (HPLC Condition 1)

Example 23. Preparation of (S)-5-((1-(1-(methylsulfonyl)piperidin-4-yl)-1H-pyrazol-4-yl)ethynyl)-N-(piperidin-3-yl)-3-ureidothiophene-2-carboxamide

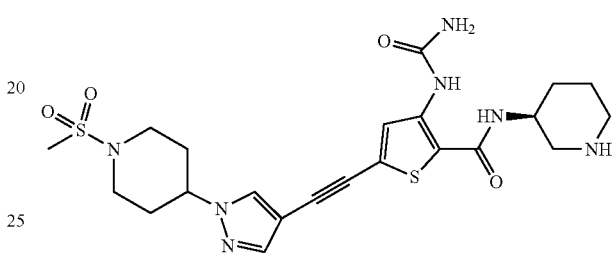

A target compound was obtained by applying the method in Example 2.

¹H NMR (400 MHz, DMSO-d₆) δ 9.90 (s, 1H), 8.62 (br s, 2H), 8.32 (s, 1H), 8.09 (d, 1H), 8.04 (s, 1H), 7.81 (s, 1H), 6.71 (br s, 1H), 4.39-4.33 (m, 1H), 4.13-4.09 (m, 1H), 3.65 (d, 2H), 3.22 (d, 2H), 2.92 (s, 3H), 2.89-2.76 (m, 4H), 2.15-2.09 (m, 2H), 1.98 (ddd, 2H), 1.92-1.85 (m, 2H), 1.67-1.55 (m, 2H). MS (m/z): 153 [M+H]⁺. $t_R$=4.583 min (HPLC Condition 1)

Example 24. Preparation of (S)—N-(piperidin-3-yl)-5-(p-tolylethynyl)-3-ureidothiophene-2-carboxamide

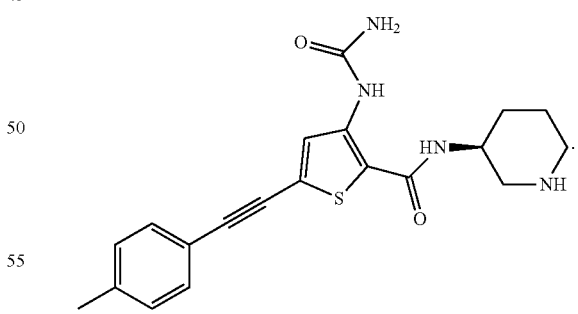

A target compound was obtained by applying the method in Example 2.

¹H NMR (400 MHz, DMSO-d₆) δ 9.90 (s, 1H), 8.66 (br s, 2H), 8.12 (d, 1H), 8.10 (s, 1H), 7.48 (d, 2H), 7.27 (d, 2H), 6.72 (br s, 1H), 4.15-4.07 (m, 1H), 3.30 (d, 1H), 3.22 (d, 1H), 2.89-2.73 (m, 2H), 2.35 (s, 3H), 1.91-1.85 (m, 2H), 1.72-1.53 (m, 2H). MS (m/z): 153 [M+H]⁺. $t_R$=4.583 min (HPLC Condition 1)

Example 25. Preparation of (S)-5-((3-bromo-4-cyanophenyl)ethynyl)-N-(piperidin-3-yl)-3-ureidothiophene-2-carboxamide

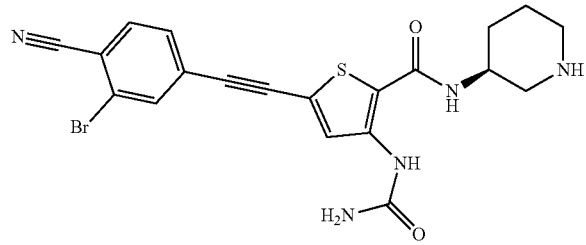 [SMILES: N#Cc1ccc(C#Cc2cc(NC(N)=O)c(C(=O)N[C@H]3CCCNC3)s2)cc1Br]

A target compound was obtained by applying the method in Example 2.
$^1$H NMR (400 MHz, CH$_3$OH-d$_4$) δ 7.99 (s, 1H), 7.82 (s, 1H), 7.68 (d, J=8.1 Hz, 1H), 7.53 (d, J=8.0 Hz, 1H), 3.91-3.86 (m, 1H), 3.04-3.00 (m, 1H), 2.84-2.80 (m, 1H), 2.48-2.41 (m, 2H), 1.88-1.80 (m, 2H), 1.51-1.40 (m, 2H). MS (m/z): 474[M+H]. t$_R$=5.251 min (HPLC Condition 1)

Example 26. Preparation of (S)-5-((4-cyano-3-fluorophenyl)ethynyl)-N-(piperidin-3-yl)-3-ureidothiophene-2-carboxamide

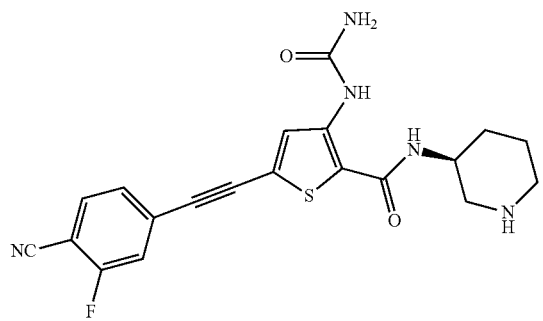 [SMILES: N#Cc1ccc(C#Cc2cc(NC(N)=O)c(C(=O)N[C@H]3CCCNC3)s2)cc1F]

A target compound was obtained by applying the method in Example 2.
$^1$H NMR (400 MHz, DMSO-d$_6$) δ 9.99 (br s, 1H), 8.21 (s, 1H), 7.99 (t, 1H), 7.93 (d, 1H), 7.84 (dd, 1H), 7.62 (dd, 1H), 6.72 (br s, 2H), 3.75-3.71 (m, 1H), 3.15 (d, 1H), 2.91 (dd, 1H), 2.76 (d, 1H), 2.42-2.35 (m, 2H), 1.81-1.78 (m, 1H), 1.61-1.57 (m, 1H), 1.51-1.31 (m, 2H). MS (m/z): 412 [m+1]. t$_R$=5.075 min (HPLC Condition 1)

Example 27. Preparation of (S)-5-((3-fluoro-4-(trifluoromethyl)phenyl)ethynyl)-N-(piperidin-3-yl)-3-ureidothiophene-2-carboxamide trifluoroacetate

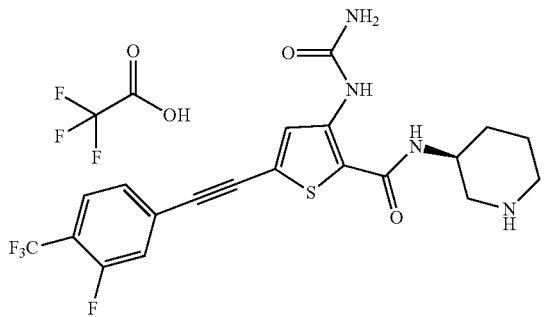

A target compound was obtained by applying the method in Example 2.

$^1$H NMR (400 MHz, DMSO-d$_6$) δ 9.87 (s, 1H), 8.66 (br s, 2H), 8.22-8.20 (m, 2H), 7.87-7.82 (m', 2H), 7.63 (d, 1H), 6.74 (br s, 1H), 4.14-4.0 (m, 1H), 3.29 (d, 2H), 3.21 (d, 1H), 2.84-2.80 (m, 2H), 1.89-1.84 (m, 2H), 1.66-1.53 (m, 2H). MS (m/z): 455 [m+1]. t$_R$=5.593 min (HPLC Condition 1)

Example 28. Preparation of (S)-5-((4-chloro-3-cyanophenyl)ethynyl)-N-(piperidin-3-yl)-3-ureidothiophene-2-carboxamide trifluoroacetate

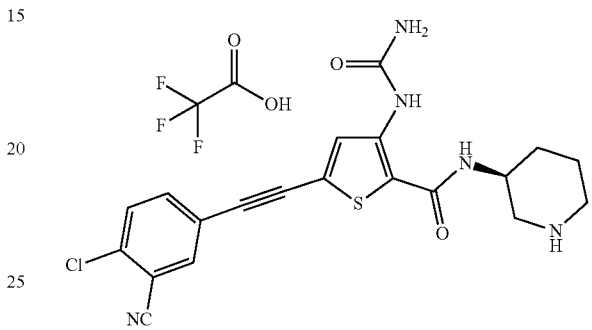

A target compound was obtained by applying the method in Example 2.

$^1$H NMR (400 MHz, DMSO-d$_6$) δ 9.89 (s, 1H), 8.68 (br s, 2H), 8.29 (d, 1H), 8.22-8.20 (m, 2H), 7.94 (dd, 1H), 7.83 (d, 1H), 6.74 (br s, 1H), 4.15-4.08 (m, 1H), 3.30 (d, 2H), 3.22 (d, 1H), 2.87-2.80 (m, 2H), 1.90-1.85 (m, 2H), 1.70-1.53 (m, 2H). MS (m/z): 428 [m+1]. t$_R$=5.452 min (HPLC Condition 1)

Example 29. Preparation of (S)-5-((2-chloropyrimidin-5-yl)ethynyl)-N-(piperidin-3-yl)-3-ureidothiophene-2-carboxamide trifluoroacetate

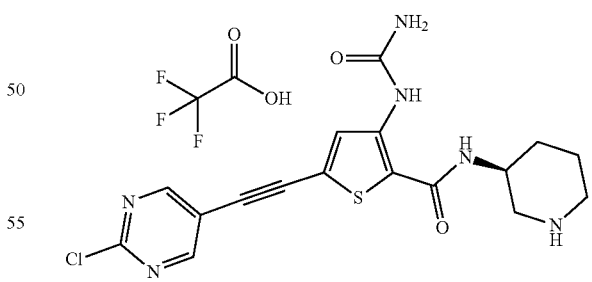

A target compound was obtained by applying the method in Example 2.

$^1$H NMR (400 MHz, DMSO-d$_6$) δ 9.89 (s, 1H), 9.04 (s, 1H), 8.67 (br s, 2H), 8.25-8.23 (m, 2H), 6.75 (br s, 1H), 4.12-4.08 (m, 1H), 3.31 (d, 2H), 3.22 (d, 1H), 2.88-2.83 (m, 2H), 1.91-1.85 (m, 2H), 1.70-1.54 (m, 2H). MS (m/z): 405 [m+1]. t$_R$=4.675 min (HPLC Condition 1)

Example 30. Preparation of (S)—N-(piperidin-3-yl)-5-(pyrazin-2-ylethynyl)-3-ureidothiophene-2-carboxamide

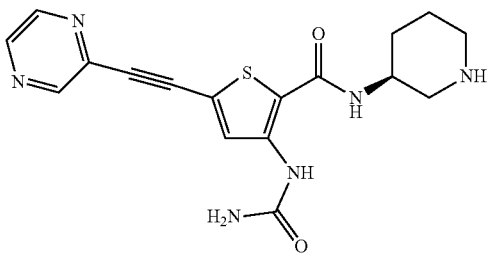 [SMILES: NC(=O)Nc1cc(C#Cc2cnccn2)sc1C(=O)N[C@H]1CCCNC1]

A target compound was obtained by applying the method in Example 2.

$^1$H NMR (400 MHz, DMSO-d$_6$) δ 9.89 (s, 1H), 8.95 (s, 1H), 8.73-8.64 (m, 4H), 8.28 (s, 1H), 8.26 (d, 1H), 6.75 (br, 1H), 4.13-4.11 (m, 1H), 3.32-3.20 (m, 2H), 2.86-2.83 (m, 2H), 1.90-1.87 (m, 2H), 1.67-1.58 (m, 2H). MS (m/z): 371[M+H]. t$_R$=4.267 min (HPLC Condition 1)

Example 31. Preparation of (S)-5-((4-chloro-3-fluorophenyl)ethynyl)-N-(piperidin-3-yl)-3-ureidothiophene-2-carboxamide

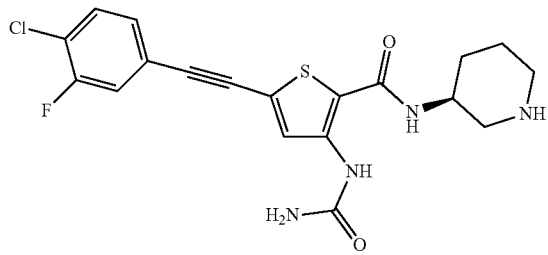 [SMILES: NC(=O)Nc1cc(C#Cc2ccc(Cl)c(F)c2)sc1C(=O)N[C@H]1CCCNC1]

A target compound was obtained by applying the method in Example 2.

$^1$H NMR (400 MHz, DMSO-d$_6$) δ 9.98 (s, 1H) 8.16 (s, 1H), 7.85 (d, 1H), 7.74 (d, 1H), 7.67 (t, 1H), 7.45 (d, 1H), 6.66 (br, 2H), 3.76 (m, 1H), 2.91 (m, 1H), 2.75 (m, 1H), 2.35 (m, 2H), 1.80 (m, 1H), 1.36 (m, 2H). MS (m/z): 421 [M+H]. t$_R$=5.205 min (HPLC Condition 1)

Example 32. Preparation of (S)-5-((3,5-difluorophenyl)ethynyl)-N-(piperidin-3-yl)-3-ureidothiophene-2-carboxamide

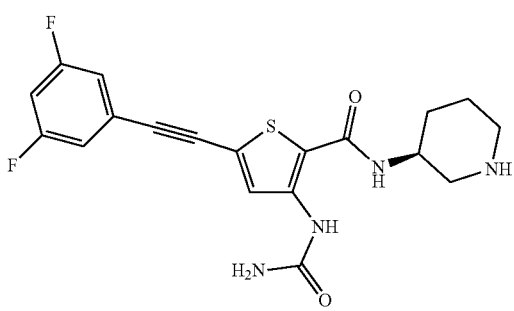 [SMILES: NC(=O)Nc1cc(C#Cc2cc(F)cc(F)c2)sc1C(=O)N[C@H]1CCCNC1]

A target compound was obtained by applying the method in Example 2.

$^1$H NMR (400 MHz, DMSO-d$_6$) δ 9.98 (s, 1H) 8.18 (s, 1H), 7.86 (d, 1H), 7.70 (m, 3H), 6.66 (br, 2H), 3.77 (m, 1H), 3.32 (m, 1H), 2.79 (m, 1H) 2.35 (m, 2H), 1.61 (m, 1H), 1.49 (m, 1H), 1.39 (m, 2H). MS (m/z): 405 [M+H]. t$_R$=5.411 min (HPLC Condition 1)

Example 33. Preparation of (S)-5-((2-fluorophenyl)ethynyl)-N-(piperidin-3-yl)-3-ureidothiophene-2-carboxamide

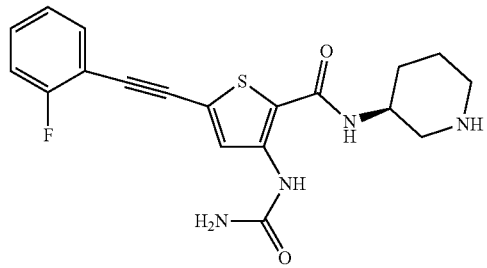 [SMILES: NC(=O)Nc1cc(C#Cc2ccccc2F)sc1C(=O)N[C@H]1CCCNC1]

A target compound was obtained by applying the method in Example 2.

$^1$H NMR (400 MHz, DMSO-d$_6$) δ 10.00 (s, 1H) 8.15 (s, 1H), 7.88 (d, 1H), 7.70 (t, 1H), 7.53 (Q, 1H) 7.37 (t, 1H), 7.29 (t, 1H), 6.69 (br, 2H), 3.77 (m, 1H), 2.93 (m, 1H), 2.62 (m, 1H) 2.39 (m, 2H), 1.86 (m, 1H), 1.62 (m, 1H), 1.46 (m, 2H). MS (m/z): 387 [M+H]. t$_R$=5.058 min (HPLC Condition 1)

Example 34. Preparation of (S)-5-((2,3-difluorophenyl)ethynyl)-N-(piperidin-3-yl)-3-ureidothiophene-2-carboxamide

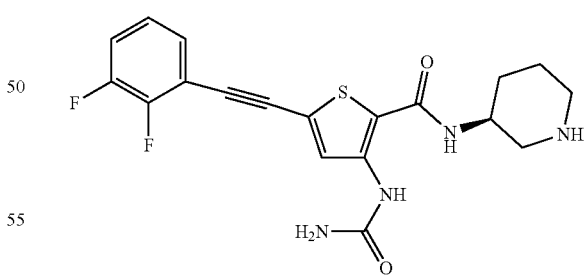

A target compound was obtained by applying the method in Example 2.

$^1$H NMR (400 MHz, DMSO-d$_6$) δ 10.00 (s, 1H), 8.18 (s, 1H), 7.90 (d, 1H), 7.53 (m, 1H), 7.52 (t, 1H), 7.50 (m, 1H), 6.70 (br, 2H), 3.76 (m, 1H), 2.92 (m, 1H), 2.77 (m, 1H), 2.33 (m, 2H), 1.81 (m, 1H), 1.61 (m, 1H), 1.48 (m, 2H). MS (m/z): 405 [M+H]. t$_R$=5.169 min (HPLC Condition 1)

Example 35. Preparation of (S)-5-((6-methylpyridin-3-yl)ethynyl)-N-(piperidin-3-yl)-3-ureidothiophene-2-carboxamide

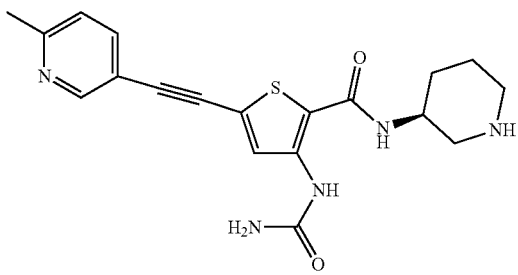 [SMILES: Cc1ccc(C#Cc2cc(NC(N)=O)c(C(=O)N[C@H]3CCCNC3)s2)cn1]

A target compound was obtained by applying the method in Example 2.

$^1$H NMR (400 MHz, DMSO-d$_6$) δ 10.00 (s, 1H), 8.65 (s, 1H), 8.14 (s, 1H), 7.90 (d, 1H), 7.87 (d, 1H), 7.34 (d, 1H), 6.69 (br, 2H), 3.77 (m, 1H), 2.93 (m, 1H), 2.79 (m, 1H), 2.43 (m, 2H), 1.81 (m, 1H), 1.63 (m, 1H), 1.45 (m, 2H). MS (m/z): 384 [M+H]. t$_R$=3.849 min (HPLC Condition 1)

Example 36. Preparation of (S)—N-(piperidin-3-yl)-5-((6-(pyrrolidin-1-yl)pyridin-3-yl)ethynyl)-3-ureidothiophene-2-carboxamide

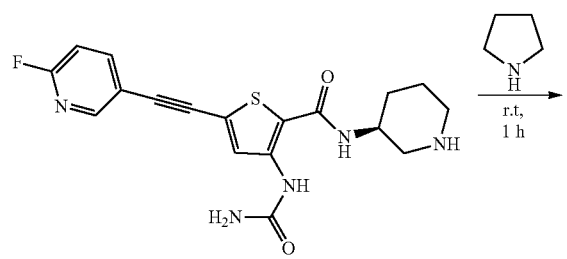

Pyrrolidine (73.4 mg, 1.032 mmol) was put into (S)-5-((6-fluoropyridin-3-yl)ethynyl)-N-(piperidin-3-yl)-3-ureidothiophene-2-carboxamide (20.0 mg, 0.052 mmol), and the resulting mixture was stirred at room temperature for 1 hour. After the reaction was completed, the product was extracted with ethyl acetate and water. The collected organic layer was washed with brine solution, dried over Na$_2$SO$_4$, and then concentrated under reduced pressure. The residue was purified with column chromatography (10% MeOH in DCM) to obtain a desired target compound (3.6 mg, yield 16%).

$^1$H NMR (400 MHz, CH$_3$OH-d$_4$) δ 8.20 (d, 1H), 7.97 (s, 1H), 7.62 (dd, 1H), 6.54 (d, 1H), 4.10-4.04 (m, 1H), 3.52-3.49 (m, 4H), 3.23-3.19 (m, 1H), 3.02 (d, 1H), 2.66-2.60 (m, 2H), 2.09-2.06 (m, 4H), 2.05-2.01 (m, 1H), 1.87-1.84 (m, 1H), 1.68-1.61 (m, 2H). MS (m/z): 439 [M+1]. t$_R$=4.119 min (HPLC Condition 1).

Example 37. Preparation of (S)-5-((6-piperidin-1-yl)pyridin-3-yl)ethynyl)-N-(piperidin-3-yl)-3-ureidothiophene-2-carboxamide

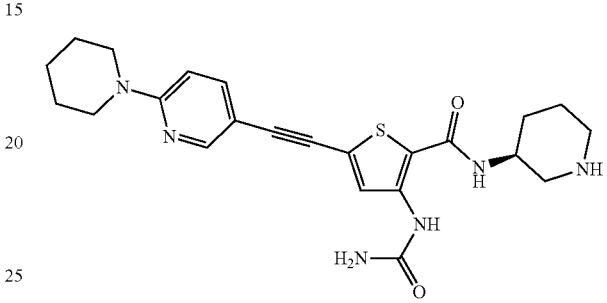

A target compound was obtained by applying the method in Example 38.

$^1$H NMR (400 MHz, CH$_3$OH-d$_4$) δ 8.24 (d, 1H), 7.98 (s, 1H), 7.61 (dd, 1H), 6.81 (d, 1H), 4.10-4.03 (m, 1H), 3.67-3.64 (m, 4H), 3.22-3.16 (m, 1H), 3.00 (d, 1H), 2.66-2.58 (m, 2H), 2.07-2.00 (m, 1H), 1.85-1.82 (m, 1H), 1.747-1.72 (m, 2H), 1.67-1.63 (m, 6H). MS (m/z): 453 [M+H]. t$_R$=4.351 min (HPLC Condition 1)

Example 38. Preparation of (S)-5-((6-morpholinopyridin-3-yl)ethynyl)-N-(piperidin-3-yl)-3-ureidothiophene-2-carboxamide

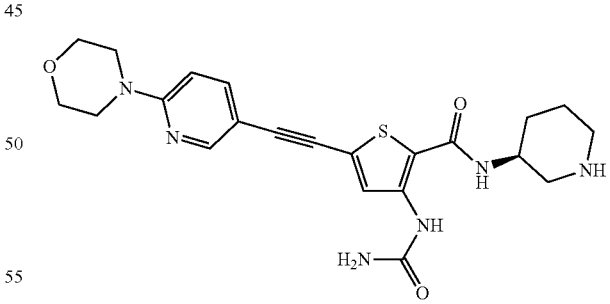

A target compound was obtained by applying the method in Example 38.

$^1$H NMR (400 MHz, CH$_3$OH-d$_4$) δ 8.29 (d, 1H), 7.99 (s, 1H), 7.67 (dd, 1H), 6.83 (d, 1H), 4.10-4.03 (m, 1H), 3.82-3.80 (m, 4H), 3.61-3.59 (m, 4H), 3.22-3.18 (m, 1H), 3.02 (d, 1H), 2.67-2.59 (m, 2H), 2.07-2.00 (m, 1H), 1.86-1.83 (m, 1H), 1.67-1.60 (m, 2H). MS (m/z): 455 [M+H]. t$_R$=4.479 min (HPLC Condition 1)

Example 39. Preparation of 5-((1-methyl-1H-pyrazol-4-yl)ethynyl)-N-(pyrrolidin-3-yl)-3-ureidothiophene-2-carboxamide trifluoroacetate

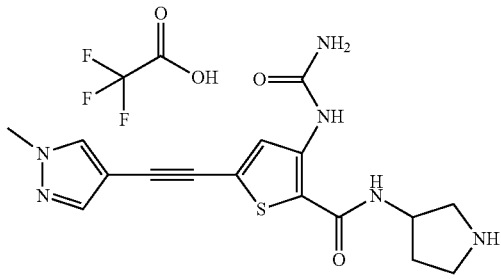

A target compound was obtained by applying the method in Example 2.

$^1$H NMR (400 MHz, DMSO-d$_6$) δ 9.88 (s, 1H), 8.73 (br s, 2H), 8.42 (br s, 1H), 8.31 (br s, 1H), 8.22 (d, 1H), 8.14 (s, 1H), 8.03 (s, 1H), 7.75 (s, 1H), 6.70 (br s, 1H), 4.49-4.44 (m, 1H), 3.85 (s, 3H), 3.24-3.23 (m, 1H), 3.16-3.15 (m, 1H), 2.19-2.14 (m, 1H), 2.03-1.98 (m, 1H). MS (m/z): 358 [m+1]. $t_R$=1.625 min (HPLC Condition 2).

Example 40. Preparation of 5-((3-fluorophenyl)ethynyl)-N-(pyrrolidin-3-yl)-3-ureidothiophene-2-carboxamide

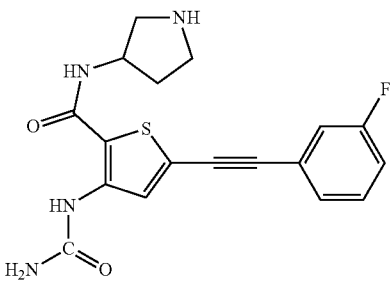 [SMILES: NC(=O)Nc1cc(C#Cc2cccc(F)c2)sc1C(=O)NC1CCNC1]

A target compound was obtained by applying the method in Example 2.

$^1$H NMR (400 MHz, DMSO-d$_6$) δ 9.89 (s, 1H), 8.77 (brs, 2H), 8.32 (s, 1H), 8.18 (s, 1H), 7.53-7.36 (m, 3H), 7.34 (t, 1H), 6.77 (brs, 1H), 4.51 (m, 1H), 3.45 (m, 1H), 3.36 (m, 1H), 3.28 (m, 1H), 3.19 (m, 1H), 2.21 (m, 1H), 2.08 (m, 1H). MS (m/z): 373 [M+1]. $t_R$=5.08 min (HPLC Condition 1).

Example 41. Preparation of (S)—N-(azepan-3-yl)-5-((1-methyl-1H-pyrazol-4-yl)ethynyl)-3-ureidothiophene-2-carboxamide trifluoroacetate

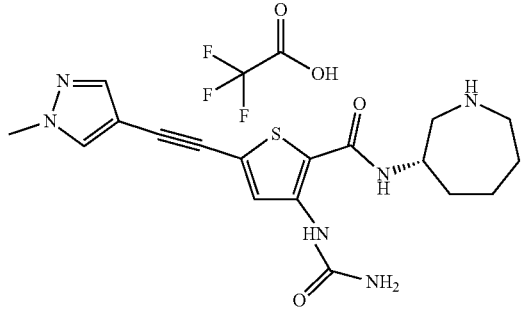

A target compound was obtained by applying the method in Example 2.

$^1$H NMR (400 MHz, DMSO-d$_6$) δ 9.88 (s, 1H), 8.77 (br s, 2H), 8.14-8.10 (m, 2H), 8.02 (s, 1H), 7.74 (s, 1H), 6.69 (br s, 1H), 4.23-4.20 (m, 1H), 3.85 (s, 3H), 3.30-3.27 (m, 1H), 3.15-3.10 (m, 3H), 1.95-1.65 (m, 5H), 1.55-1.50 (m, 1H). MS (m/z): 386 [m+1]. $t_R$=1.755 min (HPLC Condition 2).

Example 42. Preparation of (S)-5-((1H-pyrazol-4-yl)ethynyl)-N-(azepan-3-yl)-3-ureidothiophene-2-carboxamide trifluoroacetate

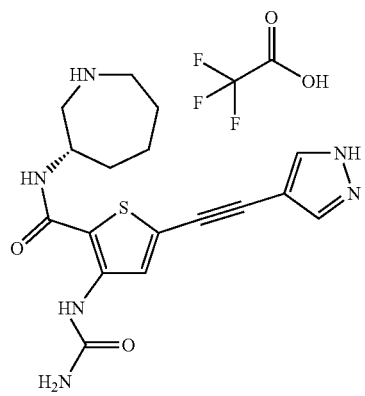

A target compound was obtained by applying the method in Example 2.

$^1$H NMR (400 MHz, DMSO-d$_6$) δ 9.89 (s, 1H), 8.77 (br s, 2H), 8.11 (d, 1H), 8.03 (s, 1H), 6.69 (br s, 1H), 4.25-4.20 (m, 1H), 3.16-3.11 (m, 3H), 1.94-1.68 (m, 5H), 1.68-1.48 (m, 1H). MS (m/z): 372 [m+1]. $t_R$=1.772 min (HPLC Condition 2).

Example 43. Preparation of (S)—N-(azepan-3-yl)-5-((1-ethyl-1H-pyrazol-4-yl)ethynyl)-3-ureidothiophene-2-carboxamide trifluoroacetate

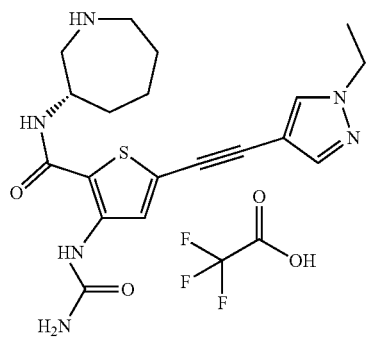

A target compound was obtained by applying the method in Example 2.

$^1$H NMR (400 MHz, DMSO-d$_6$) δ 9.90 (s, 1H), 8.80 (br s, 2H), 8.22 (s, 1H), 8.14 (d, 1H), 8.04 (s, 1H), 7.77 (s, 1H), 6.71 (br s, 1H), 4.26-4.21 (m, 1H), 4.16 (q, 2H), 3.32-3.29 (m, 1H), 3.17-3.12 (m, 3H), 1.97-1.69 (m, 5H), 1.57-1.51 (m, 1H), 1.38 (t, 3H). MS (m/z): 400 [m+1]. $t_R$=1.782 min (HPLC Condition 2).

Example 44. Preparation of (S)—N-(azepan-3-yl)-5-((1-isopropyl-1H-pyrazol-4-yl)ethynyl)-3-ureidothiophene-2-carboxamide trifluoroacetate

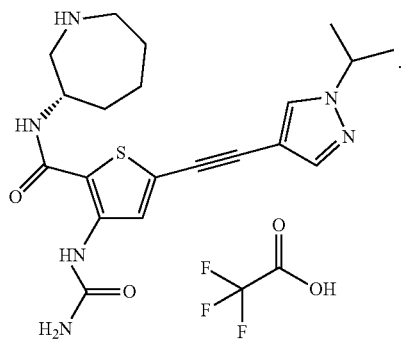 [SMILES: CC(C)n1cc(C#Cc2cc(NC(N)=O)c(C(=O)N[C@H]3CCCCNC3)s2)cn1 ; O=C(O)C(F)(F)F]

A target compound was obtained by applying the method in Example 2.

$^1$H NMR (400 MHz, DMSO-$d_6$) δ 9.91 (s, 1H), 8.85 (br s, 1H), 8.81 (br s, 1H), 8.26 (s, 1H), 8.15 (d, 1H), 8.04 (s, 1H), 7.77 (s, 1H), 6.72 (br s, 1H), 4.56-4.49 (m, 1H), 4.26-4.21 (m, 1H), 3.32-3.12 (m, 4H), 1.97-0.86 (m, 6H), 0.83 (d, 6H). MS (m/z): 414 [m+1]. $t_R$=1.889 min (HPLC Condition 2).

Example 45. Preparation of (S)—N-(azepan-3-yl)-5-((1-(2-methoxyethyl)-1H-pyrazol-4-yl)ethynyl)-3-ureidothiophene-2-carboxamide trifluoroacetate

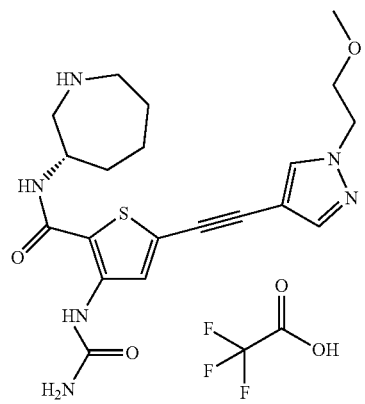 [SMILES: COCCn1cc(C#Cc2cc(NC(N)=O)c(C(=O)N[C@H]3CCCCNC3)s2)cn1 ; O=C(O)C(F)(F)F]

A target compound was obtained by applying the method in Example 2.

$^1$H NMR (400 MHz, DMSO-$d_6$) δ 9.87 (s, 1H), 8.79 (br s, 1H), 8.76 (br s, 1H), 8.15-8.10 (m, 2H), 8.01 (s, 1H), 7.76 (s, 1H), 6.68 (br s, 1H), 4.27-4.20 (m, 3H), 3.66 (t, 2H), 3.29-3.26 (m, 2H), 3.20-3.09 (m, 7H), 1.97-1.15 (m, 6H). MS (m/z): 430 [m+1]. $t_R$=1.742 min (HPLC Condition 2).

Example 46. Preparation of (S)—N-(azepan-3-yl)-5-((1-(tetrahydro-2H-pyran-4-yl)-1H-pyrazol-4-yl)ethynyl)-3-ureidothiophene-2-carboxamide trifluoroacetate

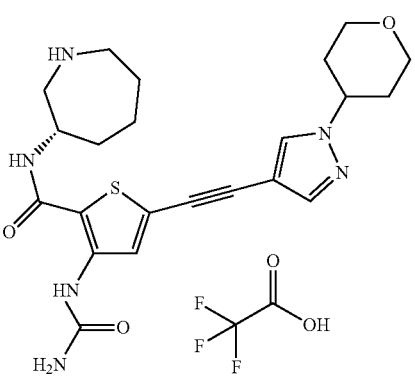 [SMILES: NC(=O)Nc1cc(C#Cc2cnn(C3CCOCC3)c2)sc1C(=O)N[C@H]1CCCCNC1 ; O=C(O)C(F)(F)F]

A target compound was obtained by applying the method in Example 2.

$^1$H NMR (400 MHz, DMSO-$d_6$) δ 9.88 (s, 1H), 8.77 (br s, 2H), 8.28 (s, 1H), 8.12 (d, 1H), 8.02 (s, 1H), 7.79 (s, 1H), 6.69 (br s, 1H), 4.47-4.39 (m, 1H), 4.23-4.19 (m, 1H), 3.96-3.93 (m, 2H), 3.31-3.27 (m, 1H), 3.16-3.10 (m, 3H), 2.07-1.65 (m, 10H), 1.55-1.22 (m, 1H). MS (m/z): 456 [m+1]. $t_R$=1.789 min (HPLC Condition 2).

Example 47. Preparation of (S)—N-(azepan-3-yl)-5-((1-(1-(methylsulfonyl)piperidin-4-yl)-1H-pyrazol-4-yl)ethynyl)-3-ureidothiophene-2-carboxamide trifluoroacetate

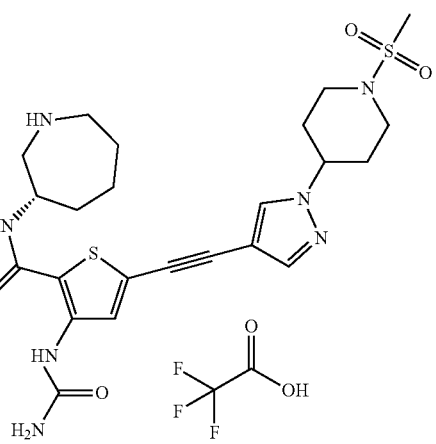

A target compound was obtained by applying the method in Example 2.

$^1$H NMR (400 MHz, DMSO-$d_6$) δ 9.89 (s, 1H), 8.78 (br s, 2H), 8.32 (s, 1H), 8.12 (d, 1H), 8.03 (s, 1H), 7.80 (s, 1H), 6.70 (br s, 1H), 4.39-4.32 (m, 1H), 4.27-4.18 (m, 1H), 3.66-3.63 (m, 3H), 3.31-3.08 (m, 6H), 2.95-2.88 (m, 5H), 2.14-2.10 (m, 2H), 2.00-1.65 (m, 8H), 1.56-1.50 (m, 1H). MS (m/z): 533 [m+1]. $t_R$=1.789 min (HPLC Condition 2).

Example 48. Preparation of (S)—N-(azepan-3-yl)-5-(thiophen-3-ylethynyl)-3-ureidothiophene-2-carboxamide trifluoroacetate

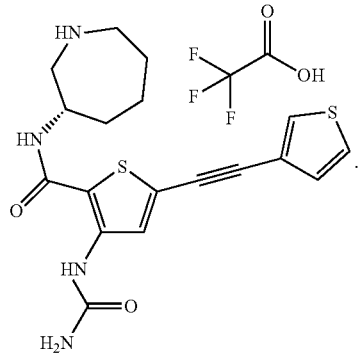

A target compound was obtained by applying the method in Example 2.

¹H NMR (400 MHz, DMSO-d₆) δ 9.88 (s, 1H), 8.80 (br s, 1H), 8.77 (br s, 1H), 8.15 (d, 1H), 8.09 (s, 1H), 8.02-8.01 (m, 1H), 7.69-7.67 (m, 1H), 7.31-7.29 (m, 1H), 6.71 (br s, 1H), 4.25-4.19 (m, 1H), 3.31-3.08 (m, 4H), 1.96-1.65 (m, 5H), 1.56-1.48 (m, 1H). MS (m/z): 388 [m+1]. $t_R$=1.969 min (HPLC Condition 2).

Example 49. Preparation of (S)-5-((1-(1-acetylpiperidin-4-yl)-1H pyrazol-7-yl)othynyl)-N-(azepan-3-yl)-3-ureidothiophene-2-carboxamide trifluoroacetate

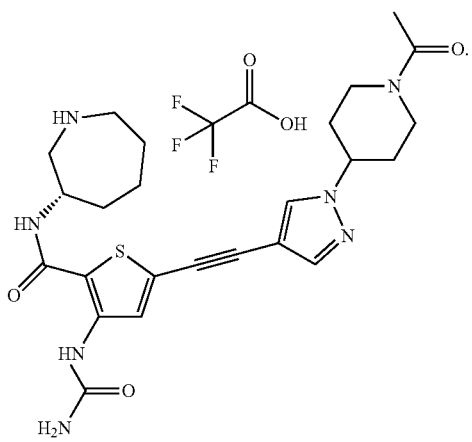

A target compound was obtained by applying the method in Example 2.

¹H NMR (400 MHz, DMSO-d₆) δ 9.88 (s, 1H), 8.74 (br s, 2H), 8.27 (s, 1H), 8.11 (d, 1H), 8.03 (s, 1H), 7.78 (s, 1H), 6.69 (br s, 1H), 4.48-4.42 (m, 2H), 4.24-4.20 (m, 1H), 3.92-3.89 (m, 1H), 3.27-3.07 (m, 7H), 2.73-2.67 (m, 1H), 2.03-1.87 (m, 4H), 1.86-1.78 (m, 5H), 1.76-1.65 (m, 4H), 1.56-1.48 (m, 1H). MS (m/z): 497 [m+1]. $t_R$=1.732 min (HPLC Condition 2).

Example 50. Preparation of (S)-5-((1-(1-acetylpiperidin-4-yl)-1H-pyrazol-4-yl) ethynyl)-N-(azepan-3-yl)-3-ureidothiophene-2-carboxamide

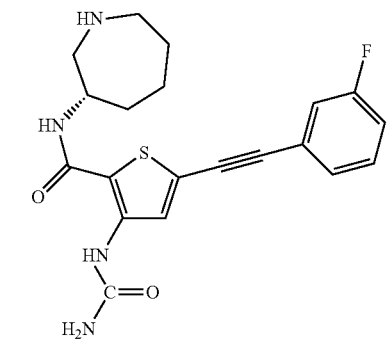 [SMILES: NC(=O)Nc1cc(C#Cc2cccc(F)c2)sc1C(=O)N[C@H]1CCCCNC1]

A target compound was obtained by applying the method in Example 2.

¹H NMR (400 MHz, DMSO-d₆) δ 9.88 (s, 1H), 8.79 (brs, 2H), 8.20 (d, 1H), 8.17 (s, 1H), 7.53 (m, 3H), 7.32 (t, 1H), 6.73 (brs, 2H), 4.25 (m, 1H), 3.32 (m, 2H), 3.16 (m, 4H), 1.83 (m, 1H), 1.75-1.55 (m, 4H), 1.52 (m, 1H). 401 [M+1]. $t_R$=5.26 min (HPLC Condition 1).

Example 51. Preparation of 5-(2-(1-methyl-1H-pyrazol-4-yl)ethyl)-N-(pyrrolidin-3-yl)-3-ureidothiophene-2-carboxamide trifluoroacetate

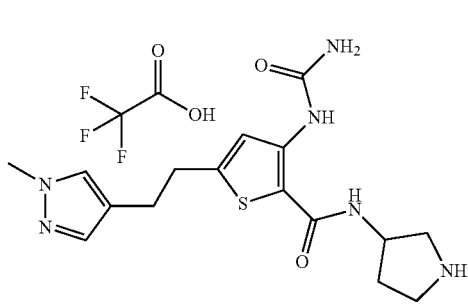

Pd/C (7 Mg, 6.58 umol) and methanol (8 mL) were put into the 5-((1-methyl-1H-pyrazol-4-yl)ethynyl)-N-(pyrrolidin-3-yl)-3-ureidothiophene-2-carboxamide (78 mg, 0.218 mmol) synthesized in Example 39, and the resulting mixture was stirred at room temperature under a hydrogen gas for 2 hours. The reaction mixture was filtered with Celite and concentrated under reduced pressure to obtain 44 mg (55.8%) of a target compound.

MS (m/z): 362 [M+1]. $t_R$=1.462 min (HPLC Condition 2).

Example 52. Preparation of (S)—N-(azepan-3-yl)-5-(2-(1-methyl-1H-pyrazol-4-yl)ethyl)-3-ureidothiophene-2-carboxamide trifluoroacetate

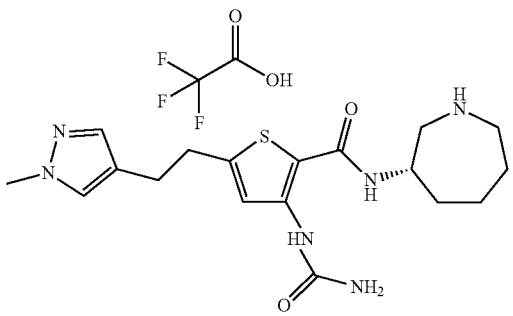

A target compound was obtained by applying the method in Example 51.
$^1$H NMR (400 MHz, DMSO-$d_6$) δ 9.98 (s, 1H), 7.70-7.65 (m, 2H), 7.48 (s, 1H), 7.26 (s, 1H), 6.57 (br s, 1H), 4.14-4.00 (m, 1H), 3.75 (s, 3H), 3.04-2.90 (m, 6H), 2.73 (t, 2H), 1.82-1.47 (m, 6H). MS (m/z): 390 [M+1]. $t_R$=1.599 min (HPLC Condition 2).

Example 53. Preparation of (S)-5-(3-fluorophenethyl))-N-(piperidin-3-yl)-3-ureidothiophene-2-carboxamide

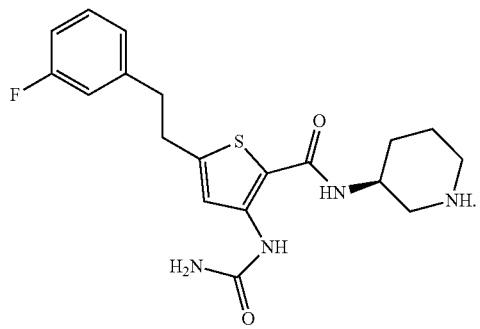 [SMILES: NC(=O)Nc1cc(CCc2cccc(F)c2)sc1C(=O)N[C@H]1CCCNC1]

A target compound was obtained by applying the method in Example 51.
$^1$H NMR (400 MHz, DMSO-$d_6$) δ 9.92 (s, 1H), 8.70 (br s, 2H), 7.73 (s, 1H), 7.14 (q, 1H), 7.05 (m, 2H), 7.02 (m, 1H), 6.60 (br s, 1H), 4.09 (m, 1H), 3.27 (m, 2H), 3.19 (t, 2H), 2.96 (t, 2H), 2.82 (m, 2H), 1.84 (m, 2H), 1.67 (m, 2H). 391 [M+1]. $t_R$=4.97 min (HPLC Condition 1).

Example 54. Preparation of (S)—N-(azepan-3-yl)-5-(3-fluorophenethyl)-3-ureidothiophene-2-carboxamide

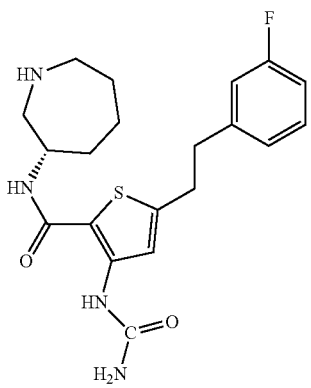 [SMILES: NC(=O)Nc1cc(CCc2cccc(F)c2)sc1C(=O)N[C@H]1CCCCNC1]

A target compound was obtained by applying the method in Example 51.
$^1$H NMR (400 MHz, DMSO-$d_6$) δ 9.91 (s, 1H), 8.87 (br s, 2H), 7.87 (d, 1H), 7.73 (s, 1H), 7.35 (m, 1H), 7.14 (m, 2H), 7.05 (t, 1H), 6.60 (br s, 2H), 4.23 (m, 1H), 3.25 (m, 2H), 3.16 (m, 4H), 2.96 (m, 2H), 1.91-1.67 (m, 5H), 1.53 (m, 1H). 405 [M+1]. $t_R$=5.09 min (HPLC Condition 1).

Example 55. Preparation of 5-(3-fluorophenethyl)-N-(pyrrolidin-3-yl)-3-ureidothiophene-2-carboxamide

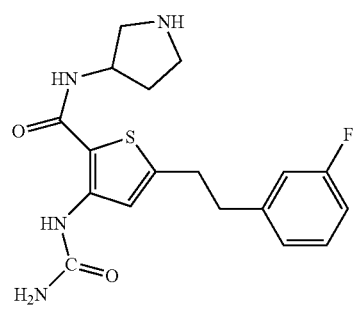 [SMILES: NC(=O)Nc1cc(CCc2cccc(F)c2)sc1C(=O)NC1CCNC1]

A target compound was obtained by applying the method in Example 51.
$^1$H NMR (400 MHz, DMSO-$d_6$) δ 9.92 (s, 1H), 8.82 (br s, 2H), 8.01 (d, 1H), 7.74 (s, 1H), 7.35 (m, 1H), 7.14 (m, 2H), 7.04 (m, 2H), 6.61 (br s, 1H), 4.49 (m, 1H), 4.03 (m, 1H), 3.42-3.31 (m, 3H), 3.17 (m, 3H), 2.96 (m, 2H), 2.17 (m, 1H), 1.99 (m, 1H). 377 [M+1]. $t_R$=4.91 min (HPLC Condition 1).

EXPERIMENTAL EXAMPLES

Experimental Example 1. Measurement of Kinase Inhibitory Activity

In order to measure inhibitory activity (% inhibitory ability) against a protein kinase with respect to the compound of the present invention, a biochemical assay was performed in a full kinase panel shown in the following Table 1. As an experimental compound, the (S)-5-((3-fluorophenyl)ethynyl)-N-(piperidin-3-yl)-3-ureidothiophene-2-carboxamide synthesized in Example 24 was used.

The following Table 1 shows results of measuring the inhibitory efficacy against kinase when the experimental compound was treated at a single concentration of 1 μM.

TABLE 1

| Kinase | %Inhibitory ability |
|---|---|
| AAK1 | 80 |
| ANKK1 | 93.3 |
| AURKB | 66 |
| AXL | 87 |
| BIKE | 77 |
| BLK | 93.2 |
| BUB1 | 97.4 |
| CAMK1 | 67 |
| CHEK1 | 96.1 |
| CHEK2 | 100 |
| CSF1R | 98.4 |
| CSK | 92.1 |
| DAPK1 | 94.4 |

TABLE 1-continued

| Kinase | %Inhibitory ability |
|---|---|
| DAPK2 | 88 |
| DAPK3 | 84 |
| DCAMKL1 | 80 |
| DLK | 68 |
| DRAK1 | 99.5 |
| DRAK2 | 96 |
| EGFR(T790M) | 85 |
| EPHA3 | 80 |
| FAK | 75 |
| FGR | 94.1 |
| FLT3 | 99.6 |
| FLT4 | 94.5 |
| FYN | 91.5 |
| GAK2 | 73 |
| HCK | 94.9 |
| HPK1 | 78 |
| IRAK1 | 90.7 |
| IRAK4 | 99.8 |
| JAK2 | 83 |
| JAK3 | 91.1 |
| KIT | 99.8 |
| LCK | 72 |
| LOK | 71 |
| LRRK2 | 72 |
| MAP3K2 | 97.7 |
| MAP3K3 | 94.6 |
| MAP4K2 | 92.7 |
| MAP4K3 | 69 |
| MAP4K4 | 91.4 |
| MAP4K5 | 85 |
| MAPKAPK5 | 82 |
| MARK2 | 79 |
| MEK1 | 96.3 |
| MEK2 | 93.3 |
| MEK3 | 83 |
| MEK5 | 99.9 |
| MERTK | 96.1 |
| MINK | 97.1 |
| MKNK2 | 92.7 |
| MLK1 | 95.9 |
| MLK3 | 90.8 |
| MST1 | 96.6 |
| MST2 | 92.5 |
| MST4 | 83 |
| OSR1 | 68 |
| PAK4 | 92.2 |
| PAK6 | 90.3 |
| PDGFRA | 95.8 |
| PDGFRB | 99.9 |
| PHKG1 | 98.4 |
| PHKG2 | 89 |
| PIP5K2B | 74 |
| PLK4 | 81 |
| PRKG2 | 96.6 |
| PRKX | 73 |
| RET | 98.7 |
| RIOK1 | 77 |
| RIOK3 | 79 |

TABLE 1-continued

| Kinase | %Inhibitory ability |
|---|---|
| RIPK4 | 97.6 |
| SBK1 | 66 |
| SIK | 80 |
| SIK2 | 73 |
| SRC | 98.1 |
| SRPK1 | 83 |
| SYK | 91.5 |
| TAK1 | 91.5 |
| TGFBR2 | 72 |
| TNIK | 96.3 |
| TRKA | 100 |
| TRKB | 97.2 |
| TSSK3 | 72 |
| TXK | 83 |
| ULK1 | 99.8 |
| ULK2 | 99.7 |
| VEGFR2 | 73 |
| YANK1 | 95.5 |
| YANK2 | 76 |
| ZAP70 | 63 |

Experimental Example 2. Measurement of Inhibitory Activity Against Ba/F3 Cell Line A Ba/F3 cell line expressing an FLT3 mutation gene was cultured in a culture solution including 90% RPMI, 10% FBS, and an antibiotic (Welgene). 100 uL of the Ba/F3 cell line was put into each of 5,000 wells of a TC-treated 96 well plate (SPL), and then 1 uL of a test compound diluted in dimethylsulfoxide (diluted for each 3 paint from a concentration of 1 mM, total 10 concentrations) was each injected thereinto. Thereafter, the resulting cell lines were incubated in a cell culture incubator for 72 hours. 50 uL of a cell titer glo (Promega) solution was added thereto, the resulting mixture was stored at room temperature for 10 minutes, and then the light emission intensity was measured by using a reader (Envision, PerkinElmer). The light emission intensity was shown as a graph for each final concentration of the test compound, and the $GI_{50}$ value was obtained by using a Prism 5.0 (GraphPad) software.

A parental Ba/F3 cell line having no FLT3 mutation gene was cultured by using a culture solution supplemented with mouse IL-3 (R&D Systems), such that a final concentration became 1 ng/mL in the culture solution including 90% RPMI, 10% FBS, and an antibiotic (Welgene). The activity was measured by a method which is the same as described above.

The following Table 2 shows the results of measuring growth inhibitory activity of each experimental compound against Parental Ba/F3, FLT3-ITD, FLT3-ITD-F691L, FLT3-D835Y, and FLT3-ITD-F691L-D835Y cells.

TABLE 2

| | $IC_{50}$ (uM) | | | | |
|---|---|---|---|---|---|
| Experimental compound | Parental Ba/F3 | FLT3-ITD | FLT3-ITD-F691L | FLT3-D835Y | FLT3-ITD-F691L-D835Y |
| Example 2 | 0.159 | <0.001 | 0.004 | 0.002 | <0.001 |
| Example 3 | 6.46 | <0.005 | 0.099 | 0.050 | <0.004 |
| Example 4 | 24 | 0.016 | 1.10 | 0.408 | 0.010 |
| Example 5 | 2.06 | <0.005 | 0.062 | 0.039 | <0.004 |
| Example 6 | 1.59 | <0.005 | 0.055 | 0.041 | <0.004 |
| Example 7 | 1.86 | <0.005 | 0.089 | 0.070 | <0.004 |
| Example 8 | 0.360 | 0.001 | 0.013 | 0.010 | <0.001 |
| Example 9 | 0.429 | <0.001 | 0.005 | 0.003 | <0.001 |
| Example 10 | 4.622 | 0.005 | 0.066 | 0.041 | 0.004 |

TABLE 2-continued

| Experimental compound | Parental Ba/F3 | FLT3-ITD | FLT3-ITD-F691L | FLT3-D835Y | FLT3-ITD-F691L-D835Y |
|---|---|---|---|---|---|
| | | | IC$_{50}$ (uM) | | |
| Example 11 | 0.143 | <0.001 | 0.004 | 0.003 | <0.001 |
| Example 12 | >10.0 | 0.037 | 0.487 | 0.289 | 0.027 |
| Example 13 | 2.223 | 0.002 | 0.022 | 0.014 | 0.004 |
| Example 14 | 0.269 | <0.001 | 0.009 | 0.005 | <0.001 |
| Example 15 | 34.60 | 0.028 | 0.216 | 0.268 | 0.009 |
| Example 16 | 14.8 | 0.006 | 0.335 | 0.197 | 0.004 |
| Example 17 | 2.37 | <0.005 | 0.069 | 0.064 | <0.004 |
| Example 18 | 0.454 | 0.003 | 0.023 | 0.011 | <0.001 |
| Example 21 | 2.78 | <0.005 | 0.087 | 0.041 | <0.004 |
| Example 22 | 3.647 | 0.007 | 0.032 | 0.052 | <0.001 |
| Example 23 | >5.0 | 0.007 | 0.267 | 0.180 | 0.02 |
| Example 24 | 1.295 | 0.005 | 0.058 | 0.039 | 0.002 |
| Example 39 | >100 | 3.726 | 19.11 | 33.99 | 1.239 |
| Example 40 | 14.89 | 0.164 | 0.848 | 0.925 | 0.079 |
| Example 41 | 3.69 | 0.013 | 0.078 | 0.092 | 0.007 |
| Example 42 | 54.4 | 0.137 | 5.23 | 4.01 | 0.116 |
| Example 43 | 4.1 | 0.01 | 0.2 | 0.3 | 0.006 |
| Example 44 | 2.45 | 0.006 | 0.214 | 0.216 | 0.004 |
| Example 45 | 16.8 | 0.038 | 1.34 | 0.841 | 0.019 |
| Example 46 | 0.3 | 0.003 | 0.075 | 0.042 | 0.003 |
| Example 47 | >5.0 | 0.027 | 0.645 | 0.533 | 0.040 |
| Example 48 | 1.594 | 0.005 | 0.083 | 0.067 | 0.004 |
| Example 49 | >5.0 | 0.017 | 0.616 | 0.437 | 0.031 |
| Example 50 | 7.80 | 0.023 | 0.174 | 0.228 | 0.006 |
| Example 52 | >100 | 6.275 | >100 | >33 | >4 |
| Example 53 | 44.46 | 0.359 | 1.391 | 1.613 | 0.149 |
| Example 54 | >33 | 1.933 | 7.467 | 11.49 | 1.021 |

Meanwhile, the novel compound represented by Chemical Formula 1 according to the present invention can be formulated in various forms according to the purpose. The followings illustrate several formulation methods in which the compound represented by Chemical Formula 1 according to the present invention is contained as an active ingredient, and the present invention is not limited thereto.

Experimental Example 3. In Vivo Efficacy in Mouse Acute Myeloid Leukemia Model Bearing Ba/F3 (ITD,F691L,D835Y) Cell Line 3-1. Protocol Description
Ba/F3 Cell Culture Ba/F3 cell lines transformed with each FLT3 mutant was cultured in 90% RPMI, 10% FBS (Welgene), supplemented with penicillin and streptomycin. For culturing parental Ba/F3 cells, recombinant mouse IL-3 (R&D Systems) was added to the culture media as extra supplement.

Establishment of Mouse Acute Myeloid Leukemia (AML) Model

Nude mice (5-6 weeks old)(Orient) were purchased and used after a week. Mice were anesthetized following IACUC approved animal protocol. FLT3-ITD F691L-D835Y, luc+ Ba/F3 cell (Established in-house) suspension (in 0.1 mL RPMI1640 (Welgene) of 1.0×106 cells) was injected into tail vein intravenously using a 29-G needle, and an tail mark was added to each animal for identification. After 6 days, the luminescence intensity was measured using IVIS (Perkin Elmer) to calculate the ROI intensity. Once ROI intensity reaches the study-desired minimum intensity (usually 2×106), mice were randomized into different treatment groups based on signal intensity.

Drug Administration for Po

Each compound was dissolved in NMP at 20× final concentration and diluted to 1× with the remaining vehicle components (vehicle: 5% NMP, 15% solutol (Sigma-aldrich), 30% PEG400 (Sigma-aldrich), 50% 0.05M citric acid (Sigma-aldrich)). Each compound solution was prepared freshly just before administration. Compounds were administered orally using a mouse sondae once a day, 0.1 mL per mouse. Mice were humanely euthanized if animals experience 20% body weight loss.

Measurement of In Vivo Luminescence

D-Luciferin (Promega) was dissolved in DPBS (Welgene) (without Ca2+ and Mg2+) at 15 mg/mL, and the stock solution was prepared after filtration using 0.22 μm syringe filters (BD). Luciferin solution (150 mg/kg in DPBS) was injected intraperitoneally into each mouse (200 μL/mouse). After 5 min, mice were anesthetized for 5 min using isoflurane (JW Pharma). Luminescence signal was read using IVIS200 (exposure time: auto, binning: 8, F/stop: 1). Signal intensity and body weights were measured every 3 days to monitor the ROI intensity and treatment-induced body weight loss. The luminescent images were displayed in the photon mode with signal intensity expressed as average radiance (p/sec/cm2/sr). Data was analyzed using Living Image software (Caliper, PerkinElmer).

Spleen Harvest

Mice were anesthetized following IACUC approved animal protocol.

Mice were then euthanized by cervical dislocation while they were still under isoflurane anesthesia. The spleens from the mice were isolated and weighted, and spleen weight index was calculated as organ weight (mg) per gram of mouse body weight. Data was shown as mean±SD of 4 mice in each group.

Statistical Analysis

Statistical analysis of luminescence signal intensity, mouse body weight, and spleen/body weight ratio were evaluated using two-way ANOVA. Differences were considered statistically significant at $p<0.005$.

3-2. Results
In Vivo Bioluminescent Efficacy Study

Figure 1B:
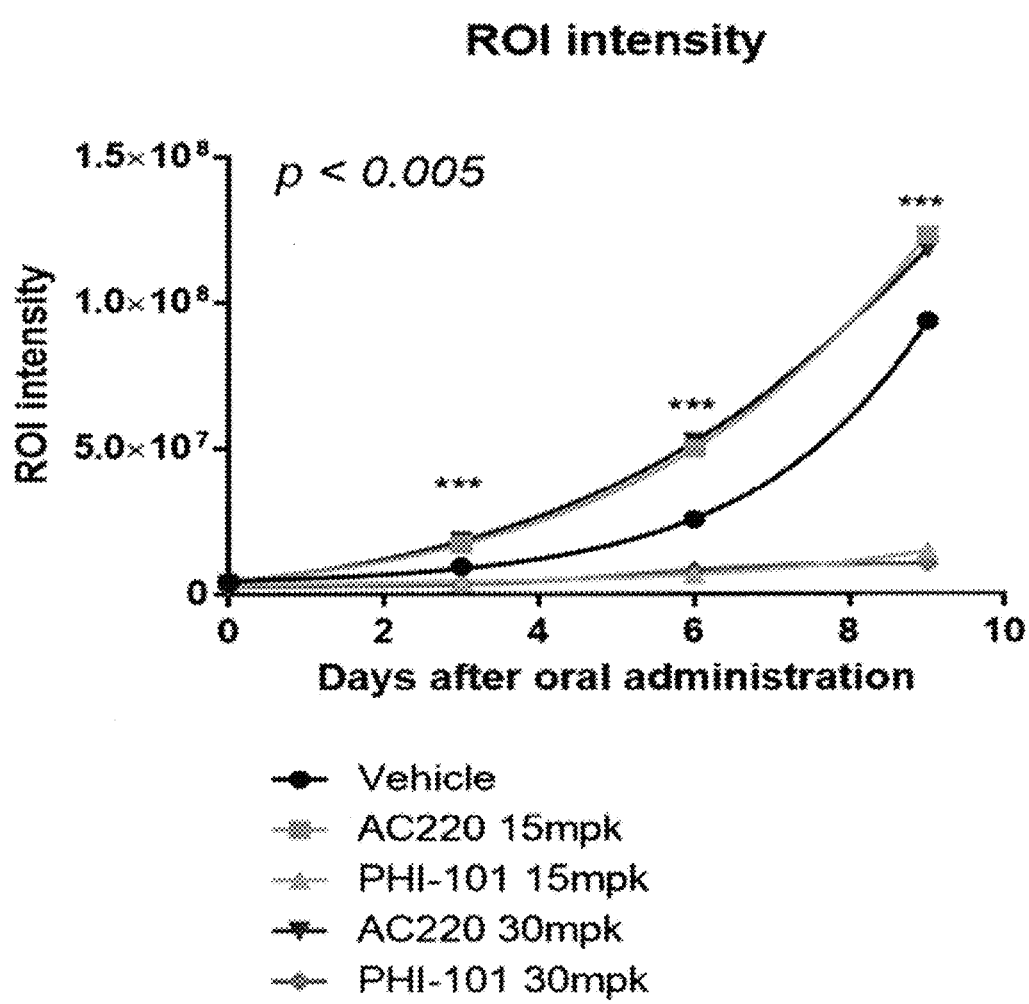
Figure 1C:
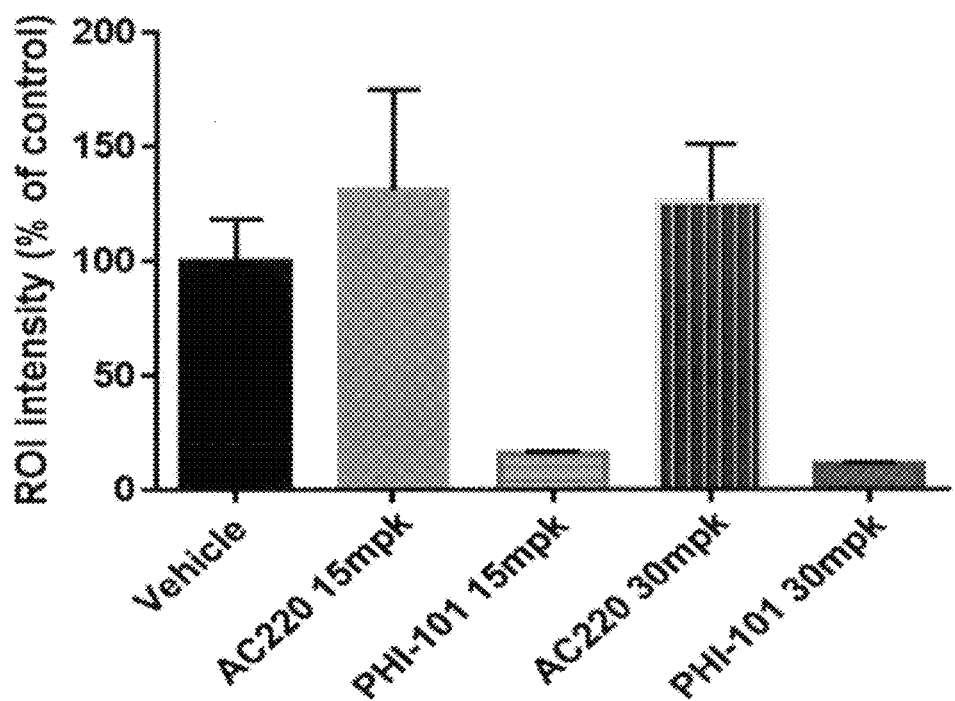
Figure 2:
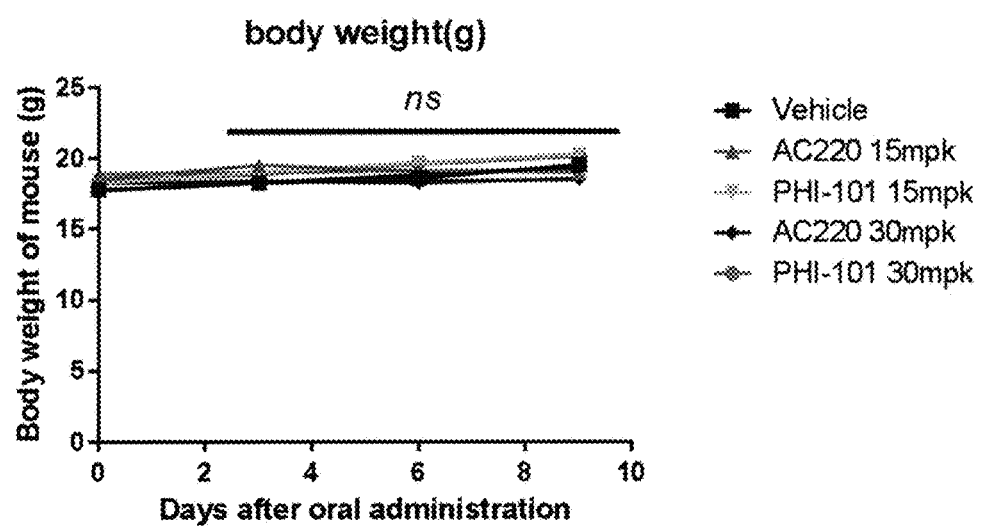
FIG. 2 illustrates the body weight change of mice during bioluminescent in vivo efficacy study (po, qd).
Figure 3A:
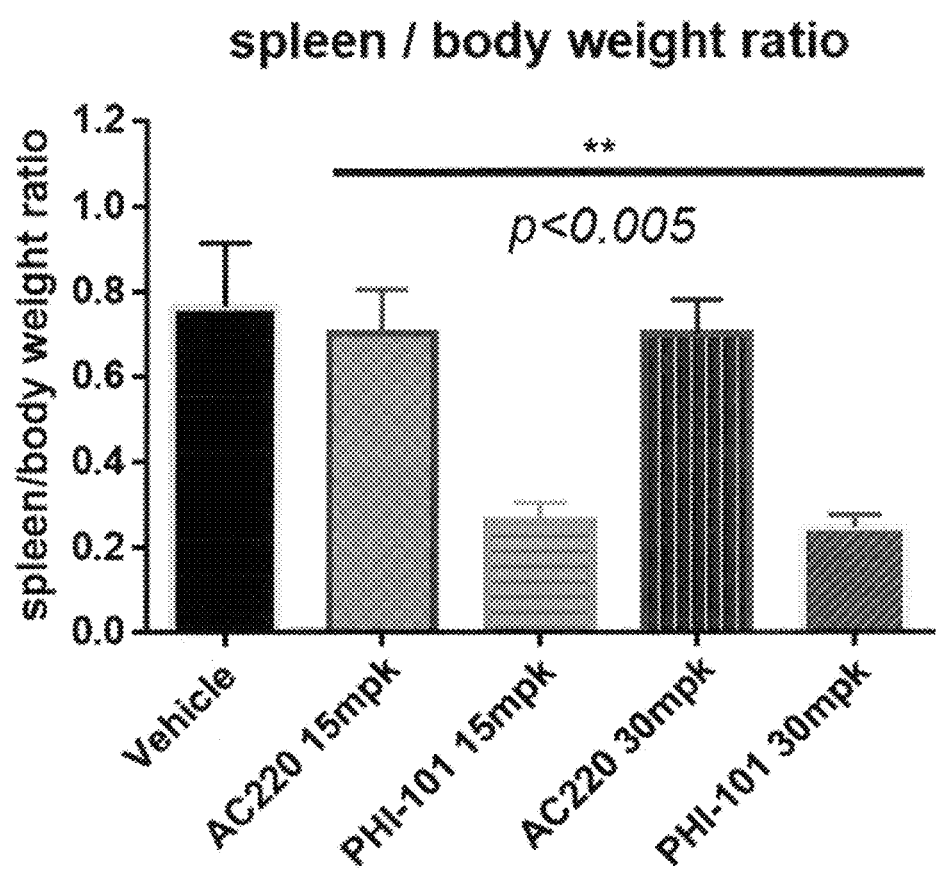
FIG. 3(a)-FIG. 3(b) illustrate the Spleen size (spleen weight over mouse body weight) in mouse AML model bearing FLT3-ITD-F691L-D835Y Ba/F3 cells. Spleens were dissected from mice after drug administration for 9 days and were enlarged compared with AC220 and vehicle control of AML model mice. P<0.005 compared to vehicle control.
Figure 3B:
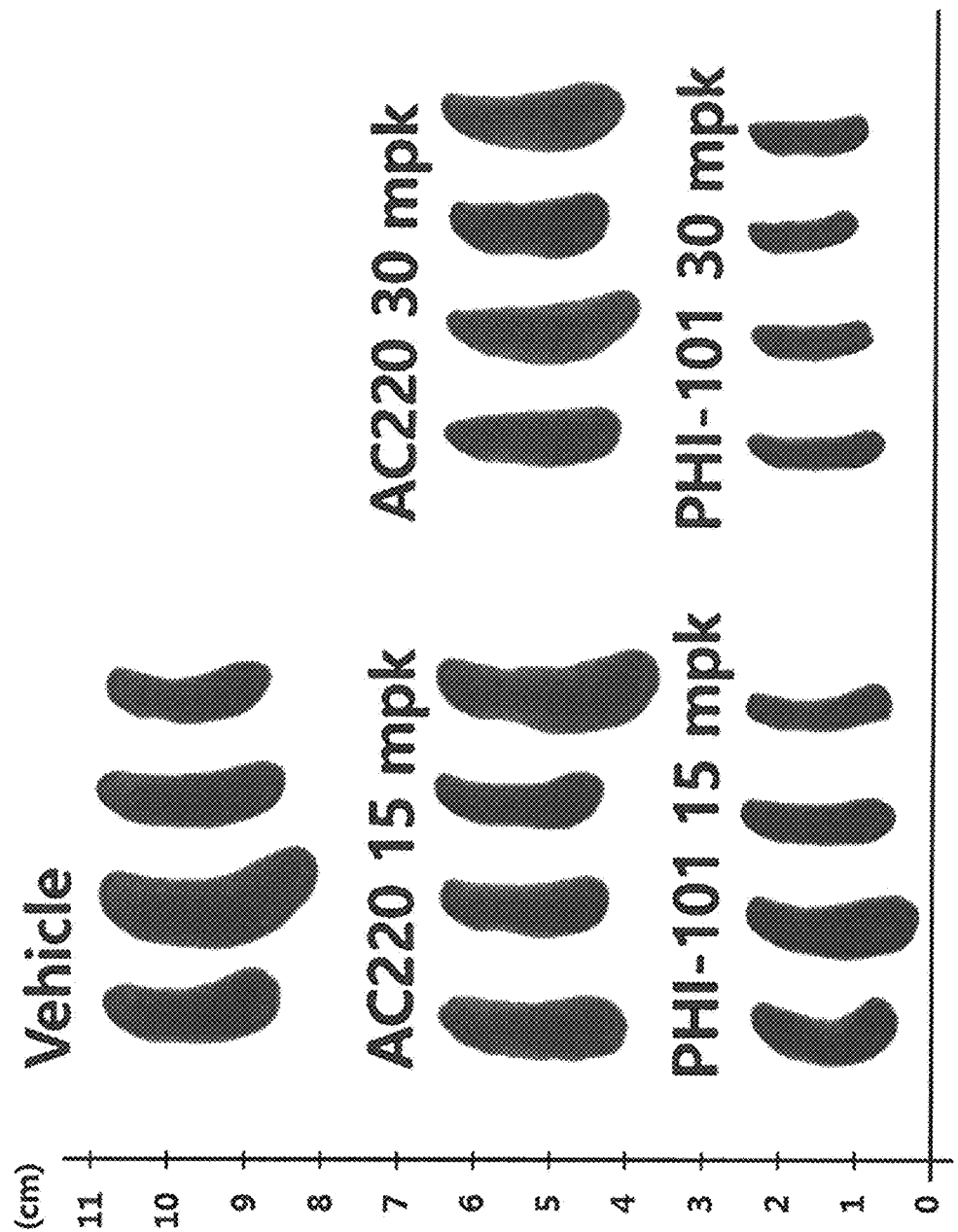

The luminescence from the mice that were orally administered with 15 or 30 mg/kg of Example 22 (PHI-101) once per day was significantly (T/C 84.2% and 88.7%, respectively) reduced compared with Quizartinib (AC220)-treated mice and vehicle control mice, indicating that PHI-101 effectively inhibits tumor growth of FLT3-ITD-F691L-D835Y (triple mutant) Ba/F3 cells in vivo (FIG. 1(a)-FIG. 1(c)). PHI-101 did not alter the mouse body weight, indicating no significant toxicity of the compound (FIG. 2). PHI-101 (15, 30 mg/kg) also reduced to the disease free spleen size (FIG. 3(a)-FIG. 3(b)).

In Vivo Efficacy—Life Span Expansion

Figure 4:
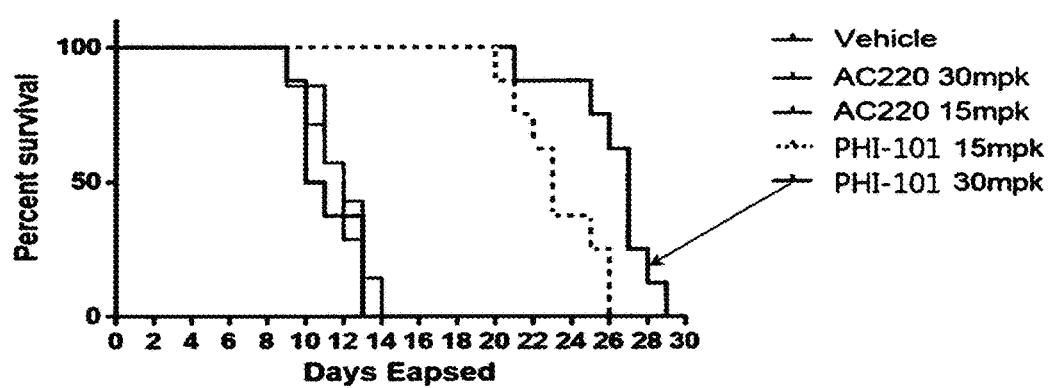
FIG. 4 illustrates the Survival curve of in vivo life-span for PHI-101 in mouse AML model bearing FLT3-ITD-F691L-D835Y Ba/F3 cells (triple mutant).

PHI-101 (po, qd, 15, 30 mg/kg) extended significantly the life-span of the mouse model of FLT3-ITD-F691L-D835Y-transformed Ba/F3 cells, whereas AC220 showed almost same life span as the vehicle control, which was consistent with the in vivo bioluminescent efficacy results. Compared with the vehicle control mice, oral administration of PHI-101 at 15 and 30 mpk extended a lifespan of mouse model as many as 26 and 29 days, respectively (FIG. 4).

| Treatment groups | Median survival |
| --- | --- |
| Vehicle | 11 |
| AC220 15 mpk | 12 |
| PHI-101 15 mpk | 23 |
| AC220 30 mpk | 13 |
| PHI-101 30 mpk | 27 |

In Vivo Bioluminescent Efficacy Study at Low Dosages

Figure 5B:
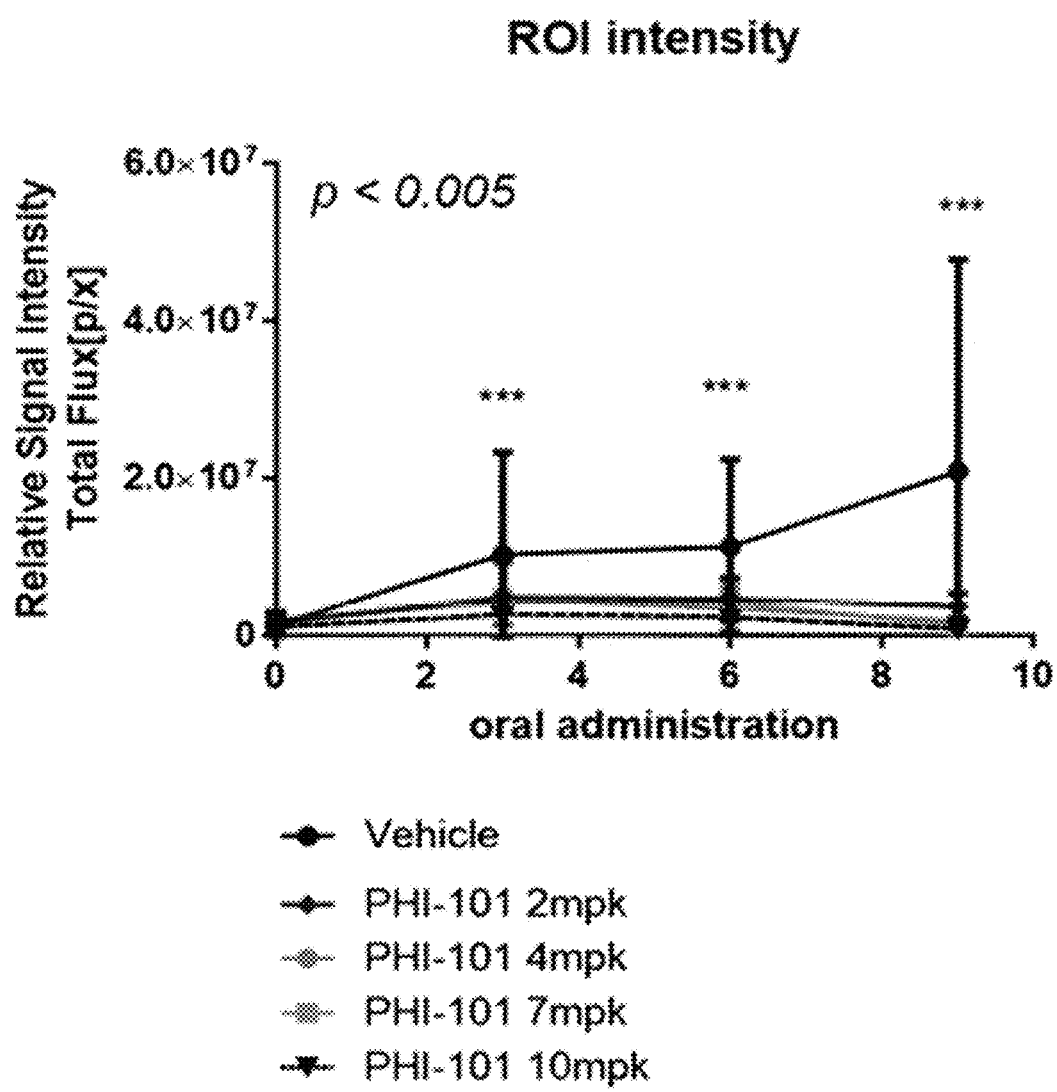
Figure 5C:
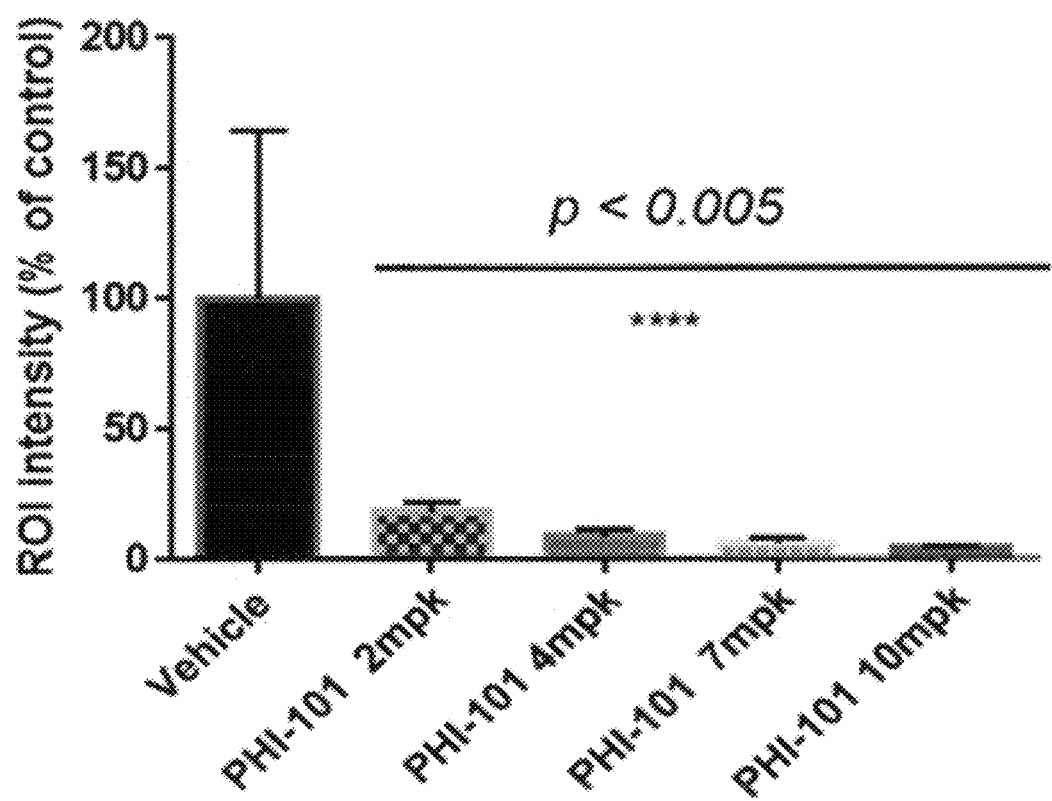

The same study as described in in vivo bioluminescent efficacy study with low dosages (2, 4, 7, 10 mg/kg) of PHI-101 showed a dose-dependent tumor inhibition in vivo from a dosage of 2 mg/kg (FIG. 5(a)-FIG. 5(c)).

Formulation Examples Method of Preparing Pharmaceutical Formulations

Formulation Example 1. Tableting (Direct Pressurization)

After 5.0 mg of the active ingredient was sieved, the active ingredient was mixed with 14.1 mg of lactose, 0.8 mg of crospovidone USNF, and 0.1 mg of magnesium stearate, and the resulting mixture was compressed to produce tablets.

Formulation Example 2. Tableting (Wet Granulation)

After 5.0 mg of the active ingredient was sieved, the active ingredient was mixed with 16.0 mg of lactose and 4.0 mg of starch. After 0.3 mg of Polysolvate 80 was dissolved in pure water, a proper amount of the resulting solution was added to the mixture, and the resulting mixture was subjected to atomization. After drying, the fine grains were sieved and then mixed with 2.7 mg of colloidal silicon dioxide and 2.0 mg of magnesium stearate. The resulting fine grains were compressed to produce tablets.

Formulation Example 3. Powder and Capsule

After 5.0 mg of the active ingredient was sieved, the active ingredient was mixed with 14.8 mg of lactose, 10.0 mg of polyvinyl pyrrolidone, and 0.2 mg of magnesium stearate. A firm No. 5 gelatin capsule was filled with the mixture by using a suitable device.

Formulation Example 4. Injection

An injection was prepared by containing 100 mg of the active ingredient, 180 mg of mannitol, 26 mg of $Na_2HPO_4 \cdot 12H_2O$, and 2,974 mg of distilled water.

What is claimed is:

1. A compound selected from the group consisting of a 2,3,5-substituted thiophene compound of Formula 1a, a pharmaceutically acceptable salt thereof, a hydrate thereof, a solvate thereof, and a stereoisomer thereof:

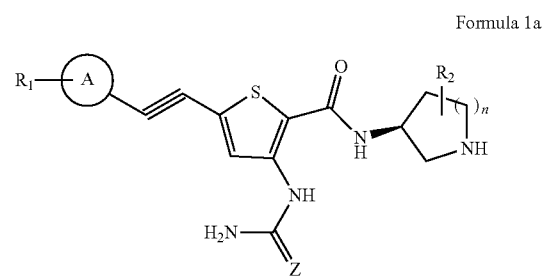

Formula 1a wherein:
Z is O;
A is a piperidinyl group, a phenyl group, a thiophenyl group, an indazolyl group, a pyridinyl group, a pyrimidinyl group, a pyrazinyl group, or a pyrazolyl group;
$R_1$ is 0 to 3 substituents independently selected from the group consisting of halo, nitro, cyano, $C_{1-6}$ alkyl, $C_{1-6}$ haloalkyl, —C(O)O—$C_{1-6}$ alkyl, —S(O)$_2$—$C_{1-6}$ alkyl, —(CH$_2$)$_m$—$C_{1-6}$ alkoxy wherein m is an integer from 1 to 6, tetrahydro-2Hpyranyl, piperidinyl, 4-(acetyl)-piperidinyl, 4-($C_{1-6}$ alkylsulfonyl)-piperidinyl, pyrrolidinyl, and morpholinyl;
$R_2$ is a hydrogen atom; and
n is an integer of from 1 to 3.

2. The compound of claim 1, wherein the compound is selected from the group consisting of:
1) ethyl (S)-4-((5-(piperidin-3-ylcarbamoyl)-4-ureidothiophen-2-yl)ethynyl)benzoate;
2) (S)-5-(phenylethynyl)-N-(piperidin-3-yl)-3-ureidothiophene-2-carboxamide;
3) (S)—N-(piperidin-3-yl)-5-(pyridin-3-ylethynyl)-3-ureidothiophene-2-carboxamide;
4) (S)—N-(piperidin-3-yl)-5-(pyridin-4-ylethynyl)-3-ureidothiophene-2-carboxamide;
5) (S)-5-((3-nitrophenyl)ethynyl)-N-(piperidin-3-yl)-3-ureidothiophene-2-carboxamide;
6) (S)-5-((3-cyanophenyl)ethynyl)-N-(piperidin-3-yl)-3-ureidothiophene-2-carboxamide;
7) (S)-5-((4-nitrophenyl)ethynyl)-N-(piperidin-3-yl)-3-ureidothiophene-2-carboxamide;
8) (S)-5-((4-chlorophenyl)ethynyl)-N-(piperidin-3-yl)-3-ureidothiophene-2-carboxamide;
9) (S)-5-((4-fluorophenyl)ethynyl)-N-(piperidin-3-yl)-3-ureidothiophene-2-carboxamide;
10) (S)—N-(piperidin-3-yl)-5-(pyridin-2-ylethynyl)-3-ureidothiophene-2-carboxamide;
11) (S)-5-((4-cyanophenyl)ethynyl)-N-(piperidin-3-yl)-3-ureidothiophene-2-carboxamide;
12) (S)-5-((1H-indazol-3-yl)ethynyl)-N-(piperidin-3-yl)-3-ureidothiophene-2-carboxamide;

13) (S)-5-((6-fluoropyridin-3-yl)ethynyl)-N-(piperidin-3-yl)-3-ureidothiophene-2-carboxamide;
14) (S)-5-((3,4-difluorophenyl)ethynyl)-N-(piperidin-3-yl)-3-ureidothiophene-2-carboxamide;
15) (S)-5-((1-methyl-1H-pyrazol-4-yl)ethynyl)-N-(piperidin-3-yl)-3-ureidothiophene-2-carboxamide;
16) (S)—N-(piperidin-3-yl)-5-((4-(trifluoromethyl)phenyl)ethynyl)-3-ureidothiophene-2-carboxamide;
17) (S)—N-(piperidin-3-yl)-5-((6-(trifluoromethyl)pyridin-3-yl)ethynyl)-3-ureidothiophene-2-carboxamide;
18) methyl (S)-4-((5-(piperidin-3-ylcarbamoyl)-4-ureidothiophen-2-yl)ethynyl)benzoate;
19) (S)-5-((6-chloropyridin-3-yl)ethynyl)-N-(piperidin-3-yl)-3-ureidothiophene-2-carboxamide;
20) (S)-5-((5-fluoropyridin-3-yl)ethynyl)-N-(piperidin-3-yl)-3-ureidothiophene-2-carboxamide;
21) (S)-5-((2-fluoropyridin-4-yl)ethynyl)-N-(piperidin-3-yl)-3-ureidothiophene-2-carboxamide;
22) (S)-5-((3-fluorophenyl)ethynyl)-N-(piperidin-3-yl)-3-ureidothiophene-2-carboxamide;
23) (S)-5-((1-(1-(methylsulfonyl)piperidin-4-yl)-1H-pyrazol-4-yl)ethynyl)-N-(piperidin-3-yl)-3-ureidothiophene-2-carboxamide;
24) (S)—N-(piperidin-3-yl)-5-(p-tolylethynyl)-3-ureidothiophene-2-carboxamide;
25) (S)-5-((3-bromo-4-cyanophenyl)ethynyl)-N-(piperidin-3-yl)-3-ureidothiophene-2-carboxamide;
26) (S)-5-((4-cyano-3-fluorophenyl)ethynyl)-N-(piperidin-3-yl)-3-ureidothiophene-2-carboxamide;
27) (S)-5-((3-fluoro-4-(trifluoromethyl)phenyl)ethynyl)-N-(piperidin-3-yl)-3-ureidothiophene-2-carboxamide;
28) (S)-5-((4-chloro-3-cyanophenyl)ethynyl)-N-(piperidin-3-yl)-3-ureidothiophene-2-carboxamide;
29) (S)-5-((2-chloropyrimidin-5-yl)ethynyl)-N-(piperidin-3-yl)-3-ureidothiophene-2-carboxamide;
30) (S)—N-(piperidin-3-yl)-5-(pyrazin-2-ylethynyl)-3-ureidothiophene-2-carboxamide;
31) (S)-5-((4-chloro-3-fluorophenyl)ethynyl)-N-(piperidin-3-yl)-3-ureidothiophene-2-carboxamide;
32) (S)-5-((3,5-difluorophenyl)ethynyl)-N-(piperidin-3-yl)-3-ureidothiophene-2-carboxamide;
33) (S)-5-((2-fluorophenyl)ethynyl)-N-(piperidin-3-yl)-3-ureidothiophene-2-carboxamide;
34) (S)-5-((2,3-difluorophenyl)ethynyl)-N-(piperidin-3-yl)-3-ureidothiophene-2-carboxamide;
35) (S)-5-((6-methylpyridin-3-yl)ethynyl)-N-(piperidin-3-yl)-3-ureidothiophene-2-carboxamide;
36) (S)—N-(piperidin-3-yl)-5-((6-(pyrrolidin-1-yl)pyridin-3-yl)ethynyl)-3-ureidothiophene-2-carboxamide;
37) (S)-5-((6-(piperidin-1-yl)pyridin-3-yl)ethynyl)-N-(piperidin-3-yl)-3-ureidothiophene-2-carboxamide;
38) (S)-5-((6-morpholinopyridin-3-yl)ethynyl)-N-(piperidin-3-yl)-3-ureidothiophene-2-carboxamide;
39) 5-((1-methyl-1H-pyrazol-4-yl)ethynyl)-N-(pyrrolidin-3-yl)-3-ureidothiophene-2-carboxamide;
40) 5-((3-fluorophenyl)ethynyl)-N-(pyrrolidin-3-yl)-3-ureidothiophene-2-carboxamide;
41) (S)—N-(azepan-3-yl)-5-((1-methyl-1H-pyrazol-4-yl)ethynyl)-3-ureidothiophene-2-carboxamide;
42) (S)-5-((1H-pyrazol-4-yl)ethynyl)-N-(azepan-3-yl)-3-ureidothiophene-2-carboxamide;
43) (S)—N-(azepan-3-yl)-5-((1-ethyl-1H-pyrazol-4-yl)ethynyl)-3-ureidothiophene-2-carboxamide;
44) (S)—N-(azepan-3-yl)-5-((1-isopropyl-1H-pyrazol-4-yl)ethynyl)-3-ureidothiophene-2-carboxamide;
45) (S)—N-(azepan-3-yl)-5-((1-(2-methoxyethyl)-1H-pyrazol-4-yl)ethynyl)-3-ureidothiophene-2-carboxamide;
46) (S)—N-(azepan-3-yl)-5-((1-(tetrahydro-2H-pyran-4-yl)-1H-pyrazol-4-yl)ethynyl)-3-ureidothiophene-2-carboxamide;
47) (S)—N-(azepan-3-yl)-5-((1-(1-methylsulfonyl)piperidin-4-yl)-1H-pyrazol-4-yl)ethynyl)-3-ureidothiophene-2-carboxamide;
48) (S)—N-(azepan-3-yl)-5-(thiophen-3-ylethynyl)-3-ureidothiophene-2-carboxamide;
49) (S)-5-((1-(1-(acetylpiperidin-4-yl)-1H-pyrazol-4-yl)ethynyl)-N-(azepan-3-yl)-3-ureidothiophene-2-carboxamide; and
50) (S)—N-(azepan-3-yl)-5-((3-fluorophenyl)ethynyl)-3-ureidothiophene-2-carboxamide.

3. A pharmaceutical composition useful for the treatment and alleviation of a cancer disease, the pharmaceutical composition comprising the compound of claim 1 an active ingredient, wherein the cancer disease is gastric cancer, lung cancer, liver cancer, colon cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, hematologic malignancy, lymphoma, psoriasis, or fibroadenoma.

4. A method for the treatment and alleviation of a cancer disease, the method comprising administering a pharmaceutical composition comprising the compound of claim 1 an active ingredient, wherein the cancer disease is gastric cancer, lung cancer, liver cancer, colon cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, renal cancer, sarcoma, prostate cancer, urethral cancer, bladder cancer, hematologic malignancy, lymphoma, psoriasis, or fibroadenoma.

5. A pharmaceutical composition useful for the treatment and alleviation of acute myeloid leukemia, the pharmaceutical composition comprising the compound of claim 1 an active ingredient.

6. A method for the treatment and alleviation of acute myeloid leukemia, the method comprising administering a pharmaceutical composition comprising the compound of claim 1 an active ingredient.

7. A method for preparing a 2,3,5-substituted thiophene compound, the method comprising:
(Step 1) preparing a compound of Formula 4, in which an acetylene group is introduced into a C5 position of thiophene by reacting a 2-(Boc protected carboxamido)-3-amino-5-bromo-thiophene of Formula 2 with a trimethylsilylacetylene of Formula 3,

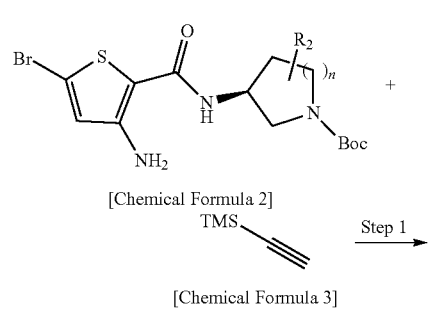

-continued

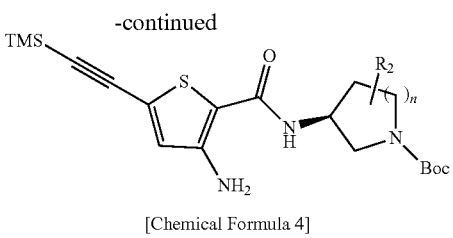

[Chemical Formula 4]

wherein, $R_2$ and n are the same as those defined in claim 1, is a trimethylsilyl group, and Boc is a tert-butoxycarbonyl group;

(Step 2) preparing a compound of Formula 5 by desorbing a trimethylsilyl (TMS) protecting group from the compound of Formula 4,

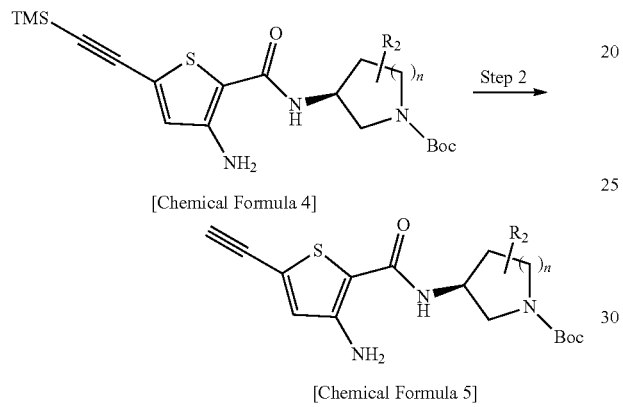

[Chemical Formula 5]

wherein, $R_2$ and n are the same as those defined in claim 1, is a trimethylsilyl group, and Boc is a tert-butoxycarbonyl group;

(Step 3) preparing a compound of Formula 7 by reacting the compound of Formula 5 with a halide compound of Formula 6,

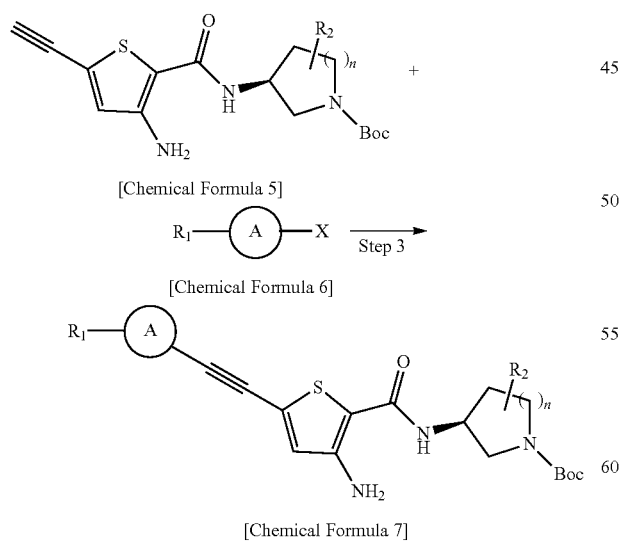

[Chemical Formula 7]

wherein, $R_1$, $R_2$, A, and n are the same as those defined in claim 1, X is a halogen atom, TMS is a trimethylsilyl group, and Boc is a tert-butoxycarbonyl group;

(Step 4) preparing a compound of Formula 9 by reacting the compound of Formula 7 with a trichloroacetyl isocyanate of Formula 8,

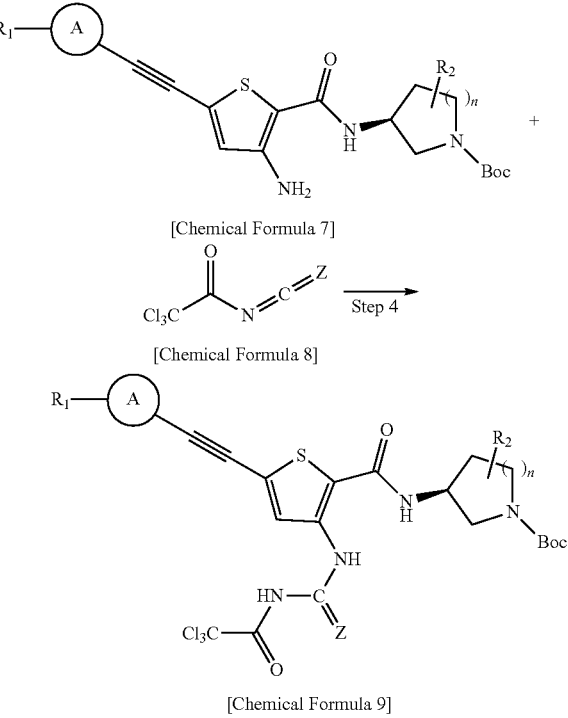

[Chemical Formula 9]

wherein, Z, $R_1$, $R_2$, A, and n are the same as those defined in claim 1, Boc is a tert-butoxycarbonyl group;

(Step 5) preparing a compound of Formula 10 by removing a trichloroacetyl ($F_3CC(O)$—) group from the compound of Formula 9,

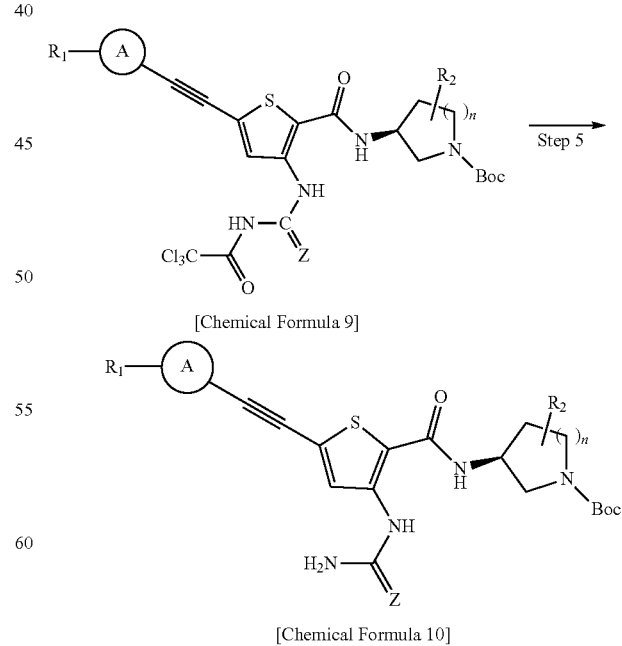

[Chemical Formula 10]

wherein, Z, $R_1$, $R_2$, A, and n are the same as those defined in claim 1, and Boc is a tert-butoxycarbonyl group; and (Step 6) preparing a compound of Formula 1a by desorbing a tert-butoxycarbonyl (Boc) group from the compound of Formula 10,

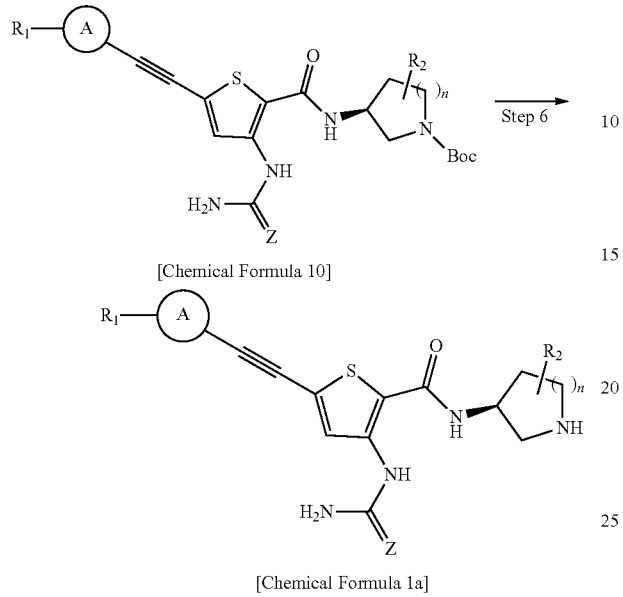

[Chemical Formula 10]

[Chemical Formula 1a]

wherein, Z, $R_1$, $R_2$, A, and n are the same as those defined in claim 1, and Boc is a tert-butoxycarbonyl group.

8. A method for preparing a 2,3,5-substituted thiophene compound, the method comprising:

(Step A) preparing a compound of Formula 7, in which an acetylene group is introduced into a C5 position of thiophene by reacting a 2-(Boc protected carboxamido)-3-amino-5-bromo-thiophene compound of Formula 2 with an acetylene compound of Formula 11,

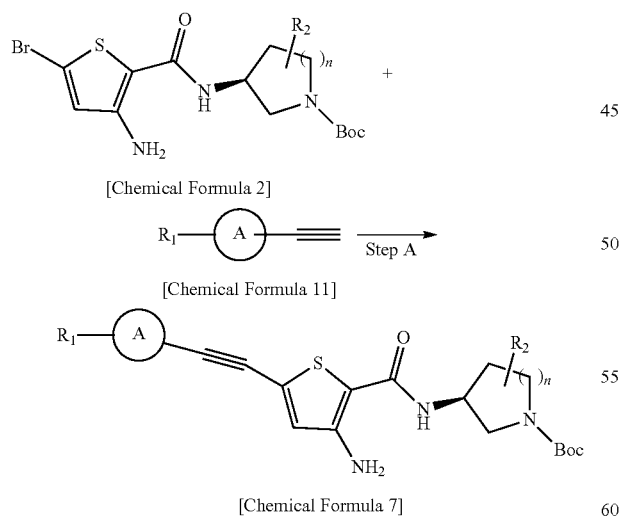

[Chemical Formula 2]

[Chemical Formula 11]

[Chemical Formula 7]

wherein, $R_1$, $R_2$, A, and n are the same as those defined in claim 1, Boc is a tert-butoxycarbonyl group;

(Step B) preparing a compound of Formula 9 by reacting the compound of Formula 7 with a trichloroacetyl isocyanate of Formula 8,

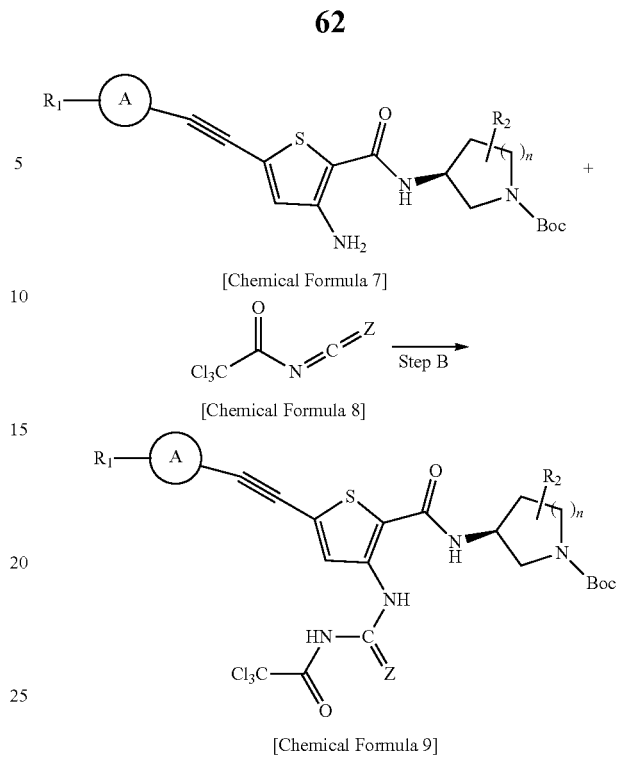

[Chemical Formula 7]

[Chemical Formula 8]

[Chemical Formula 9]

wherein, $R_1$, $R_2$, A, and n are the same as those defined in claim 1, and Boc is a tert-butoxycarbonyl group;

(Step C) preparing a compound of Formula 10 by removing a trichloroacetyl ($F_3CC(O)$—) group from the compound of Formula 9,

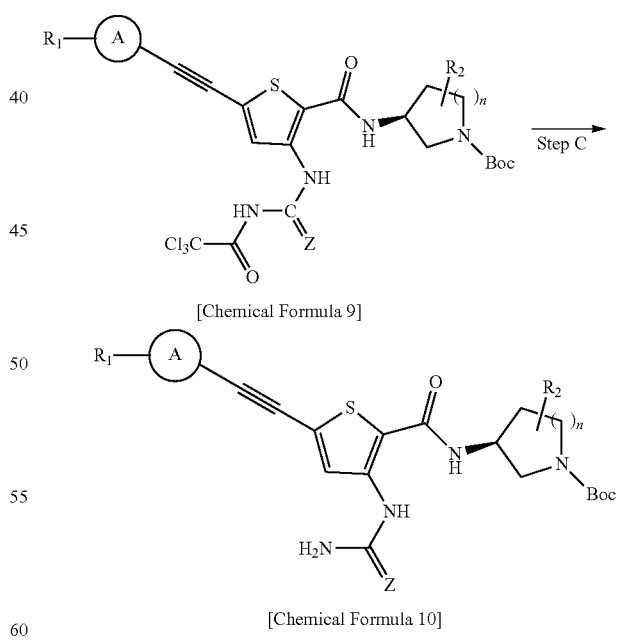

[Chemical Formula 9]

[Chemical Formula 10]

wherein, Z, $R_1$, $R_2$, A, and n are the same as those defined in claim 1, and Boc is a tert-butoxycarbonyl group; and (Step D) preparing a compound of Formula 1a by desorbing a tert-butoxycarbonyl (Boc) group from the compound of Formula 10,

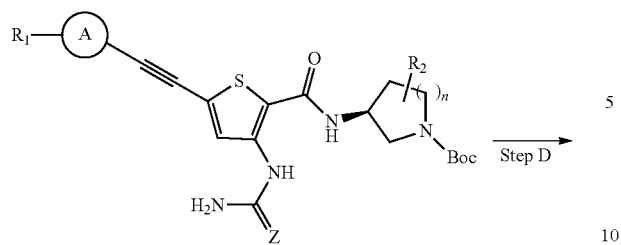
[Chemical Formula 10]
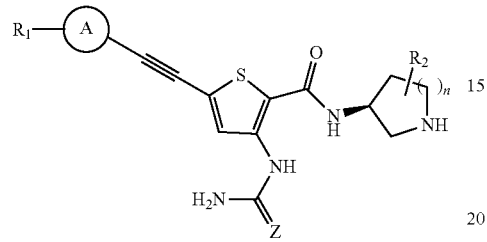
[Chemical Formula 1a]
wherein, Z, $R_1$, $R_2$, A, and n are the same as those defined in claim 1, and Boc is a tert-butoxycarbonyl group.
* * * * *